(12) United States Patent
Bielekova et al.

(10) Patent No.: US 10,877,049 B2
(45) Date of Patent: Dec. 29, 2020

(54) BIOMARKERS FOR DIAGNOSIS AND MANAGEMENT OF NEURO-IMMUNOLOGICAL DISEASES

(71) Applicants: The U.S.A., as represented by the Secretary, Department of Health and Human Services, Bethesda, MD (US); Montana State University, Bozeman, MT (US)

(72) Inventors: Bibiana Bielekova, Kensington, MD (US); Mika Komori, Bethesda, MD (US); Peter Kosa, Bethesda, MD (US); Mark C. Greenwood, Bozeman, MT (US); Christopher Barbour, Bozeman, MT (US)

(73) Assignees: The United States of America, as represented by the Secretary, Department of Health and Human Services, Bethesda, MD (US); Montana State University, Bozeman, MT (US)

( * ) Notice: Subject to any disclaimer, the term of this patent is extended or adjusted under 35 U.S.C. 154(b) by 0 days.

(21) Appl. No.: 16/284,914

(22) Filed: Feb. 25, 2019

(65) Prior Publication Data
US 2019/0265254 A1 Aug. 29, 2019

Related U.S. Application Data

(62) Division of application No. 15/504,438, filed as application No. PCT/US2015/045549 on Aug. 17, 2015, now Pat. No. 10,261,098.

(60) Provisional application No. 62/038,530, filed on Aug. 18, 2014.

(51) Int. Cl.
*G01N 33/68* (2006.01)

(52) U.S. Cl.
CPC ... *G01N 33/6896* (2013.01); *G01N 2333/705* (2013.01); *G01N 2800/285* (2013.01); *G01N 2800/52* (2013.01); *G01N 2800/60* (2013.01)

(58) Field of Classification Search
None
See application file for complete search history.

(56) References Cited

U.S. PATENT DOCUMENTS 10,261,098 B2 * 4/2019 Bielekova .......... G01N 33/6896
2008/0181886 A1   7/2008 Kelley
2017/0242043 A1 * 8/2017 Bielekova .......... G01N 33/6896

FOREIGN PATENT DOCUMENTS

WO  WO 2013/049362  4/2013

OTHER PUBLICATIONS

Mandel et al., Tight junction proteins expression and modulation in immune cells and multiple sclerosis, 2012, J. Cell. Mol. Med. 16(4):765-775 (Year: 2012).*
Masvekar et al., Cerebrospinal fluid biomarkers link toxic astrogliosis and microglial activation to multiple sclerosis severity, 2019, Multiple Sclerosis and Related Disorders 28:34-43 (Year: 2019).*
Barbour et al., Molecular-based diagnosis of Multiple Sclerosis and its progressive stage, 2017, Ann Neurol. 82(5): 795-812 (Year: 2017).*
Awad et al., "Analyses of Cerebrospinal Fluid in the Diagnosis and Monitoring of Multiple Sclerosis," *J. Neuroimmunol.*, vol. 219:1-7, 2010.
Cayrol et al., "Activated Leukocyte Cell Adhesion Molecule Promotes Leukocyte Trafficking into the Central Nervous System," *Nature Immunol.*, vol. 9:137-145, 2008.
Cepok et al., "Short-Lived Plasma Blasts are the Main B Cell Effector Subset during the Course of Multiple Sclerosis," *Brain*, vol. 128:1667-1676, 2005.
Correale et al., "Chitinase Effects on Immune Cell Response in Neuromyelitis Optica and Multiple Sclerosis," *Mult. Scler. J.*, vol. 17:521-531, 2011.
Galboiz et al., "The Profile of Matrix Metalloproteinases (MMPSs) and Tissue Inhibitors of Metalloproteinases (TIMPs) in Multiple Sclerosis," Ninth Meeting of the European Neurological Society, Jun. 5-9, 1999, Milan Italy, Abstracts of Symposia, Free Communications and Posters, *J. Neurol.*, vol. 246 (Suppl. 1), p. 423:I89-I90, 1999.
Gold et al., "Aptamer-Based Multiplexed Proteomic Technology for Biomarker Discovery," *PLoS ONE*: vol. 5:e15004, 2010.
Gold et al., "Aptamers and the RNA World, Past and Present," *Cold Spring Harb Perspect. Biol.*, vol. 4:a003582, 2012.
Hecker et al., "Reassessment of Blood Gene Expression Markers for the Prognosis of Relapsing-Remitting Multiple Sclerosis," *PLoS ONE*, vol. 6:e29648, 2011.
Komori et al., "Proteomic Pattern Analysis Discriminates Among Multiple Sclerosis-Related Disorders," *Ann Neurol.*, vol. 71:614-623, 2012.

(Continued)

*Primary Examiner* — John D Ulm
(74) *Attorney, Agent, or Firm* — Klarquist Sparkman, LLP

(57) ABSTRACT

Biomarkers associated with neuroimmunological disease are described. The disclosed biomarkers are secreted proteins identified in cerebral spinal fluid (CSF) samples of patients with neurological disease. The disclosed biomarkers identify patients with intrathecal inflammation, distinguish multiple sclerosis (MS) patients from patients with other types of inflammatory neurological diseases and from subjects without MS, distinguish progressive MS patients from patients with relapsing-remitting MS, identify subjects with non-MS inflammatory neurological diseases, differentiate healthy subjects from patients with any type of neurological disease, and/or identify subjects with increased disability, CNS tissue damage and/or neurodegeneration. Process-specific biomarkers that can be used in place of a brain biopsy to identify immune cell infiltration and/or activation in the CNS are also described. Methods of treating subject with neurological disease, and methods of evaluating the efficacy of particular treatments, based on detection of the disclosed biomarkers are also described.

11 Claims, 36 Drawing Sheets

(56) References Cited

OTHER PUBLICATIONS

McMillan et al., "Increased Soluble VCAM-1 Levels in Cerebrospinal Fluids of Patients with Multiple Sclerosis," *J. Neuroimmunol.*, vol. 54:181, p. 17.11, 1994.
Mitosek-Szewczyk et al., "Impact of Cladribine on Soluble Adhesion Molecules in Multiple Sclerosis," *Acta Neurol. Scand.*, vol. 122:409-413, 2010.
Ottervald et al., "Multiple Sclerosis: Identification and Clinical Evaluation of Novel CSF Biomarkers," *J. Proteomics*, vol. 73:1117-1132, 2010.
Thangarajh et al., "The Expression of BAFF-Binding Receptors is not Altered in Multiple Sclerosis or Myasthenia Gravis," *Scand. J. Immunol.*, vol. 65:461-466, 2007.
Tumani et al., "Cerebrospinal Fluid Biomarkers in Multiple Sclerosis," *Neurobiol. Dis.*, vol. 35:117-127, 2009.
Varghese et al., "Chitotriosidase—a Putative Biomarker for Sporadic Amyotrophic Lateral Sclerosis," *Clin. Proteomics*, vol. 10:1-9, 2013.
Vincent et al, "The BAFF/APRIL System: Emerging Functions Beyond B Cell Biology and Autoimmunity," *Cytokine Growth Factor Rev.*, vol. 24:203-215, 2013.
Vudattu et al., "Increased Numbers of IL-7 Receptor Molecules on CD4+CD25—CD107a+ T-Cells in Patients with Autoimmune Diseases Affecting the Central Nervous System," *PLoS ONE*, vol. 4:e6534, 2009.
Webber et al., "Proteomics Analysis of Cancer Exosomes Using a Novel Modified Aptamer-based Array (SOMAscan™) Platform," *Mol. Cell. Proteomics*, vol. 13:1050-1064, 2014.

\* cited by examiner

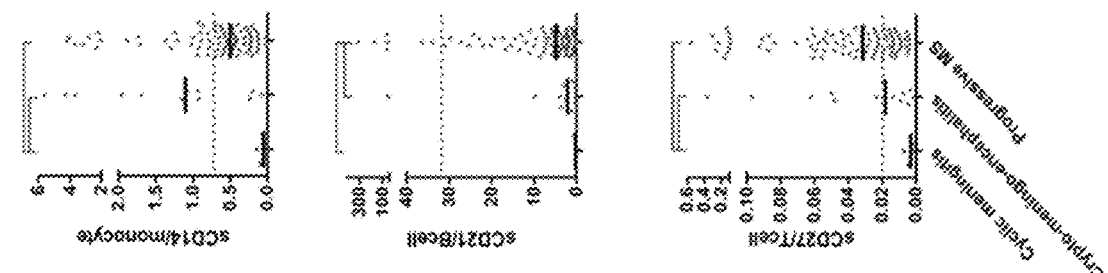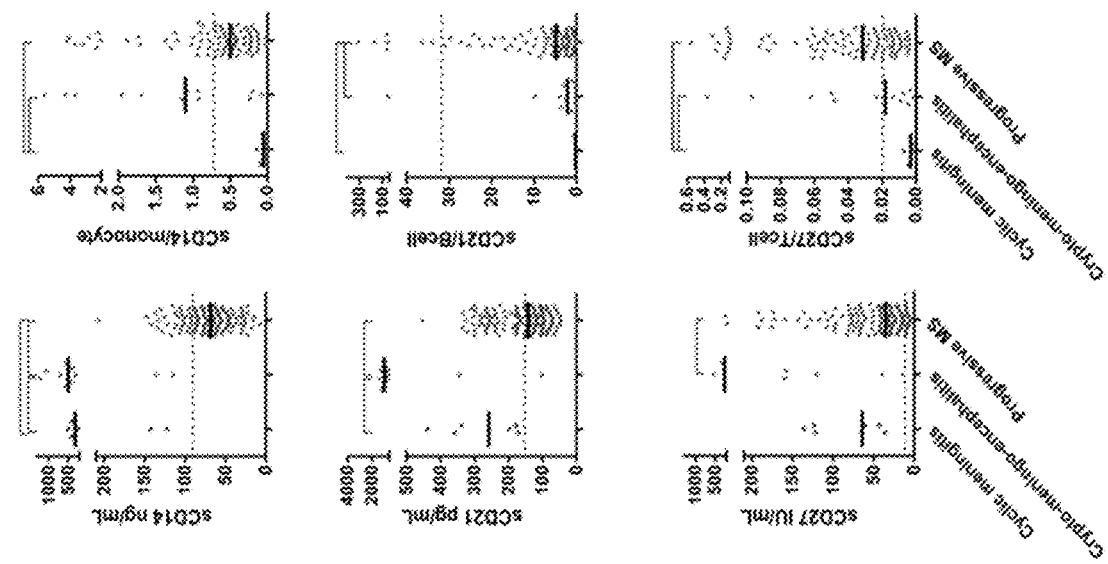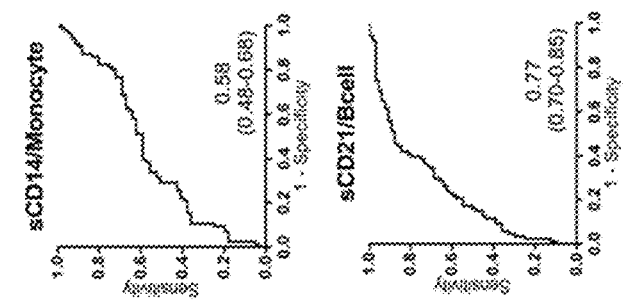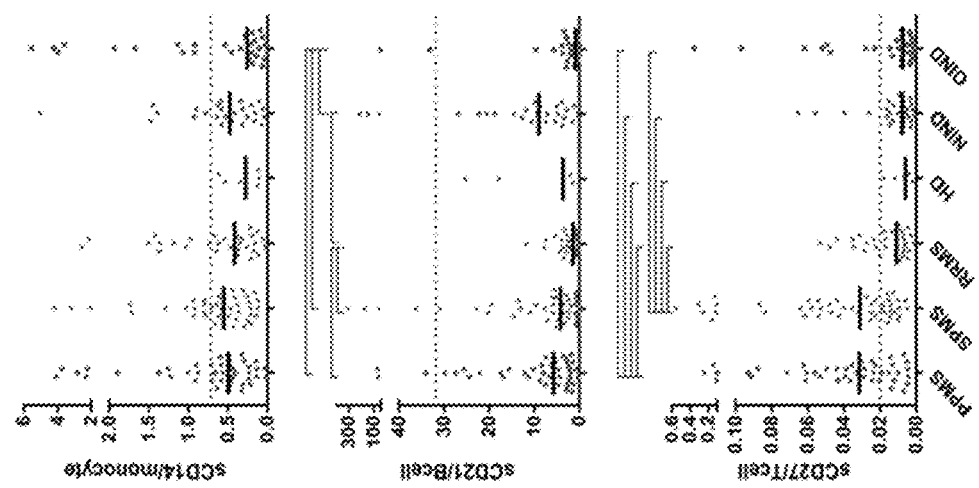

FIG. 7A
FIG. 7B
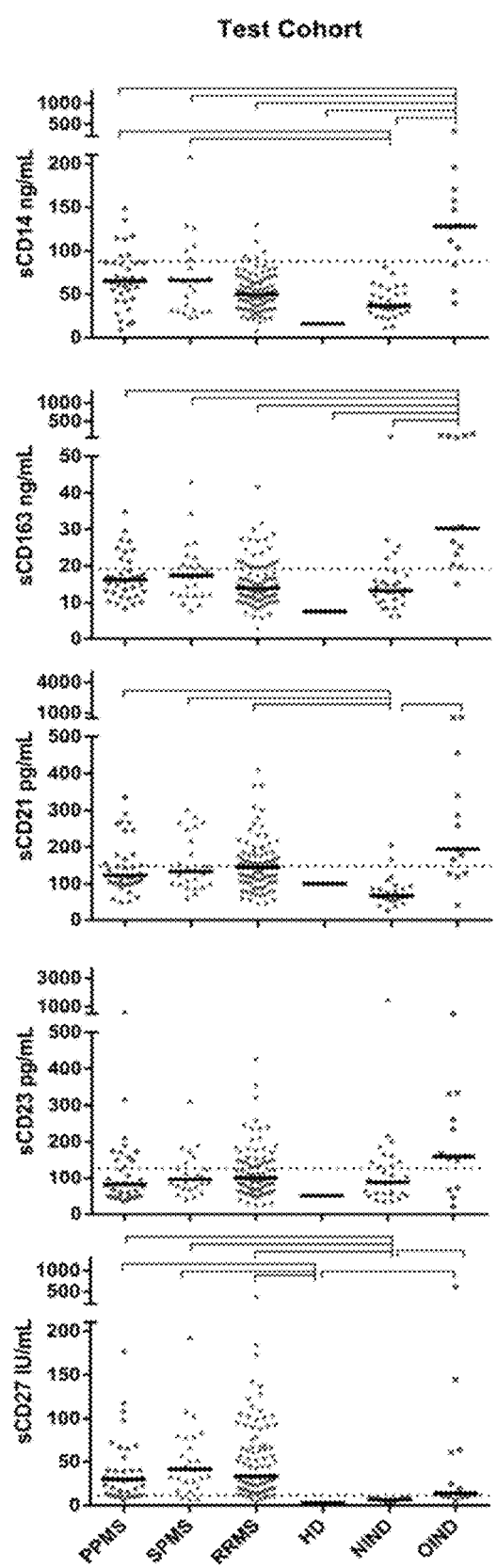
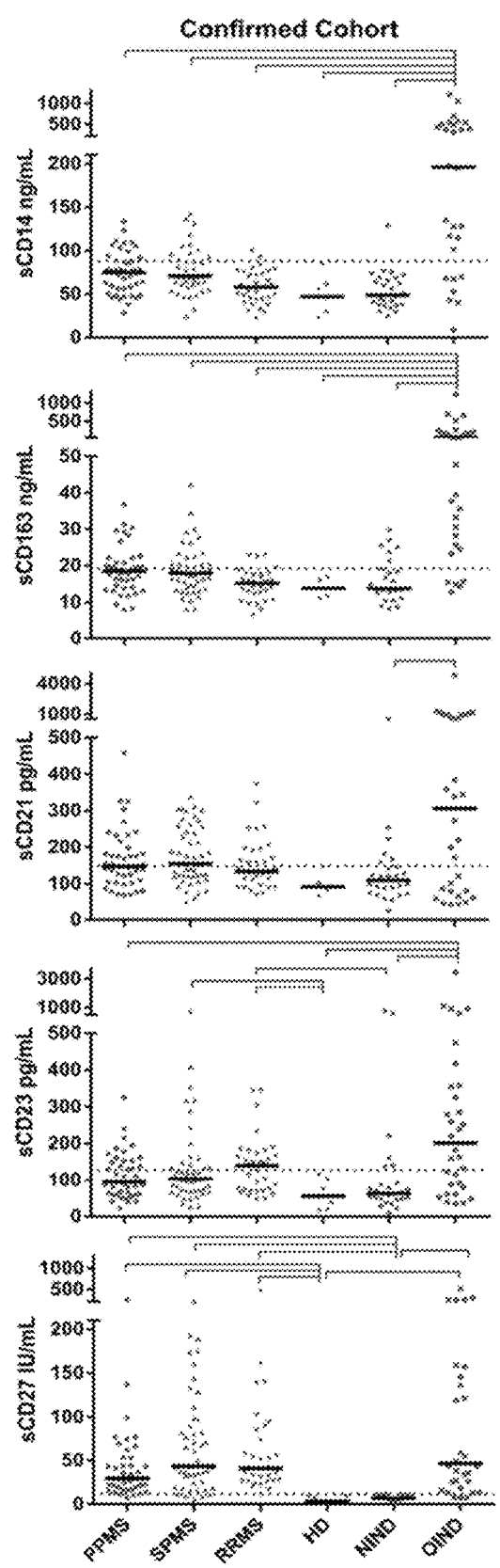

FIG. 10A

| | Pilot Cohort A | | | | | Confirmatory Cohort B | | | | | | All | | | | | |
|---|---|---|---|---|---|---|---|---|---|---|---|---|---|---|---|---|---|
| | PPMS | SPMS | RRMS | HD | NIND | OIND | PPMS | SPMS | RRMS | HD | NIND | OIND | PPMS | SPMS | RRMS | HD | NIND | OIND |
| N | 36 | 25 | 88 | 1 | 30 | 13 | 45 | 49 | 33 | 7 | 27 | 32 | 81 | 74 | 121 | 8 | 57 | 45 |
| female/male | 15/21 | 11/14 | 50/38 | 1/0 | 25/5 | 5/8 | 21/24 | 32/17 | 19/14 | 3/4 | 15/12 | 10/22 | 36/45 | 43/31 | 69/52 | 4/4 | 40/17 | 15/30 |
| Age, years | 54ᵃ (42-66) | 51ᵃ (29-66) | 38ᵃ (24-69) | 29ᵃ (29-29) | 42ᵃ (11-66) | 51ᵃ (23-63) | 56ᵃ (31-70) | 54ᵃ (28-66) | 41ᵃ (18-66) | 40ᵃ (34-56) | 56ᵃ (18-75) | 46ᵃ (3-75) | 55ᵃ (31-70) | 54ᵃ (28-66) | 38ᵃ (18-69) | 38ᵃ (29-56) | 51ᵃ (11-75) | 50ᵃ (3-75) |
| Disease duration, years | 11.6ᵃ (1-33.2) | 14.2ᵃ (1.2-43.8) | 2.6 (0-33) | n/a | 2.4 (0.3-17.8) | 2.7ᵃ (0.92-12.8) | 19ᵃ (1-33.8) | 24.1ᵃ (1.4-43.5) | 1.6 (0-36.3) | n/a | 4.2ᵃ (0.4-34.6) | 1.9 (0.4-7.8) | 16.4ᵃ (1-33.8) | 21.3ᵃ (1.2-43.5) | 2.1 (0-36.3) | n/a | 2.5 (0.3-34.6) | 2.2 (0.4-12.8) |
| EDSS | 6ᵃ (2-7.5) | 6ᵃ (6-7) | 1.5ᵃ (0-5) | n/a | n/a | n/a | 6ᵃ (2-6.5) | 6.5ᵃ (2.5-7) | 2.5 (1-2.5) | n/a | n/a | n/a | 6ᵃ (2-7.5) | 6.5ᵃ (2.5-7) | 2 (0-5) | n/a | n/a | n/a |
| SRRS | 65ᵃ (45-94) | 64ᵃ (45-75) | 92ᵃ (70-100) | n/a | n/a | n/a | 68ᵃ (41-94) | 59 (44-82) | 89ᵃ (77-98) | n/a | n/a | n/a | 66ᵃ (41-94) | 60ᵃ (44-82) | 91ᵃ (70-100) | n/a | n/a | n/a |
| IgG index | 0.66ᵃ (0.44-2.85) | 0.72ᵃ (0.42-1.85) | 0.87ᵃ (0.50-3.83) | 0.46ᵃ (0.46-0.46) | 0.50ᵃ (0.38-0.61) | 0.55ᵃ (0.47-0.70) | 0.68ᵃᵇ (0.42-3.52) | 0.94ᵃ (0.45-3.62) | 0.85ᵃ (0.55-2.81) | 0.53ᵃ (0.37-0.59) | 0.51ᵃ (0.42-0.62) | 0.62ᵃᵇ (0.37-1.35) | 0.68ᵃᵇ (0.42-3.52) | 0.76ᵃᵇ (0.42-3.62) | 0.85ᵃ (0.50-3.83) | 0.51ᵃ (0.37-0.59) | 0.5ᵃ (0.38-0.62) | 0.58ᵃ (0.37-1.35) |

FIG. 10B

FIG. 15C
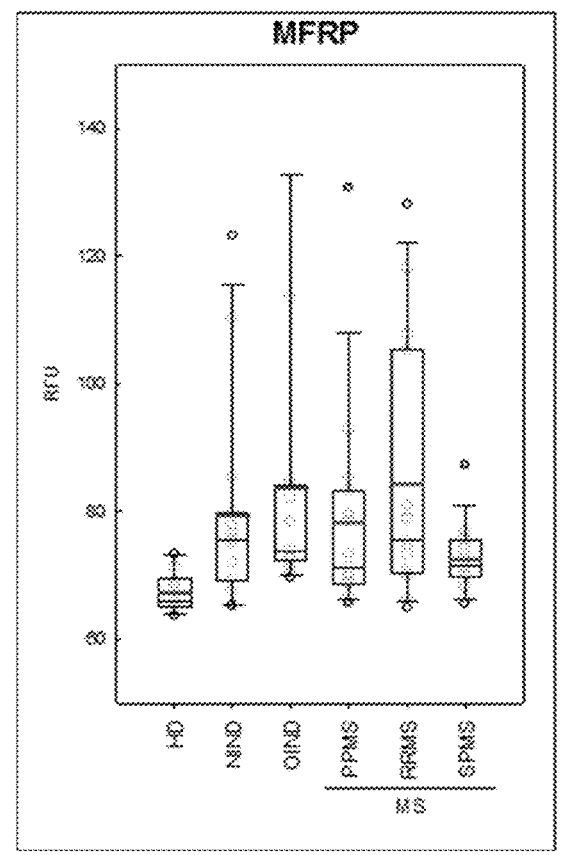
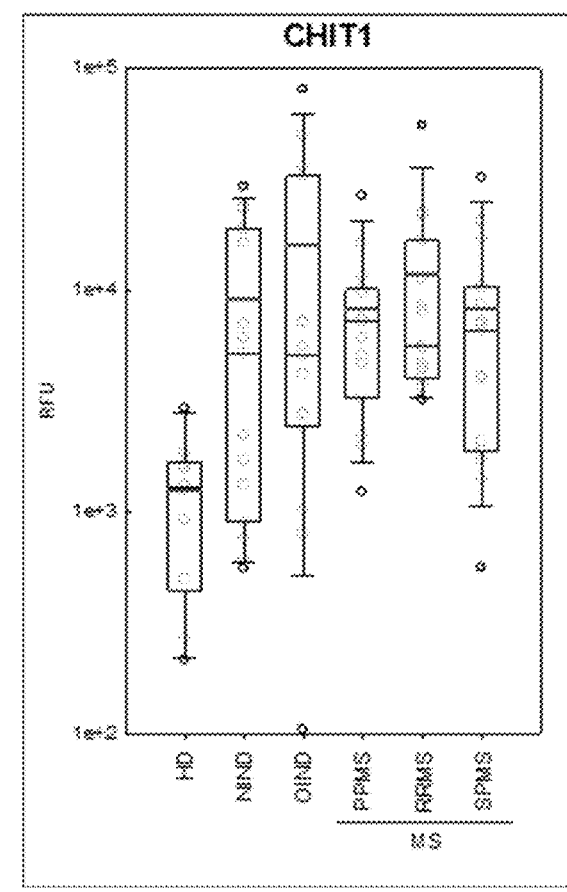

progressive MS vs relapsing-remitting MS

FIG. 20

| Diagnosis | Discovery cohort (N=85) | | | | | Validation cohort (N=225) | | | | | |
|---|---|---|---|---|---|---|---|---|---|---|---|
| | HD | NIND | OIND | RRMS | PPMS | SPMS | HD | NIND | OIND | RRMS | PPMS | SPMS |
| N (female/male) | 5/5 | 12/3 | 7/8 | 9/6 | 9/6 | 11/4 | 9/16 | 33/9 | 18/24 | 36/14 | 17/23 | 33/17 |
| Average age | 38.8 | 47.0 | 46.4 | 37.3 | 53.6 | 54.0 | 40.5 | 47.9 | 46.9 | 39.6 | 53.7 | 53.6 |
| SD | 28.9 | 13.1 | 14.6 | 8.7 | 7.6 | 7.2 | 11.7 | 10.8 | 13.8 | 9.2 | 9.6 | 10.7 |
| range | 28.9-56.2 | 21.0-66.0 | 22.1-71.0 | 27.9-54.4 | 36.0-64.5 | 38.4-66.0 | 22.4-58.4 | 18.2-70.6 | 15.4-74.2 | 18.0-59.9 | 28.2-70.4 | 27.4-69.6 |
| Disease duration | NA | 5.1 | 4.0 | 2.7 | 10.0 | 25.0 | NA | 5.4 | 4.2 | 4.4 | 10.6 | 20.4 |
| SD | NA | 5.2 | 3.9 | 5.4 | 5.9 | 7.7 | NA | 7.6 | 3.9 | 6.0 | 7.5 | 10.7 |
| range | NA | 0.4-14.9 | 0.4-14.9 | 0.1-20.1 | 1.6-24.2 | 9.5-38.4 | NA | 0.2-34.5 | 0.5-13.1 | 0.0-20.7 | 0.5-30.3 | 1.5-42.4 |
| EDSS | 0.3 | 3.7 | 2.6 | 1.6 | 5.3 | 6.3 | 0.5 | 2.0 | 3.7 | 1.6 | 5.3 | 5.9 |
| SD | 0.5 | 2.1 | 2.2 | 0.8 | 1.4 | 0.5 | 0.5 | 2.1 | 2.8 | 1.3 | 1.7 | 1.4 |
| range | 0.0-1.0 | 1.0-6.5 | 0.0-6.5 | 1.0-4.0 | 3.0-6.5 | 5.0-7.0 | 0.0-1.5 | 0.0-6.5 | 0.0-9.0 | 0.0-6.0 | 2.0-8.5 | 2.0-8.0 |
| SNRS | 98.6 | 80.7 | 83.7 | 94.1 | 66.9 | 57.5 | 97.4 | 90.4 | 78.6 | 92.1 | 67.4 | 60.1 |
| SD | 2.0 | 13.1 | 16.5 | 4.4 | 10.6 | 7.1 | 3.1 | 13.3 | 19.8 | 8.9 | 15.6 | 15.9 |
| range | 95-100 | 57-98 | 57-100 | 80-98 | 50-84 | 49-75 | 87-100 | 51-100 | 42-100 | 65-100 | 24-94 | 29-87 |
| SDMT | 49.1 | 46.1 | 44.9 | 52.9 | 43.4 | 37.4 | 51.2 | 49.8 | 45.3 | 53.2 | 40.6 | 37.6 |
| SD | 14.4 | 10.3 | 11.2 | 9.4 | 11.4 | 10.4 | 11.5 | 14.3 | 14.7 | 10.5 | 12.5 | 13.4 |
| range | 32-69 | 31-63 | 28-65 | 46-70 | 28-68 | 20-51 | 32-71 | 19-80 | 26-77 | 32-76 | 4-58 | 12-59 |

SD = standard deviation, EDSS = expanded disability status scale, SNRS = Scripps neurological rating scale, SDMT = symbol digit modality test, HD = healthy donors, NIND = non-inflammatory neurological disorders, OIND = other inflammatory neurological disorders, RRMS = relapsing-remitting multiple sclerosis, PPMS = primary progressive multiple sclerosis, SPMS = secondary progressive multiple sclerosis

FIG. 21

| Molecule | Manufacturer (Antibodies/Kit) | CSF dilution factor | Detection limit [a] | Intra-assay variation [b] | Inter-assay variation [b] |
|---|---|---|---|---|---|
| IL-6 | Meso Scale Diagnostics, Rockville, MD (K150490) | 1 | 0.74 pg/mL | 6.4% | 9.6% |
| IL6Ra | R&D Systems, Minneapolis, MN (MAB227, BAF227) | 10 | 6.3 pg/mL | 2.2% | 4.0% |
| IL-8 | Meso Scale Diagnostics (K150490) | 1 | 0.53 pg/mL | 6.7% | 9.8% |
| sCD23 | R&D Systems (MAB1231, BAF123) | 2 | 16.0 pg/mL | 4.0% | 5.3% |
| sCD27 | Sanquin, Amsterdam, the Netherlands (M1960) | 20 | 0.4 U/mL | 2.3% | 2.9% |
| sCD163 | R&D Systems (MAB16071, BAM16072) | 10 | 0.85 ng/mL | 2.7% | 5.8% |
| CXCL13 | R&D Systems (MAB801, BAF801) | 1 | 17.4 pg/mL | 5.8% | 8.8% |
| BAFF | R&D Systems (DY124) | 3 | 2.1 pg/mL | 4.7% | 8.6% |
| BCMA | R&D Systems (DY193) | 10 | 12.8 pg/mL | 3.1% | 4.7% |
| BDNF | R&D Systems (DY248) | 1 | 18.7 pg/mL | 4.7% | 8.5% |
| HGF | R&D Systems (DY294) | 2 | 13.0 pg/mL | 3.9% | 8.0% |
| NCAM1 | R&D Systems (DY2408) | 200 | 34.7 ng/mL | 3.1% | 4.2% |
| Sirtuin2 | R&D Systems (MAB4358, BAF4358) | 1 | 33.4 pg/mL | 8.8% | 10.1% |
| Cytochrome C | Enzo Life Sciences, Farmingdale, NY (ADI-900-141) | 20 | 562.0 pg/mL | 2.7% | 8.8% |

[a] When diluted CSF was used, detection limit is recalculated to reflect utilized concentration factor.

[b] Median value of concentration CV

FIG. 22A

A) Random Forest classifier for MS vs non-MS

| SomaID | Gene | Target | Variable importance (Random Forest) | AUC Validation Cohort (N=225) | AUC Discovery Cohort (N=85) | p value* |
|---|---|---|---|---|---|---|
| SL003322/SL004672 | FLT4/TNFRSF17 | VEGF sR3/BCMA | 12.86 | 0.91 | 0.89 | <0.0001 |
| SL004672/SL010450 | TNFRSF17/CD48 | BCMA/CD48 | 12.24 | 0.90 | 0.90 | <0.0001 |
| SL004672/SL000474 | TNFRSF17/IL16 | BCMA/IL-16 | 11.77 | 0.92 | 0.89 | <0.0001 |
| SL004672/SL003739 | TNFRSF17/TNFRSF6B | BCMA/DcR3 | 11.54 | 0.90 | 0.92 | <0.0001 |
| SL004672/SL005764 | TNFRSF17/CD163 | BCMA/sCD163 | 11.29 | 0.90 | 0.93 | <0.0001 |
| SL004672/SL014469 | TNFRSF17/SHC1 | BCMA/SHC1 | 11.19 | 0.90 | 0.87 | <0.0001 |
| SL004672 | TNFRSF17 | BCMA | 10.78 | 0.84 | 0.87 | |
| SL004672/SL010529 | TNFRSF17/UFC1 | BCMA/UFC1 | 10.49 | 0.90 | 0.89 | <0.0001 |
| SL007674/SL000467 | LY9/IGHG1 | LY9/IgG | 10.04 | 0.90 | 0.89 | <0.0001 |
| SL000508/SL000467 | LTA LTB/IGHG1 | Lymphotoxin a2/b1/IgG | 10.04 | 0.90 | 0.90 | <0.0001 |
| SL000525 | MMP7 | MMP-7 | 8.48 | 0.71 | 0.70 | |
| SL016928 | SLAMF7 | SLAF7 | 8.33 | 0.77 | 0.79 | |
| SL001800 | TNFRSF1B | TNF sR-II | 8.32 | 0.66 | 0.67 | |
| SL000467 | IGHG1 | IgG | 7.50 | 0.86 | 0.87 | |
| SL010450 | CD48 | CD48 | 7.07 | 0.64 | 0.67 | |
| SL001720 | VCAM1 | VCAM-1 | 5.73 | 0.60 | 0.65 | |
| SL006029 | CHIT1 | Chitotriosidase-1 | 5.05 | 0.65 | 0.66 | |
| SL004182 | PLA2G5 | GV | 4.85 | 0.56 | 0.53 | |

FIG. 22B

Random Forest classifier for progressive MS vs RRMS

| SomaID | Gene | Target | Variable importance (Random Forest) | AUC Validation Cohort (N=225) | AUC Discovery Cohort (N=85) | p value* |
|---|---|---|---|---|---|---|
| SL005194/SL005233 | JAM3/EDA2R | JAM-C/XEDAR | 7.05 | 0.83 | 0.87 | 0.0001 |
| SL004136/SL005233 | TYRO3/EDA2R | Dtk/XEDAR | 6.93 | 0.82 | 0.86 | 0.0001 |
| SL005233/SL007680 | EDA2R/ROBO2 | XEDAR/ROBO2 | 6.80 | 0.82 | 0.88 | 0.0001 |
| SL000024/SL007680 | F3/ROBO2 | TF/ROBO2 | 6.63 | 0.81 | 0.68 | 0.0048 |
| SL005233/SL004304 | EDA2R/STX1A | XEDAR/STX1a | 6.57 | 0.80 | 0.85 | 0.0001 |
| SL005233/SL004844 | EDA2R/EPHA5 | XEDAR/EphA5 | 6.52 | 0.84 | 0.87 | 0.0001 |
| SL000508/SL000308 | LTA LTB/SERPING1 | Lymphotoxin a2/b1/C1-Esterase Inhibitor | 6.33 | 0.83 | 0.71 | 0.0011 |
| SL004639/SL005233 | NTRK3/EDA2R | TrkC/XEDAR | 6.27 | 0.83 | 0.87 | 0.0001 |
| SL004652/SL005233 | WIF1/EDA2R | WIF-1/XEDAR | 6.04 | 0.82 | 0.74 | 0.0001 |
| SL005233/SL003166 | EDA2R/ALCAM | XEDAR/ALCAM | 5.86 | 0.82 | 0.92 | 0.0001 |
| SL005233/SL004154 | EDA2R/L1CAM | XEDAR/NCAM-L1 | 5.83 | 0.83 | 0.83 | 0.0001 |
| SL003199/SL004844 | TIE1/EPHA5 | sTie-1/EphA5 | 5.69 | 0.81 | 0.81 | 0.0001 |
| SL005233/SL007179 | EDA2R/EPHB2 | XEDAR/EPHB2 | 5.58 | 0.82 | 0.91 | 0.0001 |
| SL003327/SL000622 | CFD/F5 | Factor D/Coagulation Factor V | 5.55 | 0.80 | 0.72 | 0.0003 |
| SL005233/SL004469 | EDA2R/APP | XEDAR/amyloid precursor protein | 5.34 | 0.83 | 0.82 | 0.0001 |
| SL004149/SL000508 | IL13RA1/LTA LTB | IL-13 Ra1/Lymphotoxin a2/b1 | 5.31 | 0.80 | 0.71 | 0.0010 |
| SL004844/SL006970 | EPHA5/DLL1 | EphA5/DLL1 | 4.98 | 0.80 | 0.72 | 0.0006 |
| SL004805/SL012538 | CADM1/CDNF | Nectin-like protein 2/ARMEL | 4.92 | 0.80 | 0.67 | 0.0075 |
| SL012538/SL005181 | CDNF/IL20RA | ARMEL/IL-20 Ra | 4.70 | 0.81 | 0.80 | 0.0001 |
| SL005220 | SHH | Sonic Hedgehog | 4.60 | 0.73 | 0.72 | |
| SL005233/SL008728 | EDA2R/NRXN3 | XEDAR/NRX3B | 4.47 | 0.80 | 0.87 | 0.0001 |
| SL007680/SL011068 | ROBO2/IL17RC | ROBO2/IL-17 RC | 4.29 | 0.80 | 0.81 | 0.0001 |
| SL005233/SL004805 | EDA2R/CADM1 | XEDAR/Nectin-like protein 2 | 4.24 | 0.80 | 0.88 | 0.0001 |
| SL005233/SL005208 | EDA2R/RTN4R | XEDAR/Nogo Receptor | 4.22 | 0.83 | 0.86 | 0.0001 |
| SL000508 | LTA LTB | Lymphotoxin a2/b1 | 4.14 | 0.79 | 0.61 | |
| SL005233/SL004610 | EDA2R/LRP8 | XEDAR/LRP8 | | 0.81 | 0.89 | 0.0001 |

BIOMARKERS FOR DIAGNOSIS AND MANAGEMENT OF NEURO-IMMUNOLOGICAL DISEASES

CROSS REFERENCE TO RELATED APPLICATIONS

This is a divisional of U.S. application Ser. No. 15/504,438, filed Feb. 16, 2017, issued as U.S. Pat. No. 10,261,098 on Apr. 16, 2019, which is the U.S. National Stage of International Application No. PCT/US2015/045549, filed Aug. 17, 2015, which was published in English under PCT Article 21(2), which claims the benefit of U.S. Provisional Application No. 62/038,530, filed Aug. 18, 2014. The above-listed applications are herein incorporated by reference in their entirety.

FIELD

This disclosure concerns biomarkers of intrathecal inflammation and multiple sclerosis, and the use of such biomarkers, such as to guide treatment decisions.

BACKGROUND

The absence of reliable biomarkers for intrathecal inflammation is a critical impediment to broad therapeutic progress in neuroimmunology. This notion is exemplified by augmented therapeutic developments in relapsing-remitting multiple sclerosis (RRMS) driven by the recognition that contrast-enhancing lesions (CELs) on brain magnetic resonance imaging (MRI) reflect perivascular inflammation (Sormani and Bruzzi, *Lancet Neurol* 12(7):669-676, 2013; Filippi et al., *Lancet Neurol* 11:349-360, 2012). Unfortunately, clinical success of CELs led to a false generalization that CELs are always associated with inflammation or represent all inflammatory activity. Such assumptions can lead to the administration of immunomodulatory agents to patients whose primary pathology is hypoxia or malignancy, or to the simplified (and possibly incorrect) conclusion that the immune system no longer plays a role in progressive multiple sclerosis (MS).

The evaluation of cerebrospinal fluid (CSF) has been paradoxically discouraged, partly by an erroneous perception that the lumbar puncture is dangerous, but most importantly, by the limited clinical value of available CSF biomarkers (Stangel et al., *Nat Rev Neurol* 9(5):267-276, 2013). When determining if patients have an immune-mediated central nervous system (CNS) disease or when recommending options for patients with neuroimmunological disorders who are unresponsive to applied treatment, IgG index, oligoclonal bands (OCBs), or CSF pleiocytosis provide unsatisfactory sensitivity/specificity ratios (Link et al., *J Neuroimmunol* 180:17-28, 2006). The customary solution is a brain biopsy or a blind trial of immunomodulatory agents. Unfortunately, both approaches expose patients to substantial risks and may still lead to unsatisfactory outcomes. Indeed, brain biopsies in neuroimmunological disorders are frequently "non-diagnostic," either due to sampling error, limited diversity of immunohistochemical stains, or the development of "non-specific" inflammation by the time such a radical diagnostic step is considered.

Hence, there remains a great need for direct biomarkers of intrathecal inflammation, including biomarkers of MS, ideally those that provide information about the phenotype of the inflammatory process (Bielekova and Martin, *Brain* 127:1463-1478, 2004).

SUMMARY

Biomarkers associated with neuroimmunological disease are described. The biomarkers disclosed herein are capable of identifying patients with intrathecal inflammation, distinguishing subjects that have MS from subjects that do not have MS, distinguishing MS patients from patients with other types of inflammatory neurological diseases, distinguishing progressive MS patients from patients with RRMS, identifying subjects with non-MS inflammatory neurological diseases, differentiating healthy subjects from patients with any type of neurological disease and/or identifying subjects with increased disability, CNS tissue damage and/or neurodegeneration. Also disclosed are process-specific biomarkers that can be used in place of a brain biopsy to identify immune cell infiltration and/or activation in the CNS.

Provided herein are methods of identifying a subject as having MS; identifying a subject with MS as having progressive MS or RRMS; identifying a subject as having intrathecal inflammation; identifying an MS patient as having progressive MS; identifying a subject as having an inflammatory neurological disease other than MS; identifying a subject as having a neurological disease; and identifying a subject having CNS tissue injury and/or neurodegeneration. Each method includes detecting specific biomarkers in the CSF of a subject.

Methods for identifying immune cell infiltration and/or activation in CNS tissue of a subject having a neurological disorder are further provided by the present disclosure.

Also provided are methods of treating MS in a subject, methods of treating an inflammatory neurological disease in a subject, and methods of treating an inflammatory neurological disease other than MS in a subject. Each method includes measuring specific biomarkers in the CSF of the subject and administering an appropriate therapy to the subject, such as an immunomodulatory therapy if inflammatory biomarkers are elevated.

Further provided are methods of evaluating the effectiveness of a therapy for treating MS or an inflammatory neurological disease, and a method of evaluating the effectiveness of a therapy for treating MS or an inflammatory neurological disease other than MS. Each method includes measuring specific biomarkers (which includes biomarker ratios) in the CSF before and after treatment.

The foregoing and other objects, features, and advantages of the invention will become more apparent from the following detailed description, which proceeds with reference to the accompanying figures.

BRIEF DESCRIPTION OF THE DRAWINGS

In FIG. 1B, grey brackets represent statistically significant differences (p<0.01) that were reproduced in only one of the cohorts (see FIG. 6), whereas black brackets represent those differences that reached statistical significance (p<0.05) in both cohorts based on pair-wise multiple comparisons with Tukey's correction method. Dotted lines represent the upper limit of normal values (calculated as mean+2 standard deviations (SD) from healthy donor (HD)), while thick black bars represent the median for each diagnostic category. FIG. 1C shows receiver operator characteristic (ROC) curves, area under and ROC curve (AUC) and its 95% confidence interval (CI) (in parentheses), where the binary outcome was defined as with (other inflammatory neurological disorders (OIND) and all MS groups) versus without intrathecal inflammation (HD and non-inflammatory neurological disorders (NIND)). Comparative data on traditional, currently available laboratory tests of intrathecal inflammation obtained from the same patients are shown in FIG. 5.

In FIG. 2B, grey brackets represent statistically significant differences (p<0.01) that were reproduced in only one of the cohorts (see FIG. 7), whereas black brackets represent those differences that reached statistical significance (p<0.05) in both cohorts, based on pair-wise multiple comparisons with Tukey's correction method. Dotted lines represent the upper limit of normal values (calculated as mean+2 SD from HD), while thick black bars represent the median for each diagnostic category. FIG. 2C shows ROC curves, AUC and its 95% CI (in parentheses), where the binary outcome was defined as with (OIND and all MS groups) versus without intrathecal inflammation (HD and NIND). Comparative data on traditional, currently available laboratory tests of intrathecal inflammation obtained from the same patients are shown in FIG. 5.

FIGS. 3A-3D are a series of graphs showing a combination of biologically-related biomarkers. Three combinatorial biomarkers using Cohort B patients (the only cohort with available CSF immunophenotyping data) were calculated as a ratio between the measured concentration of cell-specific soluble CSF biomarkers and absolute numbers of corresponding CSF cells/ml (sCD14/monocytes, sCD21/B cells, CD27/CD4+CD8 T cells). In FIG. 3A, dotted lines represent the upper limit of normal values, calculated as mean+2 SD of HD cohort, while thick black bars represent the median for each diagnostic category. Black brackets highlight statistically significant differences (p<0.01) between diagnostic categories (primary progressive MS (PPMS), secondary progressive MS (SPMS), RRMS, HD, NIND, and OIND), based on pair-wise multiple comparisons with Tukey's correction. FIG. 3B shows ROC curves, AUCs and their 95% CIs (in parentheses), where the binary outcome was defined as patients with progressive MS (who have elevated ratios and therefore likely more immobile cells in CNS tissue) versus patients with RRMS and OIND (who have more mobile immune cells detectable in the CSF). In FIG. 3C and FIG. 3D, the diagnostic categories consisted of three categories: cyclic meningitis (patients with cyclic aseptic meningitis without accumulation of neurological disability), cryptococcal meningo-encephalitis (patients with both CSF pleiocytosis and accumulation of neurological disability), and progressive MS (patients with PPMS and SPMS). Thick bars represent cohort medians and dotted lines represent upper limit of normal values (calculated as mean+2SD from HD). Black brackets highlight statistically significant differences (p<0.05) between the three diagnostic categories, based on pair-wise multiple comparisons with Tukey's correction. FIG. 3C shows the results from measured concentration of cell-specific soluble CSF biomarkers sCD14, sCD21 and sCD27. FIG. 3D shows the results from sCD14/Monocyte, sCD21/B cell and sCD27/T cell.

FIG. 5B depicts ROC curves, AUC and its 95% CI (in parentheses), based on binary outcome: with (OIND and all MS groups) versus without (HD and NIND) intrathecal inflammation.

FIGS. 7A-7B are a series of graphs showing concentrations of cell surface markers in Cohort A and B. Candidate biomarkers (sCD14, sCD163, sCD21, sCD23 and sCD27) from the shed surface markers category were quantified using newly developed electrochemiluminescence sandwich immunoassays in coded CSF samples of cohorts A (N=193, FIG. 7A) and B (N=193, FIG. 7B). Black brackets highlight those differences that reached statistical significance (p<0.05), based on pair-wise multiple comparisons with Tukey's correction method. Dotted lines represent the upper limit of normal values (mean+2 SD) of HD values. Thick black bars represent the median for each diagnostic category.

(FIG. 9A) Meninges stained with anti-CD68 antibody showing accumulation of macrophages. (FIG. 9B) Meninges stained with anti-CD3 antibody demonstrating a relative paucity of T cells. (FIG. 9C) Brain tissue stained with anti-CD68 antibody showing accumulation of macrophages (brown) around a vessel. (FIG. 9D) Adjacent brain tissue stained with anti-CD3 antibody demonstrating a relative paucity of T cells.

FIGS. 10A-10B are a table of demographic information of study subjects. Statistically significant differences (p<0.01) in demographic and clinical parameters are noted in the superscripts (a, b, c) based on pair-wise multiple comparisons with Tukey's correction method. For oligoclonal bands, Fisher's exact test and pair-wise multiple comparisons with Bonferroni correction was used to evaluate the association between diagnoses. Values shown are the median and range (in parentheses). Age normalized AlbQ was calculated with the following formula: (measured AlbQ)/(age normal AlbQ). Age normal AlbQ was calculated with the following formula: $(4+ age/15) \times 10^{-3}$ (Reiber et al., *Fluids Barriers CNS* 9:17, 2012). *=positive oligoclonal bands results but same number of bands between serum and CSF.

FIGS. 15A-15C are is a set of graphs showing CSF levels of biomarkers that differentiate healthy donors from all neurological diseases.

(FIG. 18A) Area under the receiver operation characteristic (ROC) curves (AUC) with the binary outcome of diagnostic classification of subjects as MS (RRMS, PPMS, SPMS) or non-MS (HD, NIND, OIND) using the combination of all 1128 SOMAmers (solid line), the combination of 459 SOMAmers with SNR>3 (dashed line), and the combination of 459 SOMAmers and 9 SOMAmer ratios (dotted line) in the independent validation cohort. (FIG. 18B) Graphical representation of random forest classifiers sorted based on their importance (y-axis) and mean decrease in accuracy (x-axis) to correctly classify subjects as MS and non-MS. The red line represents a cut-off selecting the 18 most important variables. (FIG. 18C) Correlation matrix of the 18 most important variables derived from Pearson correlation coefficients. Positive and negative correlations are depicted in different shades. Absolute values of correlation coefficients were considered for clustering. The height of columns above the correlation matrix represents the variable importance in the random forest classifier. (FIG. 18D) Ingenuity pathway analysis shows selected SOMAmers that were used in the random forest classifier and their involvement in various functions/diseases.

(FIG. 19A) Area under the ROC curves (AUC) with the binary outcome of diagnostic classification of subjects as progressive MS (PPMS, SPMS) or RRMS using the combination of all 1128 SOMAmers (solid line), the combination of 459 SOMAmers with SNR>3 (dashed line), and the combination of 459 SOMAmers and 9 SOMAmer ratios (dotted line) in the independent validation cohort. (FIG. 19B) Graphical representation of random forest classifiers sorted based on their importance (y-axis) and mean decrease in accuracy (x-axis) to correctly classify subjects as progressive MS and RRMS. The vertical line represents a cut-off selecting the 25 most important variables. (FIG. 19C) Correlation matrix of the 25 most important variables derived from Pearson correlation coefficients. Positive and negative correlations are depicted in different shades. Absolute values of correlation coefficients were considered for clustering. The height of columns above the correlation matrix represents the variable importance in the random forest classifier. (FIG. 19D) Ingenuity pathway analysis shows selected SOMAmers that were used in the random forest classifier and their involvement in various functions/diseases.

FIG. 20 is a table of demographic data.

FIG. 21 is a table of methodological details of biomarker measurements by ELISA.

FIGS. 22A-22B are a pair of tables showing random forest classifiers for molecular diagnosis of MS versus non-MS (FIG. 22A) and progressive MS versus RRMS (FIG. 22B). *permutation based p-values (using 10,000 permutations of original data) were constructed for testing H_0: AUC=0.5 against the upper one-sided alternative. These were corrected for multiple comparisons using the Benjamini and Hochberg False Discovery Rate correction.

DETAILED DESCRIPTION

I. Abbreviations

Figures 1A, 1B, 1C:
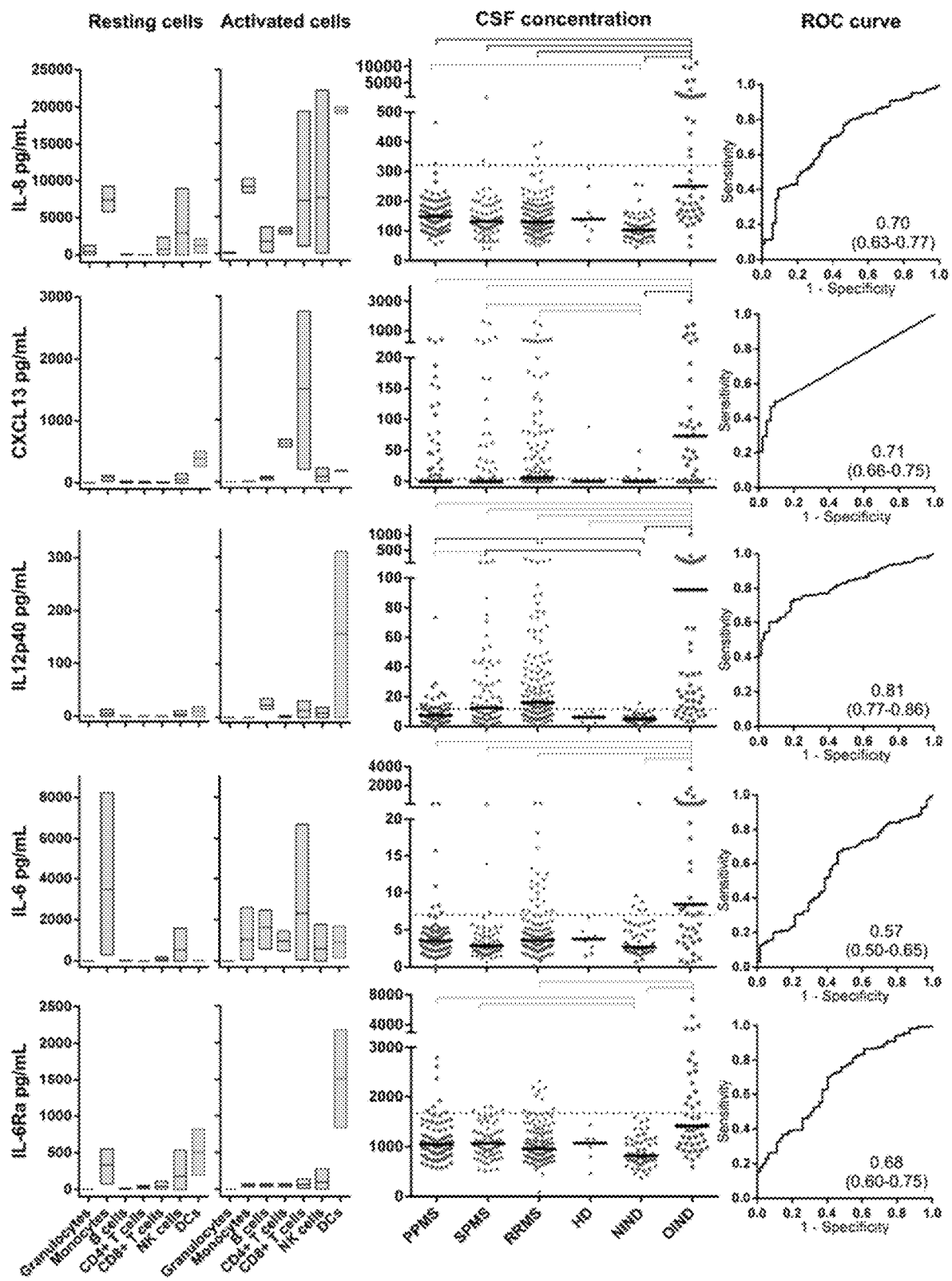
FIGS. 1A-1C are a series of graphs demonstrating that IL-12p40 and IL-8 are biomarkers of intrathecal inflammation. Candidate biomarkers (IL-8, CXCL13, IL-12p40, IL-6 and IL-6Ra) from the cytokine/chemokine category were quantified using commercially-available or newly developed electrochemiluminescence sandwich immunoassays in cultured supernatants from purified, negatively-selected immune subtypes (FIG. 1A) or coded CSF samples from combined cohorts A and B (N=386, FIG. 1B). Purified granulocytes, monocytes, B cells, CD4+ and CD8+ T cells, natural killer (NK) cells and dendritic cells (DCs) ($1 \times 10^6$/ml) from healthy donors (N=3) were either left untreated (FIG. 1A, left) or polyclonally stimulated with PMA/ionomycin (FIG. 1A, right) for 48 hours before collection of supernatants. Biomarker concentrations were re-calculated per million cells of each specific subtype using flow cytometry data for purity of each seeded culture.

AlbQ albumin quotient
ANOVA one-way analysis of variance
AUC area under the ROC curve
BSA bovine serum albumin
CEL contrast-enhancing lesion
CI confidence intervals
CNS central nervous system
CSF cerebral spinal fluid
DC dendritic cell
ELISA enzyme-linked immunosorbent assay
HD healthy donor
HRP horseradish peroxidase
IL interleukin
IQR interquartile range
MRI magnetic resonance imaging
MS multiple sclerosis
MSD MESO SCALE DISCOVERY™
NK natural killer
NIND non-inflammatory neurological disease
OCB oligoclonal bands
OIND other inflammatory neurological disease
PBS phosphate buffered saline
PMA phorbol myristate acetate
PPMS primary progressive multiple sclerosis
Q3 third quartile
ROC receiver operation characteristic
RRMS relapsing remitting multiple sclerosis
SD standard deviation
SPMS secondary progressive multiple sclerosis
WBC white blood cell
WML white matter lesion II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administer: As used herein, administering a composition (e.g. an antibody, such as rituximab) to a subject means to give, apply or bring the composition into contact with the subject. Administration can be accomplished by any of a number of routes, such as, for example, intravenous, intrathecal, topical, oral, intranasal, subcutaneous, intramuscular and intraperitoneal.

Antibody: Immunoglobulin molecules and immunologically active portions of immunoglobulin molecules, e.g., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an Fd fragment consisting of the $V_H$ and $C_{H1}$ domains; (iii) an Fv fragment consisting of the $V_L$ and $V_H$ domains of a single arm of an antibody, (iv) a dAb fragment (Ward et al., *Nature* 341:544-546, 1989) which consists of a $V_H$ domain; (v) an isolated complementarity determining region (CDR); and (vi) a F(ab')2 fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055 and 4,444,487; WO 88/03565; EP 256,654; EP 120,694; EP 125,023; Falkner et al., *Nature* 298:286, 1982; Morrison, *J. Immunol.* 123:793, 1979; Morrison et al., *Ann. Rev. Immunol.* 2:239, 1984).

Aptamer: A small nucleic acid that specifically binds a target molecule, such as a protein. In some instances, the aptamer is chemically modified or labelled.

Array: An arrangement of molecules, such as biological macromolecules (such as peptides, antibodies or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an aptamer or antibody) will occur on the array a plurality of times (such as twice), for instance to provide internal controls. The number of addressable locations on the array can vary, for example from at least two, at least three, at least four, to at least 9, at least 10, at least 14, at least 15, at least 20, at least 30, at least 50, at least 75, at least 100, at least 150, at least 200, at least 300, at least 500, least 550, at least 600, at least 800, at least 1000, at least 10,000, or more. In a particular example, an array includes 5-100 addressable locations, such as 5-50, including 5-15, addressable locations. In particular examples, an array consists essentially of nucleic acids or antibodies specific for at least one, at least two, at least three, at least four, at least five, at least six, at least seven, at least eight, at least nine, at least 10, at least 15, at least 20, at least 25, at least 30, at least 35, at least 40, at least 45 or at least 50 biomarkers disclosed herein, and in some examples, also 1 to 10, such as up to five, control molecules (such as housekeeping genes/proteins).

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies or aptamers to at least two, at least three, at least four, at least five, at least 10, at least 15, at least 20, at least 25, at least 30, at least 35, at least 40, at least 45 or at least 50 biomarkers disclosed herein, and in some examples also 1 to 10 housekeeping genes/proteins.

B cell depleting agent: Any compound, such as a monoclonal antibody, that promotes a reduction in the number of B cells in a subject or in particular anatomical region of a subject (such as in the intrathecal compartment). "Depletion" of B cells need not be complete depletion, but encompasses any significant reduction in the number of B cells, such as a reduction of at least 10%, at least 20%, at least 30%, at least 40%, at least 50%, at least 60%, at least 70% or at least 80%. Thus, in some examples herein, a B cell depleting agent reduces the total number of B cells in a subject, such as within the intrathecal compartment of the subject. B cell depleting agents include, for example, monoclonal antibodies that target B cell surface antigens, such as but not limited to CD19, CD20 and CD22.

Biomarker: In the context of the present disclosure, a "biomarker" is a protein (or protein ratio) indicative of the presence of a particular disease state, such as an inflammatory neurological disease. In some embodiments, the "biomarker" is the ratio of the level of a first protein to the level of a second protein. In yet other embodiments, the "biomarker" is the ratio between the level of a particular protein in the CSF and absolute number of corresponding CSF cells/ml of CSF. In most instances throughout the present disclosure, the biomarker is indicated by the gene (for example, the gene symbol; see Tables 3A-3H, 4, 5 and 6A-6B and FIGS. 16 and 22A-22B) that encodes the protein biomarker.

Control: A "control" refers to a sample or standard used for comparison with an experimental sample, such as a sample (e.g. a CSF sample) obtained from a patient with a neurological disorder to be tested for protein biomarker levels (such as IL-12p40, sCD27, sCD14 or sCD21). In some embodiments, the control is a sample obtained from a healthy patient. In other embodiments, the control is a historical control or reference standard (i.e. a previously tested control sample or group of samples that represent baseline or normal values, such as the average level of a particular biomarker in the CSF of healthy subjects, or subjects with a non-inflammatory neurological disorder). In other embodiments, the control is an average value obtained from subjects diagnosed with an inflammatory neurological disorder other than MS; an average value obtained from subjects diagnosed with RRMS; or an average value obtained from subjects diagnosed with MS. In yet other embodiments herein, the "control" is a patient that has been administered a placebo or a healthy control subject (i.e. a subject that does not have MS or another neurological disorder).

CD14: A protein expressed by monocytes and activated microglia. CD14 is the primary receptor for lipopolysaccharide and a co-receptor for various toll-like receptors. Soluble CD14 (sCD14) is the cell-free form of CD14 lacking a transmembrane domain. See NCBI Gene ID 929 for human CD14.

CD19: A protein expressed on the surface of follicular dendritic cells and B cells. In B cells, CD19 is expressed at the earliest stages of B cell development and on mature B cells. CD19 is found on both normal and transformed B cells.

CD19 monoclonal antibodies: Any monoclonal antibody, including human, mouse, chimeric or engineered antibodies, that specifically binds CD19. Exemplary anti-CD19 antibodies include BU-12 (Flavell et al., *Br J Cancer* 72(6): 1373-1379, 1995) and huB4 (a humanized mouse monoclonal antibody, used in the SAR3419 immunoconjugate; Al-Katib et al., *Clin Cancer Res* 15(12):4038-4045, 2009).

CD20: The CD20 protein (cluster of differentiation 20, also called human B-lymphocyte-restricted differentiation antigen or Bp35) is a hydrophobic transmembrane protein with a molecular weight of approximately 35 kD located on pre-B and mature B lymphocytes (Valentine et al., *J. Biol. Chem.* 264(19):11282-11287, 1989; and Einfield et al., *EMBO J.* 7(3):711-717, 1988). In vivo, CD20 is found on the surface of greater than 90% of B cells from peripheral blood or lymphoid organs and is expressed during early pre-B cell development and remains expressed until plasma cell differentiation. CD20 is present on both normal B cells and malignant B cells, but is not found on hematopoietic stem cells, pro-B cells, normal plasma cells, or other normal tissues (Tedder et al., *J. Immunol.* 135(2):973-979, 1985). CD20 is involved in regulating early steps in the activation and differentiation process of B cells (Tedder et al., *Eur. J. Immunol.* 16:881-887, 1986) and can function as a calcium ion channel (Tedder et al., *J. Cell. Biochem.* 14D:195, 1990). The antibody rituximab specifically binds CD20.

CD20 monoclonal antibodies: Any monoclonal antibody, including human, mouse, chimeric or engineered antibodies, that specifically binds CD20. Exemplary anti-CD20 antibodies that have been evaluated in clinical studies, and in some cases approved for human use, include Ofatumumab (a human antibody; also known as ARZERRA™ and HuMax-CD20), ocrelizumab (a humanized antibody), veltuzumab (a humanized antibody), obinutuzumab (a humanized antibody; also known as GA101), AME-133v (an Fc-engineered humanized mAb), PRO131921 (a humanized antibody; also known as version 114 or v114) and LFB-R603/EMAB-6 (a chimeric mouse/human antibody). Anti-CD20 monoclonal antibodies that have been approved for clinical use in the United States, or are currently in clinical trials, are reviewed in Oflazoglu and Audoly, mAbs 2(1): 14-19, 2010.

CD21: A protein expressed by mature B cells, follicular DCs and T cells. B cell receptor activation induces shedding of CD21. Soluble CD21 (sCD21) is a selective biomarker of B cells released in resting and activated states. sCD21 activates monocytes through binding to membrane CD23 and leads to degranulation of basophils upon cross-linking. CD21 is also known as CR2, CR, C3DR, CVID7 and SLEB9. See NCBI Gene ID 1380 for human CD21.

CD22: A protein found on the surface of mature B cells and some immature B cells. CD22 is a member of the immunoglobulin superfamily.

CD22 monoclonal antibodies: Any monoclonal antibody, including human, mouse, chimeric or engineered antibodies, that specifically binds CD22. An exemplary anti-CD22 antibody that has been evaluated in clinical studies is Epratuzumab, a humanized antibody (also known as LYMPHOCIDE™).

CD27: A protein expressed by a variety of cell types, including T cells, NK cells, memory B cells and plasmablasts. CD27 is a member of the TNF-receptor superfamily. The ligand for CD27 is CD70, which is expressed on mature DCs, NK cells, and T and B lymphocytes. CD27/CD70 signaling provides a survival signal for activated T cells and drives Th1 cell differentiation. In addition, CD8+ T cells require CD27 for optimal secondary expansion. Although expressed by several cell types, soluble CD27 (sCD27) is secreted in large quantities only by activated T cells. CD27 is also known as T14; S152; Tp55; TNFRSF7; S152 and LPFS2. See NCBI Gene ID 939 for human CD27.

Cerebral spinal fluid (CSF): A clear, colorless bodily fluid that occupies the subarachnoid space and the ventricular system around and inside the brain and spinal cord.

Consists essentially of: In the context of the arrays disclosed herein, "consists essentially of" indicates that the expression of additional biomarkers can be evaluated, but not more than ten additional biomarkers. In some examples, "consist essentially of" indicates that no more than 5 other biomarkers are evaluated, such as no more than 4, 3, 2, or 1 other biomarkers. In some examples, fewer than the recited biomarkers are evaluated, but not less than 5, 4, 3, 2 or 1 fewer biomarkers. In some examples, the expression of one or more controls is evaluated, such as a housekeeping protein. In this context "consist of" indicates that only the expression of the stated molecules are evaluated; the expression of additional molecules is not evaluated.

CXCL13 (chemokine (C—X—C motif) ligand 13): A CXC chemokine expressed in follicular DCs, monocytes, macrophages, B cells and T cells. CXCR13 preferentially promotes the migration of B lymphocytes. This chemokine recruits both B cells and T follicular helper cells by signaling through its cognate receptor CXCR5. CXCL13 is also known as BLC; BCA1; ANGIE; BCA-1; BLR1L; ANGIE2; and SCYB13. See NCBI Gene ID 10563 for human CXCL13.

Detecting expression of a gene: Determining the existence, in either a qualitative or quantitative manner, of a particular nucleic acid or protein product (such as IL-12p40, sCD27, sCD14 or sCD21). Exemplary methods of detecting the level of protein expression include immunoassays, such as Western blot, immunohistochemistry and ELISA, aptamer arrays and mass spectrometry. Exemplary methods of detecting the level of nucleic acid (such as mRNA) include RT-PCR, Northern blot and in situ hybridization.

Immunomodulatory therapy: Any treatment regimen that alters an immune response, such as by increasing or decreasing the number or activity of cells of the immune system (including the innate or adaptive immune systems). Immunomodulatory therapies include, for example, agents that deplete cells of the immune system, such as T cell depleting agents or B cell depleting agents.

Interleukin-8 (IL-8): A CXC motif chemokine expressed by monocytes, microglia, lymphocytes, granulocytes, fibroblasts, endothelial cells, astrocytes and epithelial cells. IL-8 binds receptors CXCR1 and CXCR2. This cytokine induces chemotaxis and phagocytosis in primary neutrophils and granulocytes, endothelial cells, macrophages, mast cells and keratinocytes. IL-8 is also known as CXCL8, NAF, GCP1, LECT, LUCT, NAP1, GCP-1, LYNAP, MDNCF, MONAP and NAP-1. See NCBI Gene ID 3576 for human IL-8.

Interleukin-12 p40 subunit (IL-12p40): A cytokine that acts on T cells and natural killer cells, and has a broad array of biological activities. IL-12p40 is expressed by monocytes, macrophages, microglia and myeloid DCs. IL-12 is a disulfide-linked heterodimer composed of the 40 kD cytokine receptor like subunit (IL-12p40) encoded by the IL12B gene, and a 35 kD subunit encoded by IL12A. IL-12p40 is also one of the subunits of cytokine IL-23 (together with IL-23p19 subunit). IL-12 is expressed by activated macrophages that serve as an essential inducer of Th1 cell development, while IL-23, expressed by activated macrophages and dendritic cells is essential inducer of Th17 cells. IL-12 has been found to be important for sustaining a sufficient number of memory/effector Th1 cells to mediate long-term protection to an intracellular pathogen. IL-12p40 is also known as interleukin 12B (natural killer cell stimulatory factor 2, cytotoxic lymphocyte maturation factor 2, p40), IL12B, CLMF, NKSF, CLMF2 and NKSF2. See NCBI Gene ID 3593 for human IL-12p40.

Intrathecal administration: Administration into the subarachnoid space under the arachnoid membrane of the brain or spinal cord through which the cerebral spinal fluid flows. For example, intrathecal delivery can be accomplished by delivery through a needle into the subarachnoid space of the spinal cord or brain (such as by lumbar puncture), or intraventricularly into the CSF in one of the ventricles of the brain for subsequent flow through the subarachnoid space of the brain or spinal cord.

Intrathecal inflammation: Inflammation occurring within or lining the intrathecal compartment. This would include aggregation of immune cells in the meninges or infiltration of immune cells anywhere in the brain and spinal cord tissue in numbers that exceeds physiological levels observed in healthy subjects.

Label: A detectable compound or composition that is conjugated directly or indirectly to another molecule, such as an antibody, protein or nucleic acid molecule (for example, an aptamer) to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, C, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Measuring or measuring the level of: As used herein, "measuring" or "measuring the level of" a particular protein (such as IL-12p40, IL-8, sCD27, sCD14 or sCD21) refers to quantifying the amount of the protein present in a sample (such as a CSF sample). Quantification can be either numerical or relative. Detecting expression of the protein can be achieved using any method known in the art or described herein, such as by ELISA or aptamer array.

Meningeal inflammation: Inflammation of the meninges, the membranes that cover the brain and spinal cord.

Multiple sclerosis: An immune-mediated disease classically described as a central nervous system white matter disorder disseminated in time and space that presents as relapsing-remitting illness in 80-85% of patients. Diagnosis can be made by brain and spinal cord magnetic resonance imaging (MRI), analysis of somatosensory evoked potentials, and analysis of cerebrospinal fluid to detect increased amounts of immunoglobulin or oligoclonal bands. MRI is a particularly sensitive diagnostic tool; however it is not specific. In other words, MRI abnormalities that are typical of MS can be also seen with other inflammatory or noninflammatory neurological diseases. MRI abnormalities indicating the presence or progression of MS include hyperintense white matter signals on T2-weighted and fluid attenuated inversion recovery images, gadolinium enhancement of active lesions, hypointensive "black holes" (representing gliosis and axonal pathology), and brain atrophy on T1-weighted studies. Serial MRI studies can be used to indicate disease progression. Relapsing-remitting multiple sclerosis (RRMS) is a clinical course of MS that is characterized by clearly defined, acute attacks with full or partial recovery and no disease progression between attacks. Secondary-progressive multiple sclerosis (SPMS) is a clinical course of MS that initially is relapsing-remitting, and then becomes progressive at a variable rate, possibly with an occasional relapse and minor remission. Primary progressive multiple sclerosis (PPMS) presents initially in the progressive form.

Neurological disease: Any disease or disorder of the nervous system. An "inflammatory neurological disease" refers to any neurological disease associated with an inflammatory response or inflammation.

Non-inflammatory neurological disease (NIND): Neurological diseases that do not have an inflammatory component. Exemplary NINDs include, but are not limited to, epilepsy, amyotrophic lateral sclerosis, compressive myelopathy, Lyme disease without CNS involvement, leukodystrophy, mitochondrial disease, hydromyelia and headache.

Other inflammatory neurological disease (OIND): In the context of the present disclosure, "OIND" and "inflammatory neurological disease other than MS" encompass any inflammatory neurological disease except multiple sclerosis. Diseases classified as OIND include, but are not limited to, cryptococcal meningo-encephalitis, CNS paraneoplastic syndrome, cyclic meningitis, Aicardi-Goutieres syndrome with CNS involvement, Susac's syndrome, neonatal onset multisystem inflammatory disease with CNS involvement, Lyme disease with CNS involvement, HTLV-1 associated myelopathy, sarcoidosis with CNS involvement, lupus erythematosus with CNS involvement, CNS vasculitis, autoimmune lymphoproliferative syndrome with CNS involvement and encephalitis/ventriculitis with unknown origin.

Pharmaceutical agent or drug: A chemical compound or composition capable of inducing a desired therapeutic or prophylactic effect when properly administered to a subject.

Pharmaceutically acceptable carriers: The pharmaceutically acceptable carriers useful in the methods disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of antibodies, such as rituximab.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

In some embodiments, the pharmaceutically acceptable carrier includes or consists essentially of a non-naturally occurring pharmaceutical carrier, or contains a non-natural preservative and/or auxiliary substance(s).

Rituximab: A chimeric monoclonal antibody that specifically binds CD20, which is primarily found on the surface of B cells. Rituximab is used in the treatment of lymphoma, leukemia, transplant rejection and autoimmune disorders, including multiple sclerosis. Rituximab is sold under the trade names RITUXAN™ and MABTHERA™. Rituximab is a genetically engineered monoclonal antibody with murine light and heavy chain variable regions, and human gamma 1 heavy chain and kappa light chain constant regions. The chimeric antibody is composed of two heavy chains of 451 amino acids and two light chains of 213 amino acids and has an approximate molecular weight of 145 kD. Rituximab was genetically engineered using the murine 2B8 antibody and is described in, for example, U.S. Pat. Nos. 6,455,043; 5,736,137; 5,843,439; and 5,776,456, each of which is herein incorporated by reference. The 2B8 hybridoma is deposited with the ATCC under deposit number HB-11388.

Sample or biological sample: As used herein, a "sample" obtained from a subject refers to a cell, fluid or tissue sample. Bodily fluids include, but are not limited to, cerebral spinal fluid, tears, blood, serum, urine and saliva. In the context of the present disclosure "obtaining a biological sample" includes either directly collecting the sample from the subject, or obtaining the sample from a laboratory or service provider that has collected the sample from the subject. A sample "obtained from a subject" is a sample acquired by similar means.

Subject: A human or non-human animal. In one embodiment, the subject has multiple sclerosis.

Symptom and sign: Any subjective evidence of disease or of a subject's condition, i.e., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for immunological status or the presence of lesions in a subject with multiple sclerosis.

T cell depleting agent: Any compound, such as a monoclonal antibody, that promotes a reduction in the number of T cells in a subject or in the particular anatomical region of a subject (such as in the intrathecal compartment). "Depletion" of T cells need not be complete depletion, but encompasses any significant reduction in the number of T cells, such as a reduction of at least 10%, at least 20%, at least 30%, at least 40%, at least 50%, at least 60%, at least 70% or at least 80%. Thus, in some examples herein, a T cell depleting agent reduces the total number of T cells in a subject, such as within the intrathecal compartment of the subject. T cell depleting agents include, for example, monoclonal antibodies that target T cell surface antigens, such as, but not limited to, CD3, CD4 and CD8, as well as anti-thymocyte globulin.

Therapeutically effective amount: A dose sufficient to prevent advancement, or to cause regression of the disease, or which is capable of reducing symptoms caused by the disease, such as multiple sclerosis.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Introduction

Therapeutic progress for CNS diseases has been slow (Kola and Landis, *Nat Rev Drug Discov* 3(8):711-715, 2004) when compared to systemic diseases with equally multifaceted pathophysiology, such as cardiovascular disorders and cancer. Conversely, treatment of cardiovascular diseases and current advances in the molecular taxonomy of cancer have convincingly demonstrated that the development of effective, personalized combination therapies is possible by using biomarkers (Schadt et al., *Front Pharmacol* 5:252, 2014; Morgan et al., *Drug Discov Today* 17(9-10):419-424, 2012). Biomarkers, defined broadly as measurements of analytes, processes or functions other than disability, have shown that multiple pathogenic mechanisms cause cardiovascular events. Biomarkers have also demonstrated that a single therapeutic rarely targets more than one process and that optimal management of complex diseases requires polypharmacy that minimizes all contributing mechanisms present in individual patient(s). Polypharmacy, or at a minimum, rational drug- or dose-adjustments are required even when a single pathogenic driver of the disease is identified, because successful treatment necessitates its complete elimination. Such personalized therapeutic decisions are possible only through biomarkers.

Considering the wealth of knowledge about the multiplicity of mechanisms that drive disability in neurodegenerative diseases, it is unlikely that a single agent will have a complete therapeutic effect on any CNS disorder, unless applied in the early (pre-clinical) stage. Once disease has evolved and tissue destruction has reached the threshold beyond which functional compensation is not possible, partial benefit of a single drug may be difficult to discern in Phase II trials. This conundrum of the inability to identify pre-clinical stage of the disease(s), when drug efficacy may be high, versus difficulty to measure comparably small efficacy once the disease(s) evolve, underlies the lack of therapeutic progress. The observations that neurological diseases with frequent and easily quantifiable features (such as headaches, seizures or contrast-enhancing lesions (CELs) on MRI imaging in relapsing-remitting MS) experienced major therapeutic advancements argue against the lack of therapeutic candidates being the bottleneck, but rather the inability to screen them in a reliable but economical manner.

Biomarkers represent an essential solution to this problem. While a decade ago, oncology had lower drug attrition rates then neurology (Kola and Landis, *Nat Rev Drug Discov* 3(8):711-715, 2004), the switch from clinical/phenotypic to molecular taxonomy of cancers revolutionized both drug development and oncology practice. Identification of mutations underlying human cancers focused drug development away from poorly-predictive animal models to human pathophysiologically-relevant dysregulated pathways and provided tools to screen drug's efficacy in economical proof-of-concept (POC) trials. Prescreening of patients for the presence of the therapeutic target and validation of in vivo target modulation via pharmacodynamic (PD) biomarkers (Morgan et al., *Drug Discov Today* 17(9-10):419-424, 2012), significantly improved drug attrition in contemporary oncology POC trials. Additionally, these advances aided implementation of novel features into the clinical trial methodology, such as biomarker-guided adaptive randomization and simultaneous screening of multiple therapies and their combinations (Berry, *Mol Oncol* 9(5):951-959, 2015).

Analogously, it is believed that the ability to quantify pathological processes in the CNS of living subjects is a prerequisite to broad therapeutic progress in neurology. As dynamic outflow for CNS interstitial fluid (Johanson et al., *Cerebrospinal Fluid Res* 5:10, 2008), cerebrospinal fluid (CSF) is an ideal source of molecular biomarkers (Komori et al., *Ann Neurol* 78(1):3-20, 2015). Although a limited number of CSF biomarkers were found to be differentially expressed in many neurological diseases (Bielekova and Martin, *Brain* 127(Pt 7):1463-1478, 2004; Tumani et al., *Expert Rev Mol Diagn* 8(4):479-494, 2008), only a few reached clinical practice and virtually none guided new drug development. Invasiveness of CSF collection is a limitation; but this can be overcome when informational benefit outweighs the perceived inconvenience, as proven by colonoscopy. It is envisioned that if CSF biomarkers could be assembled into disease-specific diagnostic tests and used to guide selection of individualized treatments, lumbar punctures would become a routine procedure. The CSF biomarkers disclosed herein can also be used to direct treatment decisions, such as to make adjustments on the dose of a therapeutic agent or the selection of a particular therapeutic treatment.

IV. Overview of Several Embodiments

The management of neuroimmunological diseases is severely hindered by an inability to reliably measure intrathecal inflammation. Current laboratory tests do not capture low to moderate levels of CNS inflammation and provide limited information about its phenotype. Disclosed herein are biomarkers of CNS inflammation. The biomarkers disclosed herein are capable of distinguishing subjects with MS from subjects that do not have MS, distinguishing progressive MS from RRMS, identifying patients with intrathecal inflammation, distinguishing MS patients from patients with other types of inflammatory neurological diseases, identifying subjects with non-MS inflammatory neurological diseases, differentiating healthy subjects from patients with any type of neurological disease, and/or identifying subjects with increased disability, CNS tissue damage and/or neurodegeneration. Also disclosed are process-specific biomarkers that can be used in place of a brain biopsy to identify immune cell infiltration and/or activation in the CNS.

In the methods disclosed in the present application, the step of identifying the subject as having a particular disease phenotype (such as intrathecal inflammation) can be obtained by a testing facility, such as a lab or other third party.

A. Differentiating MS from Non-MS

Provided herein is a method of identifying a subject as having MS, or susceptible to developing MS, by measuring and detecting an increase or decrease in one or more biomarkers capable of distinguishing subjects with MS (PPMS, SPMS and RRMS) from subjects that do not have MS (HD, OIND and NIND). In some embodiments, the method includes (1) measuring at least one biomarker in a CSF sample obtained from the subject, wherein the at least one biomarker is selected from the ratio of FLT4 to TNFRSF17; the ratio of TNFRSF17 to CD48; the ratio of TNFRSF17 to IL16; the ratio of TNFRSF17 to TNFRSF6B; the ratio of TNFRSF17 to CD163; the ratio of TNFRSF17 to SHC1; TNFRSF17; the ratio of TNFRSF17 to UFC1; the ratio of LY9 to IGHG1; the ratio of LTA LTB to IGHG1; MMP7; SLAMF7; TNFRSF1B; IGHG1; CD48; VCAM1; CHIT1; and PLA2G5; (2) identifying the subject as having MS, or susceptible to developing MS, if there is an increase in at least one of TNFRSF17; MMP7; SLAMF7; TNFRSF1B; CD48; VCAM1; CHIT1; PLA2G5; IGHG1; the ratio of TNFRSF17 to CD48; the ratio of TNFRSF17 to IL16; the ratio of TNFRSF17 to TNFRSF6B; the ratio of TNFRSF17 to CD163; the ratio of TNFRSF17 to SHC1; and the ratio of TNFRSF17 to UFC1; and/or a decrease in at least one of the ratio of FLT4 to TNFRSF17; the ratio of LY9 to IGHG1; and the ratio of LTA LTB to IGHG1, compared to a control. In some examples, the method includes measuring at least 2, at least 3, at least 4, at least 5, at least 6, at least 7, at least 8, at least 9, at least 10 or all of the above-listed biomarkers in a CSF sample obtained from the subject.

In particular embodiments, the at least one biomarker includes the ratio of FLT4 to TNFRSF17; the ratio of TNFRSF17 to CD48; the ratio of TNFRSF17 to TNFRSF6B; the ratio of TNFRSF17 to IL16; the ratio of TNFRSF17 to CD163; the ratio of TNFRSF17 to SHC1; the ratio of TNFRSF17 to UFC1; TNFRSF17; the ratio of LY9 to IGHG1; the ratio of LTA LTB to IGHG1; the ratio of LTA LTB to IGHG1; MMP7; SLAMF7; TNFRSF1B; IGHG1; CD48; VCAM1; CHIT1; and PLA2G5.

In some examples, the at least one biomarker includes the ratio of TNFRSF17 to a second protein. In particular examples, the at least one biomarker includes the ratio of FLT4 to TNFRSF17 to and up to 10, up to 20, up to 30, up to 40 or up to 50 additional biomarkers. In other particular examples, the at least one biomarker includes the ratio of TNFRSF17 to CD48 and up to 10, up to 20, up to 30, up to 40 or up to 50 additional biomarkers. In other particular examples, the at least one biomarker includes the ratio of TNFRSF17 to TNFRSF6B and up to 10, up to 20, up to 30, up to 40 or up to 50 additional biomarkers. In other particular examples, the at least one biomarker includes the ratio of TNFRSF17 to IL16 and up to 10, up to 20, up to 30, up to 40 or up to 50 additional biomarkers. In other particular examples, the at least one biomarker includes the ratio of TNFRSF17 to CD163 and up to 10, up to 20, up to 30, up to 40 or up to 50 additional biomarkers. In other particular examples, the at least one biomarker includes the ratio of TNFRSF17 to SHC1 and up to 10, up to 20, up to 30, up to 40 or up to 50 additional biomarkers. In other particular examples, the at least one biomarker includes the ratio of TNFRSF17 to UFC1 and up to 10, up to 20, up to 30, up to 40 or up to 50 additional biomarkers. In other particular examples, the at least one biomarker includes TNFRSF17 and up to 10, up to 20, up to 30, up to 40 or up to 50 additional biomarkers.

In some examples, the at least one biomarker includes the ratio of LY9 to IGHG1 and up to 10, up to 20, up to 30, up to 40 or up to 50 additional biomarkers.

In some examples, the at least one biomarker includes the ratio of LTA LTB to IGHG1 and up to 10, up to 20, up to 30, up to 40 or up to 50 additional biomarkers.

In some examples, the at least one biomarker includes MMP7 and up to 10, up to 20, up to 30, up to 40 or up to 50 additional biomarkers.

In some examples, the at least one biomarker includes SLAMF7 and up to 10, up to 20, up to 30, up to 40 or up to 50 additional biomarkers.

In some examples, the at least one biomarker includes TNFRSF1B and up to 10, up to 20, up to 30, up to 40 or up to 50 additional biomarkers.

In some examples, the at least one biomarker includes IGHG1 and up to 10, up to 20, up to 30, up to 40 or up to 50 additional biomarkers.

In some examples, the at least one biomarker includes CD48 and up to 10, up to 20, up to 30, up to 40 or up to 50 additional biomarkers.

In some examples, the at least one biomarker includes VCAM1 and up to 10, up to 20, up to 30, up to 40 or up to 50 additional biomarkers.

In some examples, the at least one biomarker includes CHIT1 and up to 10, up to 20, up to 30, up to 40 or up to 50 additional biomarkers.

In some examples, the at least one biomarker includes PLA2G5 and up to 10, up to 20, up to 30, up to 40 or up to 50 additional biomarkers.

In some embodiments, the control is a reference standard. In other examples, the control is an average value obtained from healthy subjects and/or subjects diagnosed with a non-MS inflammatory disease.

In some embodiments, the method further includes providing an appropriate therapy to the subject that has MS, or is susceptible to developing MS. For example, in some cases the subject with MS is treated with an immunomodulatory therapy, such as a T cell depleting agent and/or a B cell depleting agent.

In some embodiments, the method further includes obtaining a CSF sample from the subject.

In some embodiments, the biomarker is measured using an antibody specific for the biomarker, such as in an immunoassay. In other embodiments, the biomarker is measured using an aptamer that specifically binds the biomarker. In some examples, the antibody or aptamer is chemically modified or is labelled, such as for ease of detection.

Also provided herein is an array for detection and quantitation of biomarkers that identify a subject as having MS or susceptible to developing MS. In some examples, the array comprises binding molecules (such as antibodies or aptamers) that specifically bind at least one of FLT4, TNFRSF17, CD48, IL16, TNFRSF6B, CD163, SHC1, UFC1, LY9, IGHG1, LTA LTB, MMP7, SLAMF7, TNFRSF1B, VCAM1, CHIT1 and PLA2G5. In specific examples, the array consists essentially of antibodies or aptamers that specifically bind at least 2, at least 3, at least 4, at least 5, at least 6, at least 7, at least 8, at least 9, at least 10, or all of FLT4, TNFRSF17, CD48, IL16, TNFRSF6B, CD163, SHC1, UFC1, LY9, IGHG1, LTA LTB, MMP7, SLAMF7, TNFRSF1B, VCAM1, CHIT1 and PLA2G5.

Also provided herein is method of treating MS in a subject. In some embodiments, the method includes (1) selecting a subject having an increase or decrease in at least one biomarker in a CSF sample obtained from the subject relative to a control, wherein the at least one biomarker that is decreased is selected from the ratio of FLT4 to TNFRSF17; the ratio of LY9 to IGHG1; and the ratio of LTA LTB to IGHG1; and/or the at least one biomarker that is increased is selected from TNFRSF17; MMP7; SLAMF7; TNFRSF1B; CD48; VCAM1; CHIT1; PLA2G5; IGHG1; the ratio of TNFRSF17 to CD48; the ratio of TNFRSF17 to IL16; the ratio of TNFRSF17 to TNFRSF6B; the ratio of TNFRSF17 to CD163; the ratio of TNFRSF17 to SHC1; and the ratio of TNFRSF17 to UFC1; and (2) administering to the subject an immunomodulatory therapy. In some examples, the immunomodulatory therapy comprises administration of a T cell depleting agent, administration of a B cell depleting agent, or both. In some examples, the method includes selecting a subject having an increase or decrease in at least 2, at least 3, at least 4, at least 5, at least 6, at least 7, at least 8, at least 9, at least 10 or all of the above-listed biomarkers.

Further provided is a method of evaluating the effectiveness of a therapy for treating MS in a subject. In some embodiments, the method includes measuring at least one biomarker in the CSF of the subject before and after treatment, wherein the at least one biomarker is selected from the ratio of FLT4 to TNFRSF17; the ratio of TNFRSF17 to CD48; the ratio of TNFRSF17 to IL16; the ratio of TNFRSF17 to TNFRSF6B; the ratio of TNFRSF17 to CD163; the ratio of TNFRSF17 to SHC1; TNFRSF17; the ratio of TNFRSF17 to UFC1; the ratio of LY9 to IGHG1; the ratio of LTA LTB to IGHG1; MMP7; SLAMF7; TNFRSF1B; IGHG1; CD48; VCAM1; CHIT1; and PLA2G5, and wherein a decrease in at least one of TNFRSF17; MMP7; SLAMF7; TNFRSF1B; CD48; VCAM1; CHIT1; PLA2G5; IGHG1; the ratio of TNFRSF17 to CD48; the ratio of TNFRSF17 to IL16; the ratio of TNFRSF17 to TNFRSF6B; the ratio of TNFRSF17 to CD163; the ratio of TNFRSF17 to SHC1; and the ratio of TNFRSF17 to UFC1, and/or an increase in at least one of the ratio of FLT4 to TNFRSF17; the ratio of LY9 to IGHG1; and the ratio of LTA LTB to IGHG1 indicates the therapy is effective for the treatment of MS in the subject. In some examples, the type of MS is PPMS, SPMS or RRMS. In some examples, the method includes measuring at least 2, at least 3, at least 4, at least 5, at least 6, at least 7, at least 8, at least 9, at least 10 or all of the above-listed biomarkers in the CSF of the subject before and after treatment. In some examples, the treatment comprises an immunomodulatory therapy, such as administration of a T cell depleting agent, administration of a B cell depleting agent, or both.

B. Differentiating Progressive MS from RRMS

Provided herein are methods of determining whether an MS patient has progressive MS or RRMS by measuring and detecting an increase or decrease in one or more biomarkers capable of distinguishing patients with progressive MS (PPMS or SPMS) from patients with RRMS.

In some embodiments, the method includes (1) measuring at least one biomarker in a CSF sample obtained from the subject, wherein the at least one biomarker is selected from the ratio of JAM3 to EDA2R; the ratio of TYRO3 to EDA2R; the ratio of EDA2R to ROBO2; the ratio of F3 to ROBO2; the ratio of EDA2R to STX1A; the ratio of EDA2R to EPHA5; the ratio of LTA LTB to SERPING1; the ratio of NTRK3 to EDA2R; the ratio of WIF1 to EDA2R; the ratio of EDA2R to ALCAM; the ratio of EDA2R to L1CAM; the ratio of TIE1 to EPHA5; the ratio of EDA2R to EPHB2; the ratio of CFD to F5; the ratio of EDA2R to APP; the ratio of IL13RA1 to LTA LTB; the ratio of EPHA5 to DLL1; the ratio of CADM1 to CDNF; the ratio of CDNF to IL20RA; SHH; the ratio of EDA2R to NRXN3; the ratio of ROBO2 to IL17RC; the ratio of EDA2R to CADM1; the ratio of EDA2R to RTN4R; and LTA LTB; (2) identifying the subject as having progressive MS if there is a decrease in at least one of LTA LTB; the ratio of JAM3 to EDA2R; the ratio of TYRO3 to EDA2R; the ratio of LTA LTB to SERPING1; the ratio of NTRK3 to EDA2R; the ratio of WIF1 to EDA2R; the ratio of EPHA5 to DLL1; the ratio of CADM1 to CDNF; and the ratio of ROBO2 to IL17RC; and/or an increase in at least one of SHH; the ratio of EDA2R to ROBO2; the ratio of F3 to ROBO2; the ratio of EDA2R to STX1A; the ratio of EDA2R to EPHA5; the ratio of EDA2R to ALCAM; the ratio of EDA2R to L1CAM; the ratio of TIE1 to EPHA5; the ratio of EDA2R to EPHB2; the ratio of CFD to F5; the ratio of EDA2R to APP; the ratio of IL13RA1 to LTA LTB; the ratio of CDNF to IL20RA; the ratio of EDA2R to NRXN3; the ratio of EDA2R to CADM1; and the ratio of EDA2R to RTN4R, compared to a control.

In some examples, the method includes measuring at least 2, at least 3, at least 4, at least 5, at least 6, at least 7, at least 8, at least 9, at least 10 or all of the above-listed biomarkers in a CSF sample obtained from the subject.

Conversely, the method includes the step of identifying the subject as having RRMS if there is an increase in at least one of LTA LTB; the ratio of JAM3 to EDA2R; the ratio of TYRO3 to EDA2R; the ratio of LTA LTB to SERPING1; the ratio of NTRK3 to EDA2R; the ratio of WIF1 to EDA2R; the ratio of EPHA5 to DLL1; the ratio of CADM1 to CDNF; and the ratio of ROBO2 to IL17RC; and/or a decrease in at least one of SHH; the ratio of EDA2R to ROBO2; the ratio of F3 to ROBO2; the ratio of EDA2R to STX1A; the ratio of EDA2R to EPHA5; the ratio of EDA2R to ALCAM; the ratio of EDA2R to L1CAM; the ratio of TIE1 to EPHA5; the ratio of EDA2R to EPHB2; the ratio of CFD to F5; the ratio of EDA2R to APP; the ratio of IL13RA1 to LTA LTB; the ratio of CDNF to IL20RA; the ratio of EDA2R to NRXN3; the ratio of EDA2R to CADM1; and the ratio of EDA2R to RTN4R, compared to a control.

In particular embodiments, the at least one biomarker includes the ratio of JAM3 to EDA2R; the ratio of TYRO3 to EDA2R; the ratio of EDA2R to ROBO2; the ratio of F3 to ROBO2; the ratio of EDA2R to STX1A; the ratio of EDA2R to EPHA5; the ratio of LTA LTB to SERPING1; the ratio of NTRK3 to EDA2R; the ratio of WIF1 to EDA2R; the ratio of EDA2R to ALCAM; the ratio of EDA2R to L1CAM; the ratio of TIE1 to EPHA5; the ratio of EDA2R to EPHB2; the ratio of CFD to F5; the ratio of EDA2R to APP; the ratio of IL13RA1 to LTA LTB; the ratio of EPHA5 to DLL1; the ratio of CADM1 to CDNF; the ratio of CDNF to IL20RA; SHH; the ratio of EDA2R to NRXN3; the ratio of ROBO2 to IL17RC; the ratio of EDA2R to CADM1; the ratio of EDA2R to RTN4R; and LTA LTB.

In some examples, the at least one biomarker includes the ratio of EDA2R to a second protein. In particular examples, the at least one biomarker includes the ratio of JAM3 to EDA2R and up to 10, up to 20, up to 30, up to 40 or up to 50 additional biomarkers. In other particular examples, the at least one biomarker includes the ratio of TYRO3 to EDA2R and up to 10, up to 20, up to 30, up to 40 or up to 50 additional biomarkers. In other particular examples, the at least one biomarker includes the ratio of EDA2R to ROBO2 and up to 10, up to 20, up to 30, up to 40 or up to 50 additional biomarkers. In other particular examples, the at least one biomarker includes the ratio of EDA2R to STX1A and up to 10, up to 20, up to 30, up to 40 or up to 50 additional biomarkers. In other particular examples, the at least one biomarker includes the ratio of EDA2R to EPHA5 and up to 10, up to 20, up to 30, up to 40 or up to 50 additional biomarkers. In other particular examples, the at least one biomarker includes the ratio of NTRK3 to EDA2R and up to 10, up to 20, up to 30, up to 40 or up to 50 additional biomarkers. In other particular examples, the at least one biomarker includes the ratio of WIF1 to EDA2R and up to 10, up to 20, up to 30, up to 40 or up to 50 additional biomarkers. In other particular examples, the at least one biomarker includes the ratio of EDA2R to ALCAM and up to 10, up to 20, up to 30, up to 40 or up to 50 additional biomarkers. In other particular examples, the at least one biomarker includes the ratio of EDA2R to L1CAM and up to 10, up to 20, up to 30, up to 40 or up to 50 additional biomarkers. In other particular examples, the at least one biomarker includes the ratio of EDA2R to EPHB2 and up to 10, up to 20, up to 30, up to 40 or up to 50 additional biomarkers. In other particular examples, the at least one biomarker includes the ratio of EDA2R to APP and up to 10, up to 20, up to 30, up to 40 or up to 50 additional biomarkers. In other particular examples, the at least one biomarker includes the ratio of EDA2R to NRXN3 and up to 10, up to 20, up to 30, up to 40 or up to 50 additional biomarkers. In other particular examples, the at least one biomarker includes the ratio of EDA2R to CADM1 and up to 10, up to 20, up to 30, up to 40 or up to 50 additional biomarkers. In other particular examples, the at least one biomarker includes the ratio of EDA2R to RTN4R and up to 10, up to 20, up to 30, up to 40 or up to 50 additional biomarkers.

In some examples, the at least one biomarker includes the ratio of F3 to ROBO2 and up to 10, up to 20, up to 30, up to 40 or up to 50 additional biomarkers.

In some examples, the at least one biomarker includes the ratio of LTA LTB to SERPING1 and up to 10, up to 20, up to 30, up to 40 or up to 50 additional biomarkers.

In some examples, the at least one biomarker includes the ratio of TIE1 to EPHA5 and up to 10, up to 20, up to 30, up to 40 or up to 50 additional biomarkers.

In some examples, the at least one biomarker includes the ratio of CFD to F5 and up to 10, up to 20, up to 30, up to 40 or up to 50 additional biomarkers.

In some examples, the at least one biomarker includes the ratio of IL13RA1 to LTA LTB and up to 10, up to 20, up to 30, up to 40 or up to 50 additional biomarkers.

In some examples, the at least one biomarker includes the ratio of EPHA5 to DLL1 and up to 10, up to 20, up to 30, up to 40 or up to 50 additional biomarkers.

In some examples, the at least one biomarker includes the ratio of CADM1 to CDNF and up to 10, up to 20, up to 30, up to 40 or up to 50 additional biomarkers.

In some examples, the at least one biomarker includes the ratio of CDNF to IL20RA and up to 10, up to 20, up to 30, up to 40 or up to 50 additional biomarkers.

In some examples, the at least one biomarker includes SHH and up to 10, up to 20, up to 30, up to 40 or up to 50 additional biomarkers.

In some examples, the at least one biomarker includes the ratio of ROBO2 to IL17RC and up to 10, up to 20, up to 30, up to 40 or up to 50 additional biomarkers.

In some examples, the at least one biomarker includes LTA LTB and up to 10, up to 20, up to 30, up to 40 or up to 50 additional biomarkers.

In some examples, the method further includes measuring the level of IL-12p40 in the CSF sample obtained from the subject. An increase in IL-12p40 indicates the subject has progressive MS.

In some embodiments, the control is a reference standard. In other examples, the control is an average value obtained from healthy subjects.

In some embodiments, the method further includes providing an appropriate therapy to the subject with progressive MS or RRMS, such as by administering an immunomodulatory agent, or by administering agents that inhibit or activate the biomarkers identified herein directly in the CSF. Such agents include, for example, monoclonal antibodies or antigen-binding fragments thereof (such as Fab fragments) that block an identified biomarker in the CSF.

In some embodiments, the method further includes obtaining a CSF sample from the subject.

In some embodiments, the biomarker is measured using an antibody specific for the biomarker, such as in an immunoassay. In other embodiments, the biomarker is measured using an aptamer that specifically binds the biomarker. The antibody or aptamer can be chemically modified or labelled, such as for the purposes of detection.

Also provided herein is an array for detection and quantitation of biomarkers that identify an MS patient as having progressive MS or RRMS.

In some examples, the array comprises binding molecules (such as antibodies or aptamers) that specifically bind at least one of JAM3, EDA2R, TYRO3, ROBO2, F3, STX1A, EPHA5, LTA LTB, SERPING1, NTRK3, WIF1, ALCAM, L1CAM, TIE1, EPHB2, CFD, F5, APP, IL13RA1, DLL1, CADM1, CDNF, IL20RA, SHH, NRXN3, IL17RC and RTN4R. In specific examples, the array consists essentially of antibodies or aptamers that specifically bind at least 2, at least 3, at least 4, at least 5, at least 6, at least 7, at least 8, at least 9, at least 10, or all of JAM3, EDA2R, TYRO3, ROBO2, F3, STX1A, EPHA5, LTA LTB, SERPING1, NTRK3, WIF1, ALCAM, L1CAM, TIE1, EPHB2, CFD, F5, APP, IL13RA1, DLL1, CADM1, CDNF, IL20RA, SHH, NRXN3, IL17RC and RTN4R.

Also provided herein are methods of treating progressive MS or RRMS in a subject by measuring at least 1, at least 2, at least 3, at least 4, at least 5, at least 6, at least 7, at least 8, at least 9, at least 10 or all of the specific biomarkers listed above in the CSF of the subject and administering an appropriate therapy to the subject, such as an immunomodulatory therapy.

Further provided are methods of evaluating the effectiveness of a therapy for treating progressive MS or RRMS by measuring at least 1, at least 2, at least 3, at least 4, at least 5, at least 6, at least 7, at least 8, at least 9, at least 10 or all of the specific biomarkers listed above in the CSF before and after treatment.

C. Identifying Patients with Intrathecal Inflammation

Provided herein is a method of identifying a subject as having intrathecal inflammation by measuring and detecting an increase in one or more biomarkers associated with intrathecal inflammation. In some embodiments, the method includes measuring at least one biomarker in a CSF sample obtained from the subject, wherein the at least one biomarker is selected from sCD27, SLAMF7, GZMA, TNFRSF25, MMP9, SLAMF3, SLAMF2, TNFRSF17, TNFSF13B, the ratio of TNFRSF17 to TNFSF13B, TNFSF15, TNFRSF1B and CXCL10; and identifying the subject as having intrathecal inflammation if there is an increase in the at least one biomarker relative to a control. In some examples, the method includes measuring at least 2, at least 3, at least 4, at least 5, at least 6, at least 7, at least 8, at least 9, at least 10 or all of the above-listed biomarkers in a CSF sample obtained from the subject.

Figure 16:
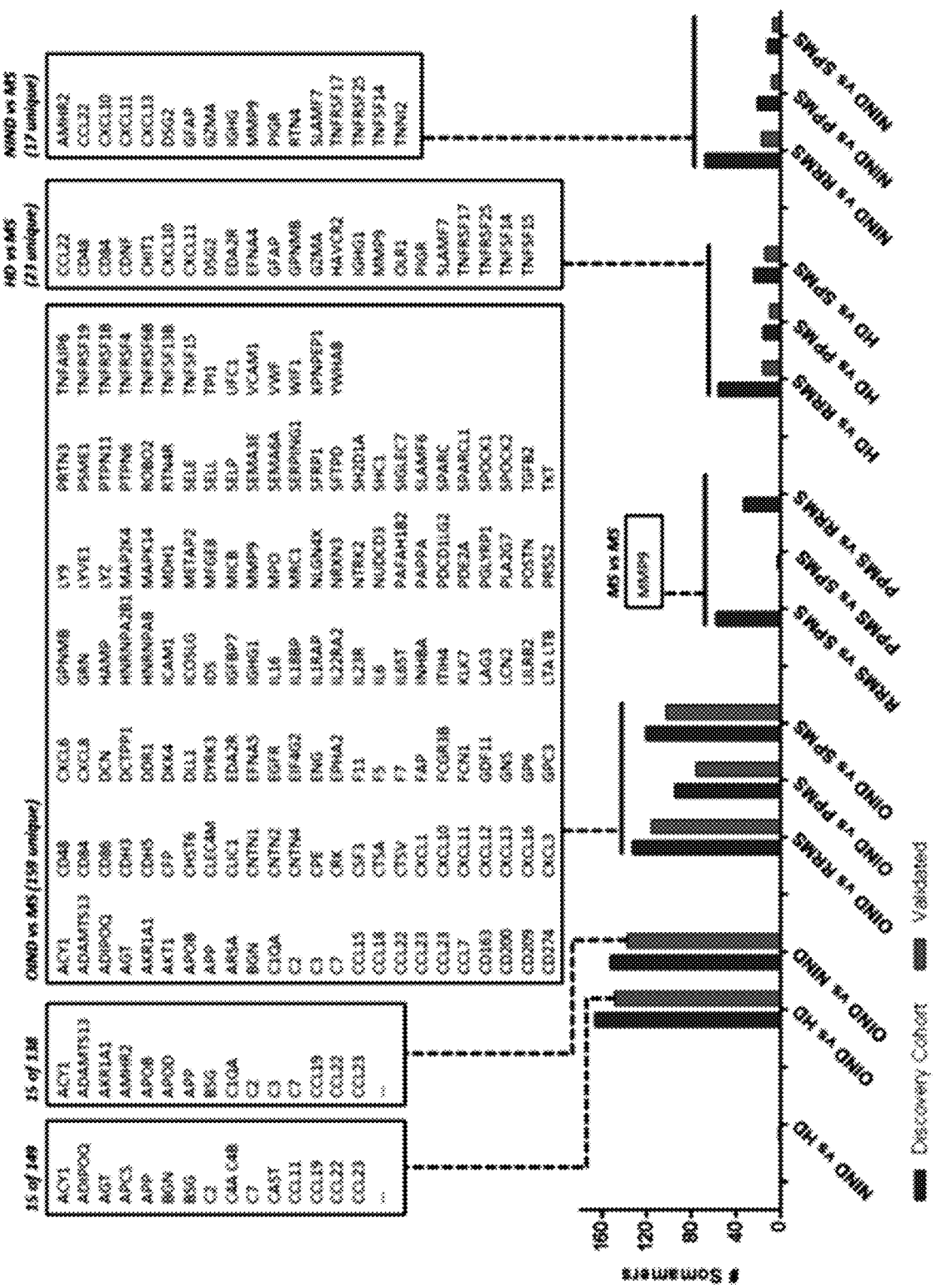
FIG. 16 is a graph showing CSF biomarkers differentiating MS from other diagnostic categories. Shown is a graphical representation of SOMAmers identified as statistically significantly different among 15 diagnostic comparisons in the Discovery cohort (left bars) and those that were validated as significantly different in the Validation cohort (right bars). Text boxes list gene names of validated SOMAmers in various diagnostic comparisons. For OIND vs HD and OIND vs NIND comparisons the boxes show only the first 15 alphabetically sorted SOMAmers.

In other embodiments, the at least one biomarker includes at least one biomarker listed in Table 1, Tables 3A-3H, Table 4, Table 5, Tables 6A-6B, FIG. 16 and/or FIGS. 22A-22B. In some examples, the control is a reference standard. In other examples, the control is an average value obtained from healthy subjects and/or subjects diagnosed with a non-inflammatory neurological disease.

In particular examples, the at least one biomarker includes sCD27. In specific examples, the at least one biomarker includes sCD27 and up to 10, up to 20, up to 30, up to 40 or up to 50 additional biomarkers. In one non-limiting example, sCD27 is the only biomarker measured.

In some examples, the method further includes measuring the level of IL-12p40 in the CSF sample obtained from the subject. An increase in IL-12p40 indicates the presence of intrathecal inflammation.

In some embodiments, the subject suffers from a neurological disease. In some examples, the neurological disease is a type of multiple sclerosis (MS), such as primary progressive multiple sclerosis (PPMS), secondary progressive multiple sclerosis (SPMS) or relapsing remitting multiple sclerosis (RRMS).

In some embodiments, the method further includes identifying the subject exhibiting intrathecal inflammation as having MS. The method includes measuring at least one biomarker in a CSF sample obtained from the subject, wherein the at least one biomarker is selected from TNFRSF17, TNFSF13B, the ratio of TNFRSF17 to TNFSF13B, TNFSF15, TNFRSF1B and CXCL10; and identifying the subject as having MS if there is a decrease in at least one of TNFSF13B, TNFSF15, TNFRSF1B and CXCL10 and/or an increase in at least one of TNFSF17 and the ratio of TNFRSF17 to TNFSF13B, compared to a control. In some examples, the method includes measuring at least 2, at least 3, at least 4 or all of the above-listed biomarkers in a CSF sample obtained from the subject. In other embodiments, the at least one biomarker includes at least one biomarker listed in Table 1, Tables 3A-3H, Table 4, Table 5, Tables 6A-6B, FIG. 16 and/or FIGS. 22A-22B.

In some examples, the control is a reference standard. In other examples, the control is an average value obtained from subjects diagnosed with an inflammatory neurological disease other than MS.

In some embodiments, the subject identified as having intrathecal inflammation is treated with an immunomodulatory therapy. The immunomodulatory therapy can include, for example, a T cell depleting agent and/or a B cell depleting agent.

In some embodiments, the method further includes obtaining a CSF sample from the subject.

In some embodiments, the biomarker is measured using an antibody specific for the biomarker, such as in an immunoassay. In other embodiments, the biomarker is measured using an aptamer that specifically binds the biomarker. In some examples, the antibody or aptamer is chemically modified or labelled, such as for detection.

Also provided herein is an array for detection and quantitation of biomarkers that identify a subject as having intrathecal inflammation. In some examples, the array comprises binding molecules (such as antibodies or aptamers) that specifically bind at least one of sCD27, SLAMF7, GZMA, TNFRSF25, MMP9, SLAMF3, SLAMF2, TNFRSF17, TNFSF13B, TNFSF15, TNFRSF1B and CXCL10. In specific examples, the array consists essentially of antibodies or aptamers that specifically bind at least 2, at least 3, at least 4, at least 5, at least 6, at least 7, at least 8, at least 9, or at least 10 biomarkers selected from sCD27, SLAMF7, GZMA, TNFRSF25, MMP9, SLAMF3, SLAMF2, TNFRSF17, TNFSF13B, TNFSF15, TNFRSF1B and CXCL10.

D. Differentiating MS Patients from Patients with Other Inflammatory Neurological Disorders Provided herein is a method of identifying a subject exhibiting intrathecal inflammation as having MS by measuring and detecting an increase or decrease in one or more biomarkers that distinguish between MS patients and patients having other inflammatory neurological disorders. In some embodiments, the method includes measuring at least one biomarker in a CSF sample obtained from the subject, wherein the at least one biomarker is selected from TNFRSF17, TNFSF13B, the ratio of TNFRSF17 to TNFSF13B, TNFSF15, TNFRSF1B and CXCL10; and identifying the subject as having MS if there is a decrease in at least one of TNFSF13B, TNFSF15, TNFRSF1B and CXCL10 and/or an increase in at least one of TNFSF17 and the ratio of TNFRSF17 to TNFSF13B, compared to a control. In some examples, the method includes measuring at least 2, at least 3, at least 4 or all of the above-listed biomarkers in a CSF sample obtained from the subject. In other embodiments, the at least one biomarker includes at least one biomarker listed in Table 1, Tables 3A-3H, Table 4, Table 5, Tables 6A-6B, FIG. 16, FIGS. 18A-18D and/or FIG. 22A.

In some examples, the control is a reference standard. In other examples, the control is an average value obtained from subjects diagnosed with an inflammatory neurological disease other than MS.

In some examples, the MS is a progressive MS, such PPMS or SPMS. In other examples, the MS is RRMS.

In some embodiments, the subject identified as having intrathecal inflammation is treated with an immunomodulatory therapy. The immunomodulatory therapy can include, for example, a T cell depleting agent and/or a B cell depleting agent.

In some embodiments, the method further includes obtaining a CSF sample from the subject.

In some embodiments, the biomarker is measured using an antibody specific for the biomarker, such as in an immunoassay. In other embodiments, the biomarker is measured using an aptamer that specifically binds the biomarker. In some examples, the antibody or aptamer is chemically modified or labelled, such as for detection.

Also provided herein is an array for detection and quantitation of biomarkers that identify subjects exhibiting intrathecal inflammation as having MS. In some examples, the array comprises binding molecules (such as antibodies or aptamers) that specifically bind at least one of TNFRSF17, TNFSF13B, TNFSF15, TNFRSF1B and CXCL10. In specific examples, the array consists essentially of antibodies or aptamers that specifically bind at least 2, at least 3 or at least 4 biomarkers selected from TNFRSF17, TNFSF13B, TNFSF15, TNFRSF1B and CXCL10.

E. Identifying Patients with Progressive MS

Provided herein are methods of identifying an MS patient as having progressive MS by measuring and detecting an increase or decrease in one or more biomarkers capable of distinguishing patients with progressive MS (PPMS or SPMS) from patients with RRMS.

In some embodiments, the method includes measuring at least one biomarker in a CSF sample obtained from the subject, wherein the at least one biomarker is selected from the ratio of sCD27 to the total number of CSF T cells, TNFSF14, EPHB4, OLR1, PP1B, CDH15, PDE2A, IGFBP7, H2AFZ, APOD, DKKL1, GFRA1, EDA2R and CCL25; identifying the subject as having progressive MS if there is a decrease in at least one of TNFSF14, EPHB4, PP1B, CDH15, PDE2A, IGFBP7, H2AFZ, APOD, DKKL1 and CCL25, and/or an increase in at least one of the ratio of sCD27 to the total number of CSF T cells, OLR1, GFRA1 and EDA2R, compared to a control. In some examples, the method includes measuring at least 2, at least 3, at least 4, at least 5, at least 6, at least 7, at least 8, at least 9, at least 10 or all of the above-listed biomarkers in a CSF sample obtained from the subject. In yet other embodiments, the at least one biomarker includes at least one biomarker listed in Table 1, Tables 3A-3H, Table 4, Table 5, Tables 6A-6B, FIG. 16, FIGS. 19A-19D and/or FIG. 22B.

In some examples, the at least one biomarker includes the ratio of sCD27 to the total number of CSF T cells. In specific examples, the at least one biomarker includes the ratio of sCD27 to the total number of CSF T cells and up to 10, up to 20, up to 30, up to 40 or up to 50 additional biomarkers. In one non-limiting example, the ratio of sCD27 to the total number of CSF T cells is the only biomarker measured.

In some examples, the method further includes measuring the level of IL-12p40 in the CSF sample obtained from the subject. An increase in IL-12p40 indicates the subject has progressive MS.

In some embodiments, the control is a reference standard. In other examples, the control is an average value obtained from healthy subjects or subjects diagnosed with RRMS.

In some embodiments, the method further includes providing an appropriate therapy to the subject that has progressive MS. For example, any agent that decreases the sCD27 to T cell ratio could be used to treat progressive MS.

In some embodiments, the method further includes obtaining a CSF sample from the subject.

In some embodiments, the biomarker is measured using an antibody specific for the biomarker, such as in an immunoassay. In other embodiments, the biomarker is measured using an aptamer that specifically binds the biomarker. In some examples, the antibody or aptamer is chemically modified or labelled, such as for detection.

Also provided herein is an array for detection and quantitation of biomarkers that identify an MS patient as having progressive MS.

In some examples, the array comprises binding molecules (such as antibodies or aptamers) that specifically bind at least one of sCD27, TNFSF14, EPHB4, OLR1, PP1B, CDH15, PDE2A, IGFBP7, H2AFZ, APOD, DKKL1, GFRA1, EDA2R and CCL25. In specific examples, the array consists essentially of antibodies or aptamers that specifically bind at least 2, at least 3, at least 4, at least 5, at least 6, at least 7, at least 8, at least 9, or at least 10 biomarkers selected from sCD27, TNFSF14, EPHB4, OLR1, PP1B, CDH15, PDE2A, IGFBP7, H2AFZ, APOD, DKKL1, GFRA1, EDA2R and CCL25.

F. Identifying Subjects with Inflammatory Neurological Diseases Other than MS (OIND)

Provided herein is a method of identifying a subject as having an inflammatory neurological disease other than MS by measuring and detecting an increase in one or more biomarkers that distinguish patients having MS from patients that have other inflammatory neurological disorders. In some embodiments, the method includes measuring at least one biomarker in a CSF sample obtained from the subject, wherein the at least one biomarker is selected from sCD163, LAG3, CD209, LYZ, TNFRSF4 and CCL7; and identifying the subject as having an inflammatory neurological disease other than MS if there is an increase in the at least one biomarker relative to a control. In some examples, the method includes measuring at least 2, at least 3, at least 4, at least 5 or all of the above-listed biomarkers in a CSF sample obtained from the subject. In other embodiments, the at least one biomarker includes at least one biomarker listed in Table 1, Tables 3A-3H, Table 4, Table 5, Tables 6A-6B, FIG. 16 and/or FIG. 22A.

In some examples, the control is a reference standard. In other examples, the control is an average value obtained from subjects diagnosed with MS.

In some embodiments, the subject identified as having an inflammatory neurological disease is treated with an immunomodulatory therapy. The immunomodulatory therapy can include, for example, a T cell depleting agent and/or a B cell depleting agent.

In some embodiments, the method further includes obtaining a CSF sample from the subject.

In some embodiments, the biomarker is measured using an antibody specific for the biomarker, such as in an immunoassay. In other embodiments, the biomarker is measured using an aptamer that specifically binds the biomarker. In some examples, the antibody or aptamer is chemically modified or labelled, such as for detection.

Also provided herein is an array for detection and quantitation of biomarkers that identify a subject as having an inflammatory neurological disease other than MS. In some examples, the array comprises binding molecules (such as antibodies or aptamers) that specifically bind at least one of sCD163, LAG3, CD209, LYZ, TNFRSF4 and CCL7. In specific examples, the array consists essentially of antibodies or aptamers that specifically bind at least 2, at least 3, at least 4 or at least 5 biomarkers selected from sCD163, LAG3, CD209, LYZ, TNFRSF4 and CCL7.

G. Differentiating Healthy Subjects from Subjects with a Neurological Disease

Provided herein is a method of identifying a subject as having a neurological disease by measuring and detecting an increase or decrease in one or more biomarkers associated with neurological disease. In some embodiments, the method includes measuring at least one biomarker in a CSF sample obtained from the subject, wherein the at least one biomarker is selected from LGMN, GPNMB, SPOCK2, the ratio of SPOCK2 to GPNMB, IGFBP7, MFRP and CHIT1; and identifying the subject as having a neurological disease if there is an increase in at least one of GPNMB, OLR1, MFRP and CHIT1, and/or a decrease in at least one of LGMN, SPOCK2, the ratio of SPOCK2 to GPNMB, and IGFBP7, relative to a control. In some examples, the method includes measuring at least 2, at least 3, at least 4, at least 5 or all of the above-listed biomarkers in a CSF sample obtained from the subject. In other embodiments, the at least one biomarker includes at least one biomarker listed in Table 1, Tables 3A-3H, Table 4, Table 5, Tables 6A-6B, FIG. 16 and/or FIGS. 22A-22B.

In some examples, the control is a reference standard. In other examples, the control is an average value obtained from healthy subjects.

In some embodiments, the method further includes providing an appropriate therapy to treat the neurological disease.

In some embodiments, the method further includes obtaining a CSF sample from the subject.

In some embodiments, the biomarker is measured using an antibody specific for the biomarker, such as in an immunoassay. In other embodiments, the biomarker is measured using an aptamer that specifically binds the biomarker. In some examples, the antibody or aptamer is chemically modified or labelled, such as for detection.

Also provided herein is an array for detection and quantitation of biomarkers that identify a subject as having a neurological disease. In some examples, the array comprises binding molecules (such as antibodies or aptamers) that specifically bind at least one of LGMN, GPNMB, SPOCK2, IGFBP7, MFRP and CHIT1. In specific examples, the array consists essentially of antibodies or aptamers that specifically bind at least 2, at least 3, at least 4 or at least 5 biomarkers selected from LGMN, GPNMB, SPOCK2, IGFBP7, MFRP and CHIT1.

H. Detecting Immune Cell Infiltration and/or Activation

Provided herein is a method of detecting immune cell infiltration and/or activation in CNS tissue of a subject having a neurological disorder by calculating the ratio of an immune-cell specific biomarker to the total number of corresponding cells that produce the biomarker. In some embodiments, the method includes measuring sCD27, sCD14, TNFRSF17 and/or CD209 in a CSF sample obtained from a subject; measuring the absolute number of T cells, monocytes, B cells and/or DCs in the CSF sample obtained from the subject; calculating the ratio of sCD27 to the absolute number of T cells, the ratio of sCD14 to the absolute number of monocytes, the ratio of TNFRSF17 to the absolute number of B cells and/or the ratio of CD209 to the absolute number of DCs in the CSF of the subject; and identifying T cell infiltration in the CNS if an increase in the ratio of sCD27 to absolute number of T cells is detected; identifying microglial/macrophage activation in the CNS if an increase in the ratio of sCD14 to absolute number of monocytes is detected; identifying B cell and/or plasma cell infiltration in the CNS if an increase in the ratio of TNFRSF17 to absolute number of B cells is detected; and/or identifying DC infiltration in the CNS if an increase in the ratio of CD209 to absolute number of DCs is detected, compared to a control.

In some examples, the control is a reference standard. In other examples, the control is an average value obtained from healthy subjects and/or subjects diagnosed with a non-inflammatory neurological disease.

In some embodiments, the method further includes obtaining a CSF sample from the subject.

In some embodiments, the biomarker (i.e. sCD27, sCD14, TNFRSF17 and/or CD209) is measured using an antibody specific for the biomarker, such as in an immunoassay. In other embodiments, the biomarker is measured using an aptamer that specifically binds the biomarker.

Also provided herein is an array for detection and quantitation of biomarkers that indicate immune cell infiltration and/or activation. In some examples, the array comprises binding molecules (such as antibodies or aptamers) that specifically bind at least one of sCD27, sCD14, TNFRSF17 and/or CD209. In specific examples, the array consists essentially of antibodies or aptamers that specifically bind sCD27, sCD14, TNFRSF17 and CD209.

I. Identifying Subjects with CNS Tissue Injury and/or Neurodegeneration

Provided herein is a method of identifying a subject as having CNS tissue injury and/or neurodegeneration by measuring and detecting an increase or decrease in one or more biomarkers associated with CNS tissue injury, neurodegeneration and/or disability. In some embodiments, the method includes measuring at least one biomarker in a CSF sample obtained from a subject, wherein the at least one biomarker is selected from IGFBP7, LGMN, ROR1, EFNA4, IL-1RAP, HGF, TNFSF4, EDA2R, CD109, TNFSF8, OLR1, GPI, PLXNC1, PDIA3, ITGAV/ITGB5, CDNF, GPC5, HAVCR2, IL17RC, TNFRSF17, CNTN1, IL18BP, IL18R1, FCGR2A, FCGR2B, FCGR3B, IL11RA, CHST6, FUT5, CGA/CGB, CD300C, GPNMB, SLAMF7, the ratio of JAM3 to EDA2R, the ratio of TYRO3 to EDA2R, the ratio of EDA2R to ROBO2, the ratio of F3 to ROBO2, the ratio of EDA2R to STX1A, the ratio of EDA2R to EPHA5, the ratio of NTRK3 to EDA2R, the ratio of WIF1 to EDA2R, the ratio of EDA2R to ALCAM, the ratio of EDA2R to L1CAM, the ratio of EDA2R to EPHB2, the ratio of CFD to F5, the ratio of EDA2R to APP, the ratio of CADM1 to CDNF, the ratio of CDNF to IL20RA, SHH, the ratio of EDA2R to NRXN3, the ratio of ROBO2 to IL17RC, the ratio of EDA2R to CADM1 and the ratio of EDA2R to RTN4R; and identifying the subject as having CNS tissue injury and/or neurodegeneration if there is a decrease in at least one of IGFBP7, LGMN, the ratio of JAM3 to EDA2R, the ratio of TYRO3 to EDA2R, the ratio of NTRK3 to EDA2R, the ratio of WIF1 to EDA2R, the ratio of CADM1 to CDNF, and the ratio of ROBO2 to IL17RC, and/or an increase in at least one of ROR1, EFNA4, IL-1RAP, HGF, TNFSF4, EDA2R, CD109, TNFSF8, OLR1, GPI, PLXNC1, PDIA3, ITGAV/ITGB5, CDNF, GPC5, HAVCR2, CPE, IL17RC, TNFRSF17, CNTN1, IL18BP, IL18R1, FCGR2A, FCGR2B, FCGR3B, IL-11RA, CHST6, FUT5, CGA/CGB, CDNF, CD300C, GPNMB, SLAMF7, the ratio of TNFRSF17 to IL16, the ratio of EDA2R to ROBO2, the ratio of F3 to ROBO2, the ratio of EDA2R to STX1A, the ratio of EDA2R to EPHA5, the ratio of EDA2R to ALCAM, the ratio of EDA2R to L1CAM, the ratio of EDA2R to EPHB2, the ratio of CFD to F5, the ratio of EDA2R to APP, the ratio of CDNF to IL20RA, SHH, the ratio of EDA2R to NRXN3, the ratio of EDA2R to CADM1 and the ratio of EDA2R to RTN4R, compared to a control.

In some examples, the method includes measuring at least 2, at least 3, at least 4, at least 5, at least 6, at least 7, at least 8, at least 9, at least 10 or all of the above-listed biomarkers in a CSF sample obtained from the subject. In other embodiments, the at least one biomarker includes at least one biomarker listed in Table 1, Tables 3A-3H, Table 4, Table 5, Tables 6A-6B, FIG. 16 and/or FIGS. 22A-22B. In yet other embodiments, the at least one biomarker includes all of the biomarkers listed in Table 1, Tables 3A-3H, Table 4, Table 5, Tables 6A-6B, FIG. 16 and FIGS. 22A-22B.

In some examples, the control is a reference standard. In other examples, the control is an average value obtained from healthy subjects.

In some instances, the biomarkers also provide an indication of microglial activation (e.g. IL-1RAP, IL-18BP and IL-18R1).

In some embodiments, the method further includes providing an appropriate treatment to the subject having CNS injury and/or degeneration. For example, the subject could be treated with an agent that increases IGFBP7 or LGMN to promote neuroprotection. As another example, the subject could be treated with an agent that decreases ROR1, EFNA4, IL-1RAP, HGF, TNFSF4, EDA2R, CD109, TNFSF8, OLR1, CKB, GPI, PLXNC1, PDIA3, ITGAV/ITGB5, CDNF, GPC5, HAVCR2, CPE, IL-17RC, CXCL16, TNFRSF17, CNTN1, IL-18BP, IL-18R1, FCGR2A, FCGR2B, FCGR3B, AGT, CTSH, IL-11RA, CHST6, FUT5, CGA/CGB, CDNF, CD300C, GPNMB, or SLAMF7 to enhance neuroprotection in the subject.

In some embodiments, the method further includes obtaining a CSF sample from the subject.

In some embodiments, the biomarker is measured using an antibody specific for the biomarker, such as in an immunoassay. In other embodiments, the biomarker is measured using an aptamer that specifically binds the biomarker. In some examples, the antibody or aptamer is chemically modified or labelled, such as for detection.

Also provided herein is an array for detection and quantitation of biomarkers that indicate a subject as having CNS tissue injury and/or neurodegeneration. In some examples, the array comprises binding molecules (such as antibodies or aptamers) that specifically bind at least one of IGFBP7LGMN, ROR1, EFNA4, IL-1RAP, HGF, TNFSF4, EDA2R, CD109, TNFSF8, OLR1, CKB, GPI, PLXNC1, PDIA3, ITGAV/ITGB5, CDNF, GPC5, HAVCR2, CPE, IL-17RC, CXCL16, TNFRSF17, CNTN1, IL-18BP, IL-18R1, FCGR2A, FCGR2B, FCGR3B, AGT, CTSH, IL-11RA, CHST6, FUT5, CGA/CGB, CDNF, CD300C, GPNMB and SLAMF7. In specific examples, the array consists essentially of antibodies or aptamers that specifically bind at least 2, at least 3, at least 4, at least 5, at least 6, at least 7, at least 8, at least 9, or at least 10 biomarkers selected from IGFBP7, LGMN, ROR1, EFNA4, IL-1RAP, HGF, TNFSF4, EDA2R, CD109, TNFSF8, OLR1, CKB, GPI, PLXNC1, PDIA3, ITGAV/ITGB5, CDNF, GPC5, HAVCR2, CPE, IL-17RC, TNFRSF17, CNTN1, IL-18BP, IL-18R1, FCGR2A, FCGR2B, FCGR3B, AGT, CTSH, IL-11RA, CHST6, FUT5, CGA/CGB, CDNF, CD300C, GPNMB and SLAMF7.

J. Treating Inflammatory Neurological Diseases and Evaluating the Effectiveness of a Selected Treatment Provided herein is a method of treating an inflammatory neurological disease in a subject. In some embodiments, the method includes selecting a subject having an increased level of at least one biomarker in a CSF sample obtained from the subject compared to a control, wherein the at least one biomarker is selected from sCD27, SLAMF7, GZMA, TNFRSF25, MMP9, SLAMF3, SLAMF2, TNFRSF17, TNFSF13B, the ratio of TNFRSF17 to TNFSF13B, TNFSF15, TNFRSF1B and CXCL10; and administering to the subject an immunomodulatory therapy, thereby treating the inflammatory neurological disease. In some examples, the method includes selecting a subject having an increased level of at least 2, at least 3, at least 4, at least 5, at least 6, at least 7, at least 8, at least 9, at least 10 or all of the above-listed biomarkers in a CSF sample obtained from the subject.

In some embodiments, the method includes measuring at least one biomarker in a CSF sample obtained from the subject, wherein the at least one biomarker is selected from sCD27, SLAMF7, GZMA, TNFRSF25, MMP9, SLAMF3, SLAMF2, TNFRSF17, TNFSF13B, the ratio of TNFRSF17 to TNFSF13B, TNFSF15, TNFRSF1B and CXCL10; selecting the subject for treatment if there is an increase in the at least one biomarker relative to a control; and administering to the subject an immunomodulatory therapy, thereby treating the inflammatory neurological disease. In some examples, the method includes measuring at least 2, at least 3, at least 4, at least 5, at least 6, at least 7, at least 8, at least 9, at least 10 or all of the above-listed biomarkers in a CSF sample obtained from the subject.

In other embodiments, the at least one biomarker includes at least one biomarker listed in Table 1, Tables 3A-3H, Table 4, Table 5, Tables 6A-6B, FIG. 16 and/or FIGS. 22A-22B.

In some examples, the control is a reference standard. In other examples, the control is an average value obtained from healthy subjects and/or subjects diagnosed with a non-inflammatory neurological disease.

In some examples, the at least one biomarker comprises sCD27.

In some examples, the method further includes measuring the level of IL-12p40 in the CSF sample obtained from the subject.

In some embodiments, the neurological disease is a type of MS, such as PPMS, SPMS or RRMS.

In some examples, the immunomodulatory therapy comprises administration of a T cell depleting agent and/or a B cell depleting agent.

Further provided herein is a method of evaluating the effectiveness of a therapy for treating an inflammatory neurological disease. In some embodiments, the method includes measuring at least one biomarker in the CSF of the subject before and after treatment, wherein the at least one biomarker is selected from sCD27, SLAMF7, GZMA, TNFRSF25, MMP9, SLAMF3, SLAMF2, TNFRSF17, TNFSF13B, the ratio of TNFRSF17 to TNFSF13B, TNFSF15, TNFRSF1B and CXCL10. A decrease in the at least one biomarker indicates the therapy is effective for the treatment of the inflammatory neurological disease. In other embodiments, the at least one biomarker includes at least one biomarker listed in Table 1, Tables 3A-3H, Table 4, Table 5, Tables 6A-6B, FIG. 16 and/or FIGS. 22A-22B.

In particular examples, the at least one biomarker includes sCD27. In specific examples, the at least one biomarker includes sCD27 and up to 10, up to 20, up to 30, up to 40 or up to 50 additional biomarkers. In one non-limiting example, sCD27 is the only biomarker measured.

In some examples, the method further includes measuring the level of IL-12p40 in the CSF sample obtained from the subject.

In some embodiments, the neurological disease is a type of MS, for example, PPMS, SPMS or RRMS.

In some embodiments, the treatment comprises an immunomodulatory therapy, such as administration of a T cell depleting agent and/or a B cell depleting agent.

In some embodiments of the methods, the method further includes obtaining a CSF sample from the subject.

In some embodiments, the level of the biomarker is measured using an antibody specific for the biomarker, such as in an immunoassay. In other embodiments, the biomarker is measured using an aptamer that specifically binds the biomarker. In some examples, the antibody or aptamer is chemically modified or labelled, such as for detection.

K. Treating Inflammatory Neurological Diseases Other than MS and Evaluating the Effectiveness of a Selected Treatment Provided herein is a method of treating an inflammatory neurological disease other than MS in a subject. In some embodiments, the method includes selecting a subject for treatment if there is an increase in at least one biomarker in a CSF sample obtained from the subject compared to a control, wherein the at least one biomarker is selected from sCD163, LAG3, CD209, LYZ, TNFRSF4 and CCL7; and administering to the subject an immunomodulatory therapy. In some examples, the method includes selecting a subject for treatment if there is an increase in at least 2, at least 3, at least 4, at least 5 or all of the above-listed biomarkers in a CSF sample obtained from the subject.

In some embodiments, the method includes measuring at least one biomarker in a CSF sample obtained from the subject, wherein the at least one biomarker is selected from sCD163, LAG3, CD209, LYZ, TNFRSF4 and CCL7; selecting the subject for treatment if there is an increase in the at least one biomarker relative to a control; and administering to the subject an immunomodulatory therapy. In some examples, the method includes measuring at least 2, at least 3, at least 4, at least 5 or all of the above-listed biomarkers in a CSF sample obtained from the subject.

In other embodiments, the at least one biomarker includes at least one biomarker listed in Table 1, Tables 3A-3H, Table 4, Table 5, Tables 6A-6B, FIG. 16 and/or FIGS. 22A-22B.

In some examples, the control is a reference standard. In other examples, the control is an average value obtained from subjects diagnosed with MS.

In some examples, the treatment comprises an immunomodulatory therapy, such as administration of a T cell depleting agent and/or a B cell depleting agent.

Further provided herein is a method of evaluating the effectiveness of a therapy for treating an inflammatory neurological disease other than MS. In some embodiments, the method includes measuring at least one biomarker in the CSF of the subject before and after treatment, wherein the at least one biomarker is selected from sCD163, LAG3, CD209, LYZ, TNFRSF4 and CCL7. A decrease in the at least one biomarker indicates the therapy is effective for the treatment of the inflammatory neurological disease.

In some embodiments, the treatment comprises an immunomodulatory therapy, such as administration of a T cell depleting agent and/or a B cell depleting agent.

In some embodiments of the methods, the method further includes obtaining a CSF sample from the subject.

In some embodiments, the biomarker is measured using an antibody specific for the biomarker, such as in an immunoassay. In other embodiments, the biomarker is measured using an aptamer that specifically binds the biomarker. In some examples, the antibody or aptamer is chemically modified or labelled, such as for detection.

V. Detection and Quantification of Protein Biomarkers

The biomarkers disclosed herein can be detected in a biological sample, such as a CSF sample, using any one of a number of known assay methods for detection and quantitation of proteins. In particular, protein biomarkers can be detected using an immunoassay, mass spectrometry or an aptamer-based array.

A. Antibody-Based Detection

Antibodies specific for a particular biomarker can be used for detection and quantification by one of a number of immunoassay methods that are well known in the art, such as those presented in Harlow and Lane (Antibodies, *A Laboratory Manual*, CSHL, New York, 1988). For example, any standard immunoassay format, such as ELISA, Western blot, cytometric bead assay, RIA or electrochemiluminescent detection (see Example 1) can be used to measure protein levels. Thus, biomarker protein levels in a sample (such as a CSF sample) can readily be evaluated using these methods. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For immunoassay methods, commercially available ELISA kits for detection of specific protein, or commercially available antibodies to a desired target can be utilized (see Table 1 for a list of commercially available antibodies and kits that can be used to detect some of the biomarkers disclosed herein). Moreover, methods of making polyclonal and monoclonal antibodies are well known in the art. Polyclonal antibodies, antibodies which consist essentially of pooled monoclonal antibodies with different epitopic specificities, as well as distinct monoclonal antibody preparations are included. The preparation of polyclonal antibodies is well known to those skilled in the art (see, for example, Green et al., "Production of Polyclonal Antisera," in: *Immunochemical Protocols, pages* 1-5, Manson, ed., Humana Press, 1992; Coligan et al., "Production of Polyclonal Antisera in Rabbits, Rats, Mice and Hamsters," in: *Current Protocols in Immunology, section* 2.4.1, 1992).

The preparation of monoclonal antibodies likewise is conventional (see, for example, Kohler & Milstein, *Nature* 256:495, 1975; Coligan et al., sections 2.5.1-2.6.7; and Harlow et al. in: *Antibodies: a Laboratory Manual*, page 726, Cold Spring Harbor Pub., 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, e.g., Coligan et al., sections 2.7.1-2.7.12 and sections 2.9.1-2.9.3; Barnes et al., Purification of Immunoglobulin G (IgG), in: *Methods in Molecular Biology*, Vol. 10, pages 79-104, Humana Press, 1992).

Monoclonal antibodies specific for a particular protein can also be generated and selected using an antibody display library, such as a phage display library.

Antibodies include intact molecules as well as fragments thereof, such as Fab, F(ab')2, and Fv which are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody, defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). For example, antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945 and 4,331,647, and references contained therein; Nisonhoff et al., *Arch Biochem Biophys* 89:230, 1960; Porter, *Biochem J* 73:119, 1959; Edelman et al., *Methods in Enzymology*, Vol. 1, page 422, Academic Press, 1967; and Coligan et al. at sections 2.8.1-2.8.10 and 2.10.1-2.10.4).

B. Aptamer-Based Detection

Aptamers, small nucleic acid molecules that specifically bind a target protein, also can be used for detection and quantification of protein biomarkers in a biological sample. Aptamer-based arrays can be used for simultaneous detection of multiple biomarkers, even from very small sample volumes. A technology developed by SomaLogic (Boulder, Colo.) utilizes a new class of aptamer, termed Slow Off-rate Modified Aptamer (SOMAMER™). These aptamers are high-affinity aptamers that can be selected for almost any protein target (Gold et al., *PLoS ONE* 5(12):e15004), allowing for high-throughput proteomic analyses, such as for identifying protein biomarkers of disease (Webber et al., *Molecular & Cellular Proteomics* 13:10.1074/mcp.M113.032136, 1050-1064, 2014).

The SomaLogic proteomics assay is described in detail in Gold et al. (*PLoS ONE* 5(12):e15004) and Gold et al. (*Cold Spring Harb Perspect Biol* 4:a003582, 2012). CSF samples from healthy donor, NIND, OIND, RRMS, SPMS and PPMS subjects were evaluated using the SomaLogic aptamer-based proteomics platform. A selection of the biomarkers identified using this technique is shown in Tables 3A-3H, Table 4, Table 5 and Tables 6A-6B (see also Examples 3-5).

C. Mass Spectrometry

Quantitative spectroscopic approaches methods, such as SELDI, can be used to analyze biomarkers present in a sample, such as a CSF sample. In one example, surface-enhanced laser desorption-ionization time-of-flight (SELDI-TOF) mass spectrometry is used to detect protein, for example by using the PROTEINCHIP™ (Ciphergen Biosystems, Palo Alto, Calif.). Such methods are well known in the art (for example, see U.S. Pat. Nos. 5,719,060; 6,897,072; and 6,881,586). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as a biomarker disclosed herein) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

In some examples, the chromatographic surface includes antibodies that specifically bind at least 2, at least 3, at least 4, at least 5, at least 6, at least 7, at least 8, at least 9, or at least 10 disclosed herein, such as the biomarkers listed in Table 1, Tables 3A-3H, Table 4, Table 5, Tables 6A-6B, FIG. 16 and/or FIGS. 22A-22B. In some examples, the chromatographic surface includes antibodies that bind other molecules, such as housekeeping proteins (e.g. actin or myosin).

In another example, antibodies are immobilized onto the surface using a bacterial Fc binding support. The chromatographic surface is incubated with a sample, such as a CSF sample. The biomarkers present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

The following examples are provided to illustrate certain particular features and/or embodiments. These examples should not be construed to limit the disclosure to the particular features or embodiments described.

EXAMPLES

Example 1: Materials and Methods

This example describes the materials and experimental methods used for the studies described in Example 2.

Subjects

Figure 10B:
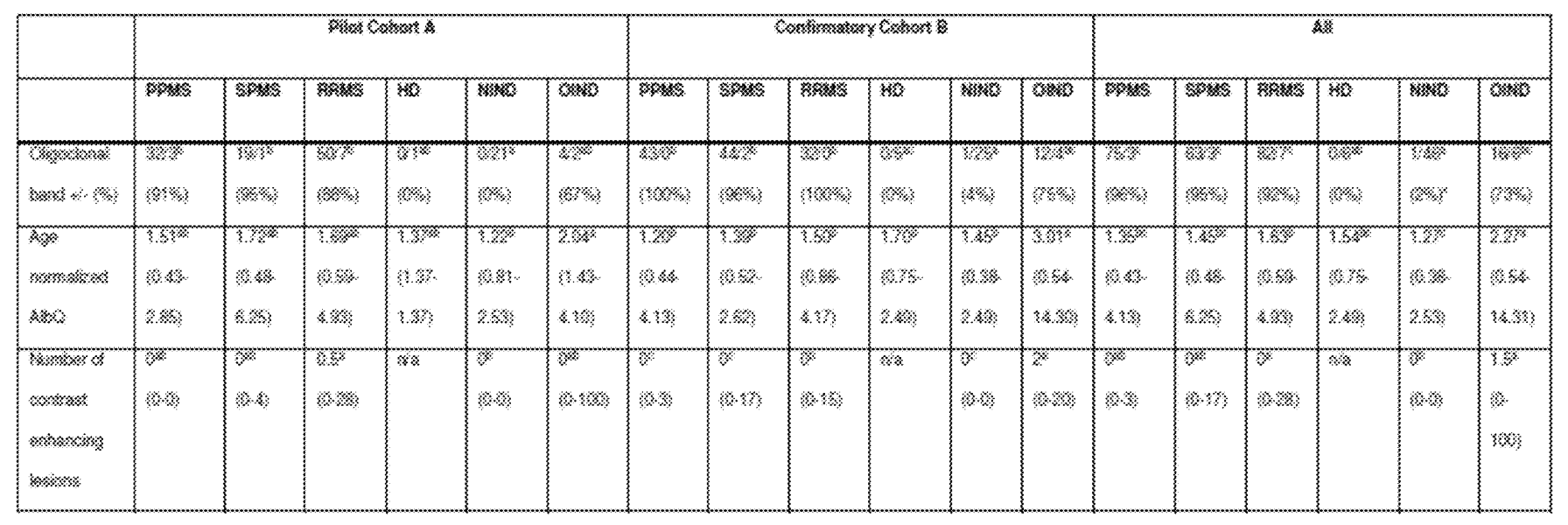

Subjects (FIG. 10) were prospectively recruited; Cohort A (N=193) between January 2008-2011 and Cohort B (N=193) after implementation of CSF immunophenotyping protocol (February 2011-January 2014). Consequently, immunophenotyping results on 153 out of 193 of Cohort B subjects were already reported and were solely used to compute combinatorial biomarkers (Han et al., *J Immunol* 192(6):2551-2563, 2014).

Patients did not receive CNS-targeting immunomodulatory treatments for a minimum of 3 months before CSF collection. All subjects underwent a thorough diagnostic work-up evaluating infectious and autoimmune causes, MRI and CSF studies.

Diagnoses of relapsing-remitting multiple sclerosis (RRMS), secondary-progressive MS (SPMS) and primary-progressive MS (PPMS) were based on the 2010 McDonald criteria (Polman et al., *Ann Neurol* 69:292-302, 2011). Other inflammatory neurological disorders (OIND) includes patients with cryptococcal meningo-encephalitis (n=12), central nervous system (CNS) paraneoplastic syndrome (n=6), cyclic meningitis (n=6), Aicardi-Goutieres syndrome with CNS involvement (n=4), Susac's syndrome (n=3), neonatal onset multisystem inflammatory disease (NOMID) with CNS involvement (n=2), Lyme disease with CNS involvement (n=2), HTLV-1 associated myelopathy (n=1), sarcoidosis with CNS involvement (n=1), CNS lupus erythematosus (n=1), CNS vasculitis (n=1), autoimmune lymphoproliferative syndrome with CNS involvement (n=1) and encephalitis/ventriculitis with unknown origin (n=5). Non-inflammatory diseases (NIND) group includes patients with systemic Lyme disease without CNS involvement (n=1), systemic cryptococcosis without CNS involvement (n=5), epilepsy (n=5), amyotrophic lateral sclerosis (n=3), compressive myelopathy (n=2), leukodystrophy (n=2), mitochondrial disease (n=1), hydromyelia (n=1), headache/dizziness without any CNS abnormality (n=6), and nonspecific/ischemic white matter lesions (WML) in MRI (n=21). Eight healthy donors (HD) were recruited through a web portal for research study volunteers, and none had a history of autoimmune, neurological or chronic illness.

The diagnosis and the level of diagnostic certainty (i.e. "definite", "likely" or "undiagnosed") were updated during longitudinal follow-up. Patients with remaining low diagnostic certainty were excluded.

CSF Collection, Processing and Immunophenotyping

CSF was collected on ice and processed according to written standard operating procedures. A portion of collected CSF was sent for diagnostic work-up, including cell count, electrophoresis, calculations of immunoglobulin G (IgG) index based on comparisons of serum/CSF albumin and IgG concentrations, and presence of oligoclonal bands (OCBs) by isoelectric focusing, RPR, Lyme Ab and IgG/PCR for selected pathogens, if indicated. Research CSF aliquots were assigned prospective alpha-numeric codes, and centrifuged at 335 g for 10 minutes at 4° C. within 15 minutes of collection. Cell pellets were 50-fold concentrated in X-VIVO 15 (Lonza) culture medium and counted by a hemocytometer; the number of white blood cells (WBC) per ml of CSF was calculated. A minimum of $1 \times 10^4$ viable CSF cells were analyzed by 12 color flow cytometry to enumerate absolute numbers of 14 subsets of CSF immune cells as previously described (Han et al., *J Immunol* 192(6):2551-2563, 2014). The supernatant was aliquoted and stored in polypropylene tubes at −80 OC until use.

Electrochemiluminescent Assay

Electrochemiluminescent assays were developed and optimized to quantify the concentrations of selected biomarkers in the CSF and cell culture supernatants using the MESO SCALE DISCOVERY™ (MSD, Gaithersburg, Md., USA) detection system. The MSD detection system provides a combination of high sensitivity with low background and a 5-log-order of magnitude dynamic range (Tighe et al., *Methods* 61:23-29, 2013; Leng et al., *J Gerontol A Biol Sci Med Sci* 63:879-884, 2008). The concentrations of interleukin (IL)-6, IL-8 and IL-12p40 were measured by V-PLEX™ (MSD), using the manufacture's protocol. The assays for IL-6R, soluble CD14 (sCD14), sCD21, sCD23, sCD27, sCD163, and CXCL13 were newly developed. All samples were run in duplicate, except IL-6, IL-8, and IL-12p40. Each assay contained additional reference samples (minimum of 2) on each plate to check the intra- and inter-assays reliability.

The standard protocol for the developed assays was as follows—standard binding plates (MSD, L15XA) were coated with 30 al of working solution of capture antibody and stored at 4° C. overnight. The next morning, the coating solution was aspirated, and plates were blocked with 150 al of 1% bovine serum albumin (BSA) in phosphate buffered saline (PBS) for 2 hours at room temperature on a shaker at 200 rpm. After washing plates three times with PBS-Tween-20 (PBS-T), 25 al of sample was added to each well, and the plates were incubated for two hours at room temperature on a shaker at 200 rpm. Plates were washed again three times with PBS-T. Twenty-five µl of working solution of detection antibody was added to each well, and the plates were incubated for two hours at room temperature on a shaker at 200 rpm. The plates were then washed three times with PBS-T and incubated one hour with 25 µl of 0.25 ag/ml Sulfo-tag labeled streptavidin solution (MSD, R32AD). Finally, plates were washed three times with PBS-T and 150 al of 2 fold-concentrated Read Buffer (MSD, R92TC) was added for the SI2400 image analyzer (MSD). The standard curve was generated from a serial dilution of standards proteins in 1% BSA in PBS. The details of the reagents, manufacturer, detection limits and intra-assay coefficients of variance are depicted in Table 1.

TABLE 1

Methodological details of biomarker measurements

| Molecule | Manufacturer (Antibodies/Kit) | CSF dilution factor | Detection limit[a] | Intra-assay variation[b] | Inter-assay variation[b] |
|---|---|---|---|---|---|
| IL-6 | MSD (K15049D) | 1 | 0.74 pg/mL | 6.4% | 9.6% |
| IL-6Ra | R&D systems (MAB227, BAF227) | 10 | 6.3 pg/mL | 2.2% | 4.0% |
| IL-8 | MSD (K15049D) | 1 | 0.53 pg/mL | 6.7% | 9.8% |
| IL-12p40 | MSD (K15050D) | 1 | 4.6 pg/mL | 6.5% | 9.6% |
| sCD14 | R&D systems (MAB3833, BAF383) | 100 | 0.49 ng/mL | 2.9% | 6.8% |
| sCD21 | R&D systems (MAB4909, BAF4909) | 2 | 5.8 pg/mL | 3.0% | 6.8% |
| sCD23 | R&D systems (MAB1231, BAF123) | 2 | 16.0 pg/mL | 4.0% | 5.3% |
| sCD27 | Sanquin (M1960) | 20 | 0.4 U/mL | 2.3% | 2.9% |
| sCD163 | R&D systems (MAB16071, BAM16072) | 10 | 0.85 ng/mL | 2.7% | 5.8% |
| CXCL13 | R&D systems (MAB801, BAF801) | 1 | 17.4 pg/mL | 5.8% | 8.8% |
| CD4 | R&D systems (MAB379, BAF379) | 1 | 0.1 ng/mL | Not detectable in the CSF | |
| CD8 | Abnova (H00000925-M10, PAB16612) | 1 | n/a | Not detectable in the CSF | |
| CD19 | Abnova (H00000930-AP41) | 1 | 1 ng/mL | Not detectable in the CSF | |
| CD20 | Abnova (H00000931-AP22) | 1 | 1 ng/mL | Not detectable in the CSF | |
| GM-CSF | R&D systems (DY215) | 1 | 10 pg/mL | Not detectable in the CSF | |
| IFN-γ | MSD (K15049D) | 1 | 0.6 pg/mL | Not detectable in the CSF | |
| IL-7 | R&D systems (DY207) | 1 | 10 pg/mL | Not detectable in the CSF | |
| IL-10 | MSD (K15049D) | 1 | 0.6 pg/mL | Not detectable in the CSF | |
| IL-12p70 | MSD (K15049D) | 1 | 0.6 pg/mL | Not detectable in the CSF | |

[a] When diluted CSF was used, detection limit is recalculated to reflect utilized concentration factor;
[b] median value of concentration CV.

Assessment of Cellular Origin of Tested Biomarkers

Granulocytes, monocytes, B cells, T cell subsets, natural killer (NK) cells, and dendritic cells (DCs) were isolated via FICOLL™-gradient treated apheresis of three healthy donors (Table 2). Purified cells were cultured at density of 1×10⁶ cells/ml in serum-free X-VIVO 15 medium (Lonza) in the presence or absence of 10 μg/mL phorbol myristate acetate (PMA) and 1 μM ionomycin. Supernatants were collected after 48 hours and frozen until biomarker measurements. The concentration of biomarker per specific immune cell type was calculated using flow cytometry-derived purity data obtained before each cell culture.

TABLE 2

Details of cell isolation

| | Monocyte | B cell | CD4+ T cell | CD8+ T cell | NK cell | Myeloid DC |
|---|---|---|---|---|---|---|
| Isolation kit (Miltenyi Biotec) | 130-069-537 | 130-091-151 | 130-096-533 | 130-069-495 | 130-092-657 | 130-094-487 |
| Cell number per condition | $1 \times 10^6$/ml | $1 \times 10^6$/ml | $1 \times 10^6$/ml | $1 \times 10^6$/ml | $1 \times 10^6$/ml | $1 \times 10^6$/ml |

MRI and CEL Counting

Routine spin-echo and gradient-echo T1-weighted images were collected following intravenous administration of 0.1 mmol/kg gadopentetate dimeglumine as previously described (Bielekova et al., Neurology 65:1071-1076, 2005). CELs were quantified according to the consensus of two neurologists with neuro-immunology subspecialty training with reference to pre-contrast T1- and T2-weighted images.

Immunohistochemistry

Brain autopsy tissue sections from six non-immunocompromised cryptococcal meningo-encephalitis patients (different from patient included in the biomarker cohort) were analyzed by immunohistochemistry. Paraffin embedded sections were immuno-stained with CD3 (clone F7.2.38) mouse anti-human monoclonal antibody (Dako) and CD68 (clone KP1) mouse anti-human monoclonal antibody (Dako) and signal was detected by horseradish peroxidase (HRP)-conjugated—secondary antibody using chromogenic detection system.

Statistical Analyses

Figure 4:
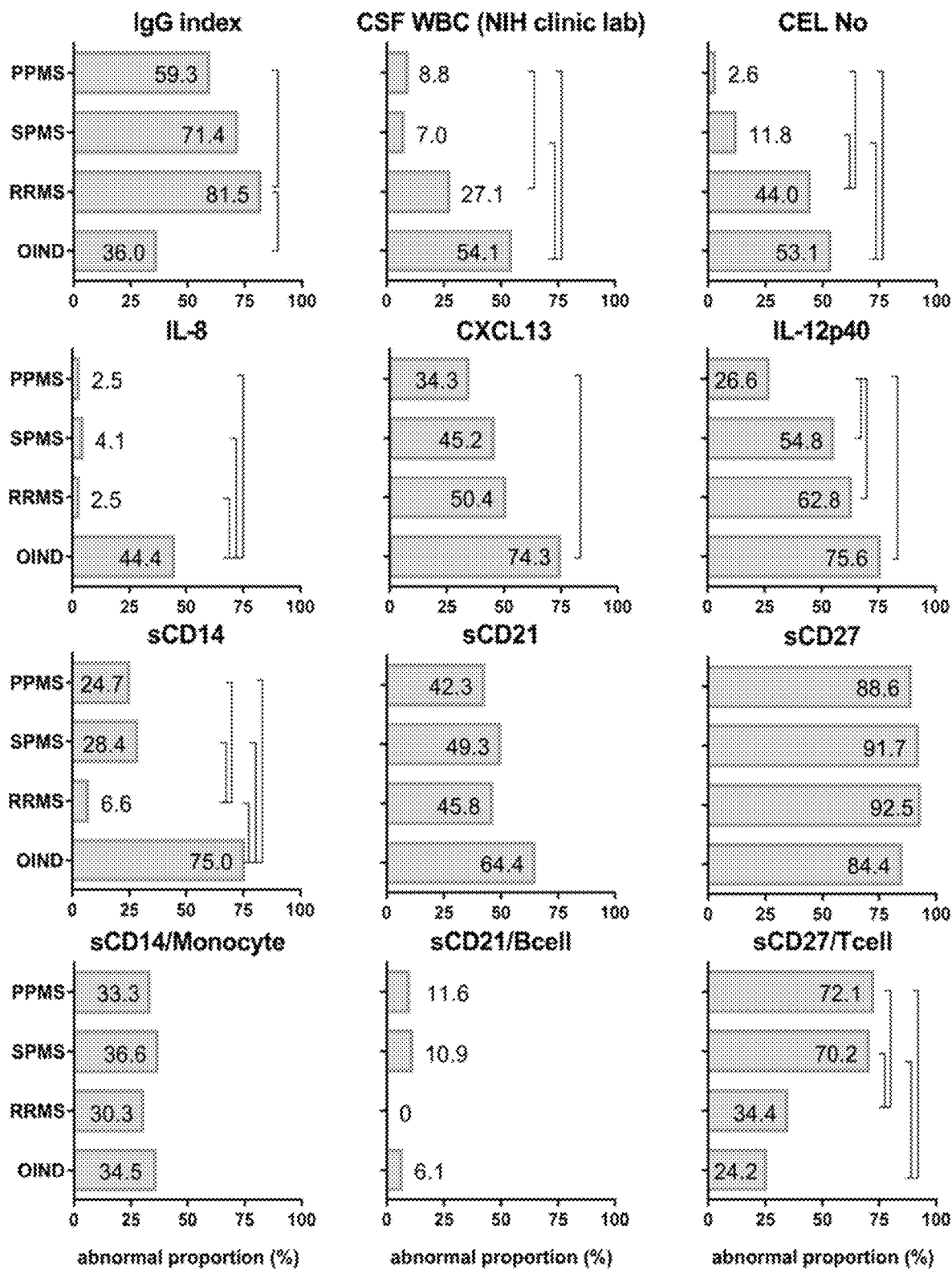
FIG. 4 is a series of graphs demonstrating that novel biomarkers provide clinical value in comparison to traditional biomarkers of intrathecal inflammation in distinguishing inflammatory subtypes. The continuous biomarkers were dichotomized using mean+2 SD or Q3+1.5 IQR (for "CEL No" only) as thresholds, where mean, SD, the third quartile (Q3) and interquartile range (IQR) were calculated from HD subjects' non-transformed data. The proportions of patients in four diagnostic categories of neuroimmunological disorders (PPMS, SPMS, RRMS and OIND) with abnormal values (greater than the threshold) are shown for traditional (IgG index, CSF white blood cells (WBC) and CEL No) or novel biomarkers (IL-8, CXCL13, IL-12p40, sCD14, sCD21, sCD27, sCD14/Monocyte, sCD21/B cell and sCD27/T cell). Fisher's exact test was used to evaluate the association between the dichotomized biomarkers and diagnosis variable. Black brackets highlight statistically significant differences (p<0.05) between four diagnostic categories, based on pair-wise multiple comparisons with Bonferroni correction.
Figure 5A:
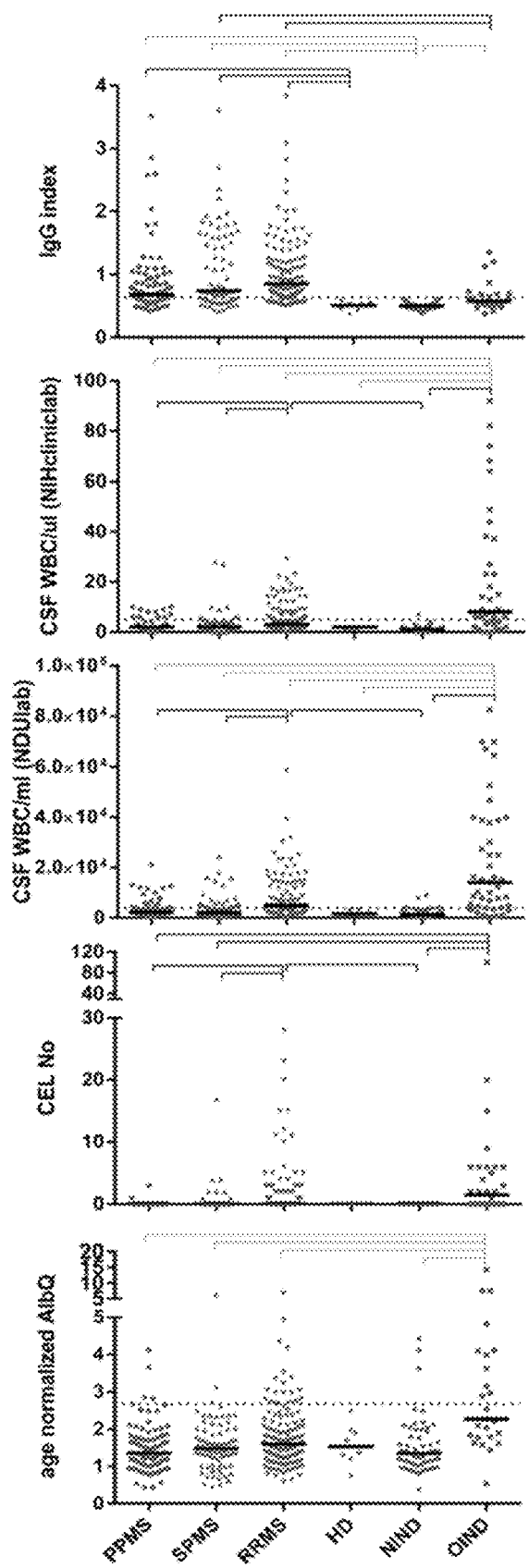
FIGS. 5A-5B are a series of graphs showing validation of traditional biomarkers for intrathecal inflammation. Traditional intrathecal inflammatory biomarkers, including IgG index, WBC counts in un-spun CSF (CSF WBC/µl) and on 50-fold concentrated CSF (CSF WBC/ml), the number of CEL on brain MRI performed at the time of lumbar puncture, and age normalized albumin quotient (AlbQ), were validated in coded CSF samples of combined Cohorts A and B (N=386, FIG. 5A). Age normalized AlbQ was calculated with the following formula: (measured AlbQ)/(age normal AlbQ). Age normal AlbQ was calculated with the following formula: $(4+ \text{age}/15) \times 10^{-3}$ (Reiber et al., *Fluids Barriers CNS* 9:17, 2012). Grey brackets represent statistical significance (p<0.01) that was reproduced only in one of the independent cohorts, whereas black brackets highlight those differences that reached statistical significance (p<0.05) in each independent cohort, based on the ANOVA and Tukey's correction method for pair-wise multiple comparisons. Dotted lines represent the upper limit of normal values (mean+2 SD) of HD for IgG index, CSF WBC (NDUlab), and age normalized AlbQ. For CSF WBC, the NIH clinical center normal limit (≤5 cell/µl) was utilized in the figure. For CEL number, zero was considered normal. Thick black bars represent the median for each diagnostic category.
Figure 5B:
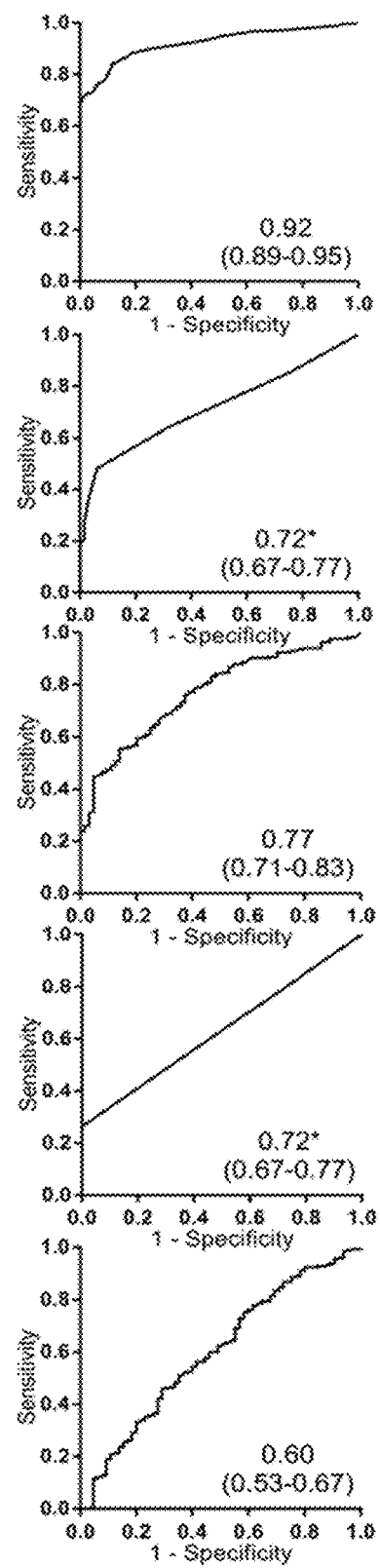

Since most of the variables did not follow the normal distribution, Box-Cox transformation was applied. To evaluate the association between biomarkers and diagnosis groups, one-way analysis of variance (ANOVA) and Fisher's exact test were performed. In the ANOVA, each continuous biomarker was tested for each of the three data sets: Cohort A, Cohort B, and the two cohorts combined, and for each of the two diagnosis variables, one with five categories (RRMS, PPMS, SPMS, NIND, HD, and OIND; for FIGS. 1 and 2), and the other with three categories (cyclic meningitis, cryptococcal meningo-encephalitis, and PPMS+SPMS; for FIG. 3). Tukey's correction was used for pairwise multiple comparisons. In Fisher's exact test, the continuous biomarkers were dichotomized using mean+2 standard deviation (SD) or Q3+1.5 IQR (for contrast-enhancing lesions number (CEL No) only) as thresholds, where mean, SD, the third quartile (Q3) and interquartile range (IQR) were calculated from HD subjects' non-transformed data. The diagnosis variable included four categories (RRMS, PPMS, SPMS, and OIND) in order to evaluate the performance of biomarkers in differentiating patients with different neuroimmunological diseases (FIG. 4). A Bonferroni correction method was used for multiple comparisons.

To evaluate the accuracy of the diagnostic test, the area under the receiver operating characteristic curve (AUC) and its 95% confidence intervals (CIs) were calculated using dichotomized diagnosis variables as binary outcomes: patients with—(OIND+PPMS+RRMS+SPMS) vs. without—(HD+NIND) intrathecal inflammation (for FIGS. 1 and 2) and patients with—(SPMS+PPMS) vs. without—(OIND+RRMS) compartmentalized intrathecal inflammation (FIG. 3). The correlation between biomarker variables was evaluated by Pearson correlation coefficients. SAS version 9.2 was used for above analyses.

Example 2: Biomarkers for Intrathecal Inflammation

This example describes the identification of protein biomarkers useful for identifying subjects with active meningeal inflammation and/or for distinguishing patients with progressive MS from patients with other inflammatory neurological diseases.

Results

After unblinding, the corresponding diagnostic categories in the two separate cohorts yielded consistent results for all reproducibly measured biomarkers. Therefore, data is provided for each cohort in FIGS. 6 and 7, while FIGS. 1 and 2 show results for all patients, highlighting statistically-significant differences reproduced in both cohorts.

Figure 6A:
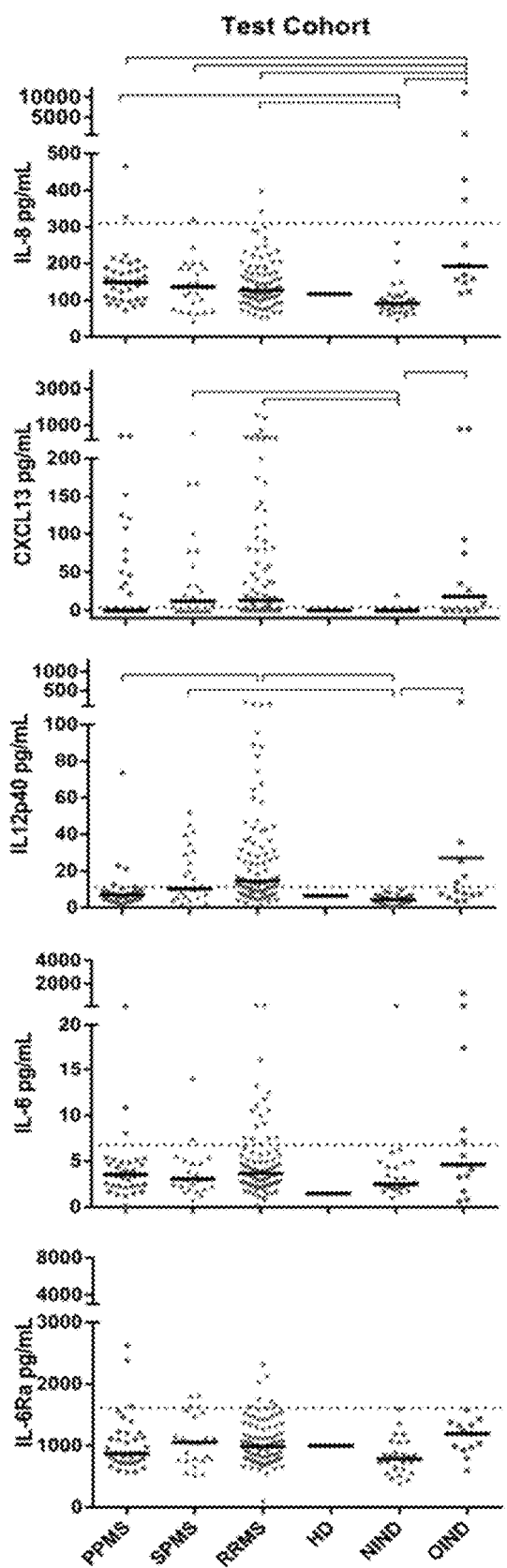
FIGS. 6A-6B are a series of graphs showing concentrations of cytokines and chemokines in Cohorts A and B. Candidate biomarkers (IL-8, CXCL13, IL-12p40, IL-6 and IL-6Ra) from the cytokine/chemokine category were quantified using commercially-available, or newly developed electrochemiluminescence sandwich immunoassays in coded CSF samples of Cohorts A (N=193, FIG. 6A) and B (N=193, FIG. 6B). Black brackets highlight those differences that reached statistical significance (p<0.05), based on pair-wise multiple comparisons with Tukey's correction method. Dotted lines represent the upper limit of normal values calculated as mean+2 SD using HD values. Thick black bars represent the median for each diagnostic category.
Figure 6B:
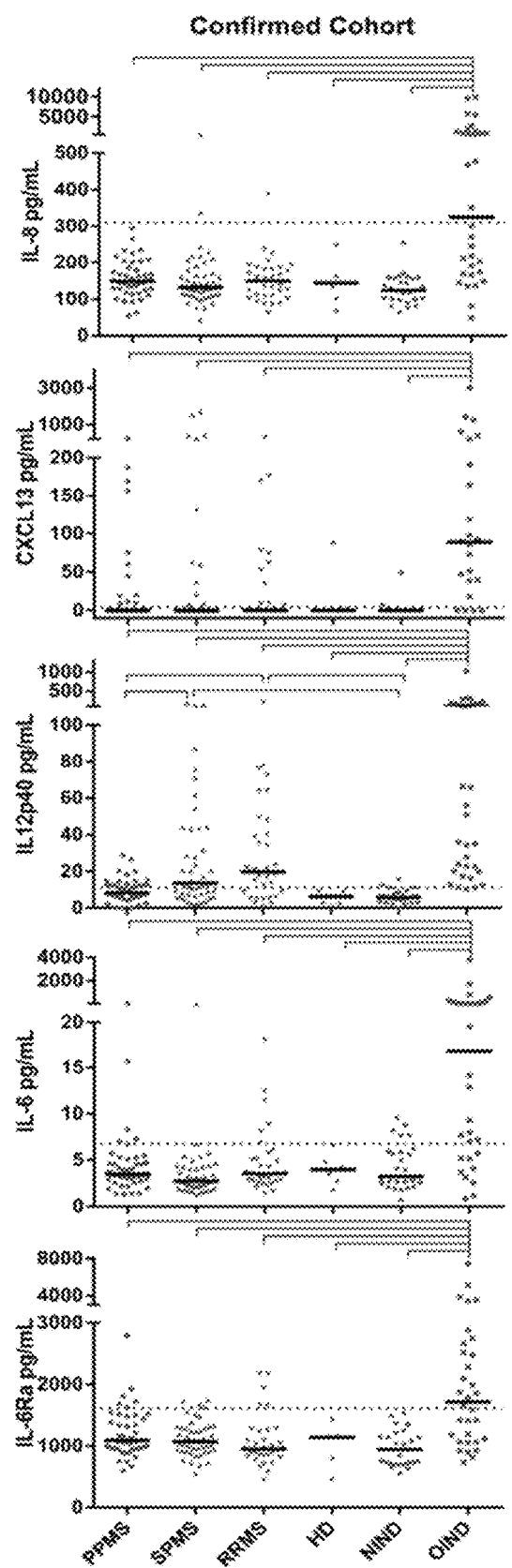

Among Cytokines and Chemokines, IL-12p40 and IL-8 Consistently Differentiate Inflammatory from Non-Inflammatory Subgroups The chemokine IL-8, mainly produced by activated cells of the innate immune system (FIG. 1A), consistently differentiated other inflammatory neurological diseases (OIND) from all other diagnoses (FIG. 1B and FIG. 6). The chemokine CXCL13, secreted by activated T cells and DCs, was also dependably elevated in OIND patients, while its increased levels in RRMS and SPMS did not reach significance in the second cohort. Of the cytokines tested, IL-6 and its soluble receptor (IL-6Ra) were ubiquitously produced by different immune cells. These related markers were elevated only in OIND in the confirmatory cohort. On the other hand, IL-12p40, released by activated DCs and, to lesser degree by activated CD8+ T cells and B cells, was consistently elevated in OIND, RRMS and SPMS cohorts. Furthermore, IL-12p40 differentiated PPMS from RRMS and SPMS.

Figure 2A:
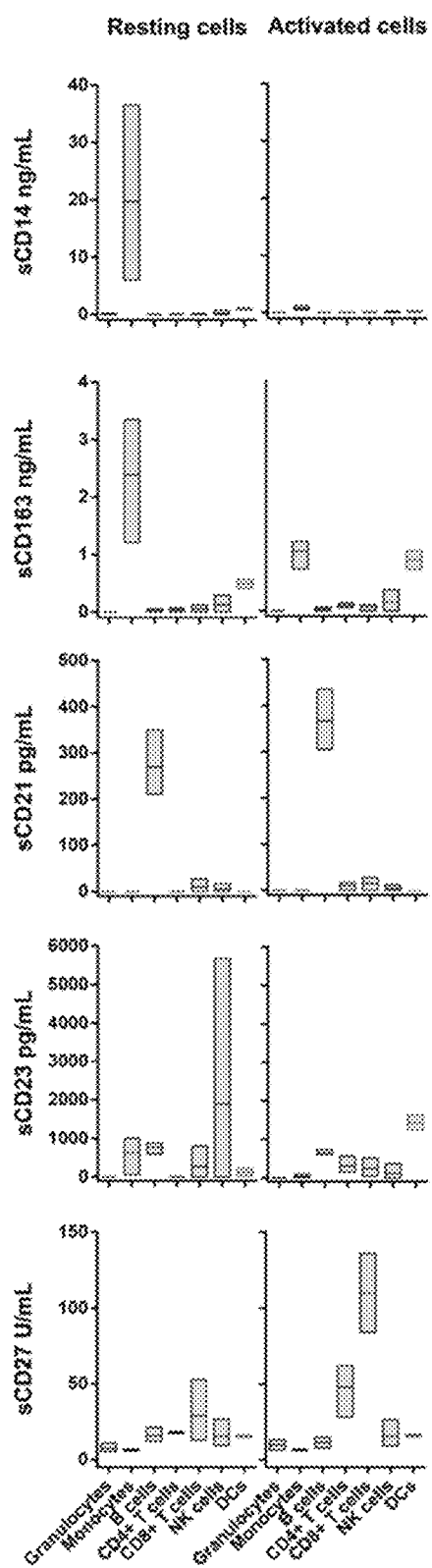
FIGS. 2A-2C are a series of graphs demonstrating that cell surface markers have more restricted cellular origin and sCD27 is a biomarker of intrathecal (T cell-mediated) inflammation. Candidate biomarkers (sCD14, sCD163, sCD21, sCD23 and sCD27) from cell surface markers were quantified using newly developed electrochemiluminescence sandwich immunoassays in cultured supernatants from purified, negatively-selected immune subtypes (FIG. 2A) or coded CSF samples from combined cohorts A and B (N=386, FIG. 2B). Purified granulocytes, monocytes, B cells, CD4+ and CD8+ T cells, NK cells and DCs ($1 \times 10^6$/ml) from HD (N=3) were either left untreated (FIG. 2A, left) or polyclonally stimulated with PMA/ionomycin (FIG. 2A, right) for 48 hours before collection of supernatants. Biomarker concentrations were re-calculated per million cells of each specific subtype using flow cytometry data for purity of each seeded culture.
Figure 2B:
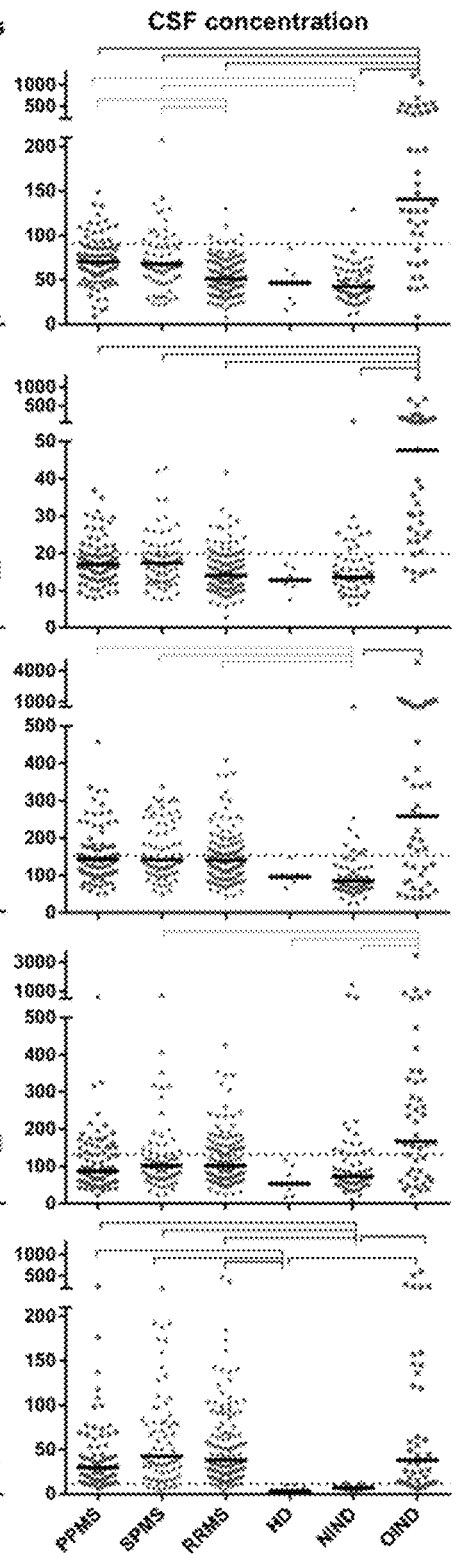
Figure 2C:
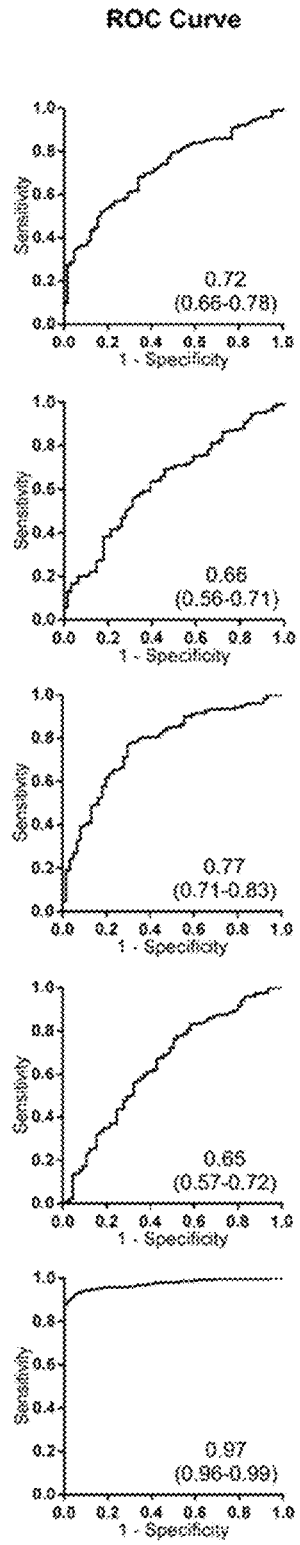

Soluble Surface Markers have Restricted Cellular Origin and Provide Added Clinical Value While sCD14 is a specific monocyte marker, sCD163 is released by both monocytes and DCs in resting and activated states (FIG. 2A). Consequently, sCD14 and sCD163 were highly correlated ($r_{Pearson}$=0.80, p<0.0001) and reproducibly differentiated OIND from other diagnoses (FIG. 2B and FIG. 7). Although sCD14 was also elevated in progressive MS in comparison to non-inflammatory neurological disease (NIND) patients in both cohorts, the difference in the confirmatory cohort did not reach statistical significance.

Figure 8:
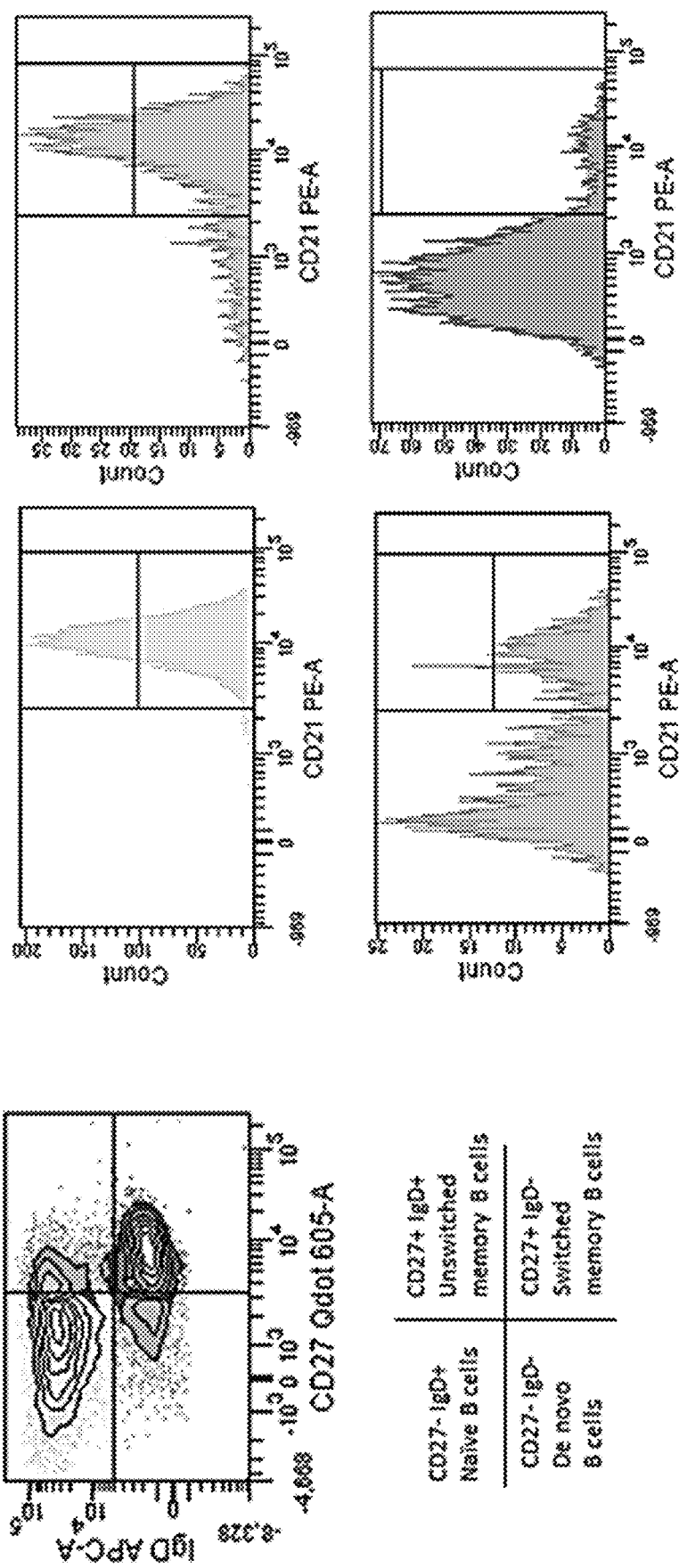
FIG. 8 is a series of flow cytometry plots showing CD21 expression on B cells. Fresh blood samples derived from multiple sclerosis patients or healthy donors were processed for flow cytometry and stained with CD19, CD20, CD21, CD27, CD45, IgM and IgD. The left upper panel demonstrates expression of CD27 and IgD on CD19+/CD20+ peripheral blood B cells, and divides peripheral B cells into naïve B cells (IgD+/CD27−), un-switched memory B cells (IgD+/CD27+), switched memory B cells (IgD−/CD27+) and double negative B cells (IgD−/CD27−). Color-coded histograms demonstrated CD21 expression on these progressively-differentiated B cells. Representative images from a single donor are depicted; no significant differences in CD21 expression on B cells during their differentiation cycle were observed between MS patients and HD.
Figure 9A:
FIGS. 9A-9D are images showing monocytes/macrophages and T cell infiltration of cryptococcal meningo-encephalitis brain autopsy tissue. The images show brain autopsy tissue staining from a representative patient with cryptococcal meningo-encephalitis.
Figure 9B:
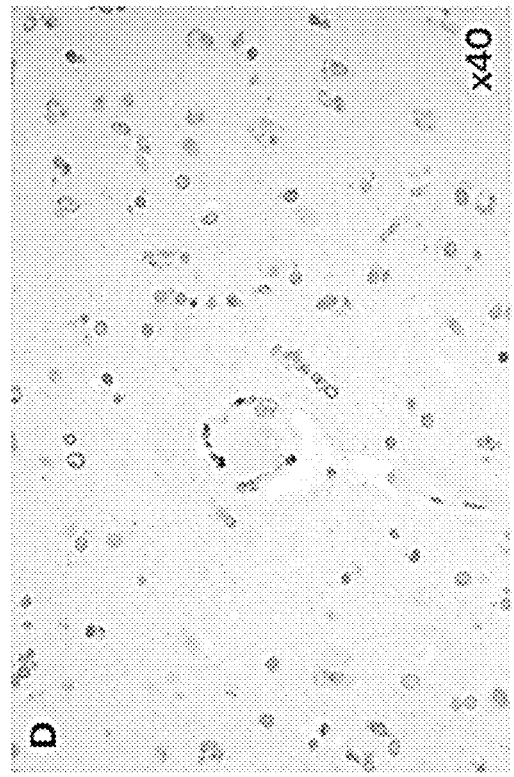
Figure 9C:
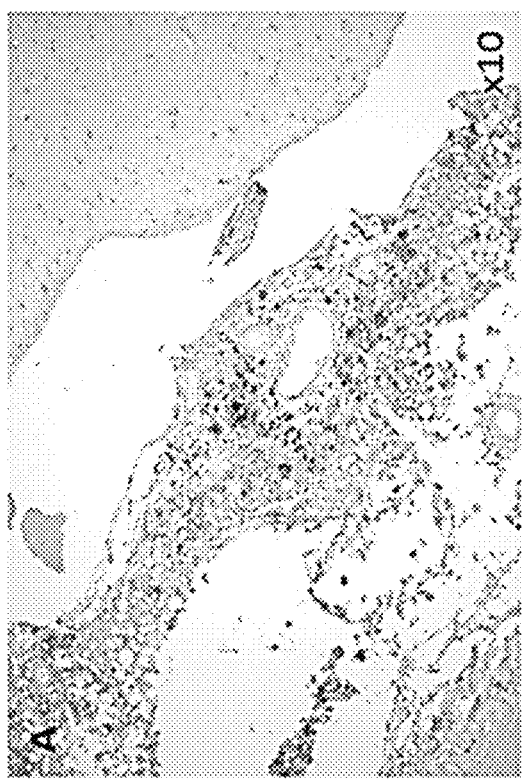
Figure 9D:
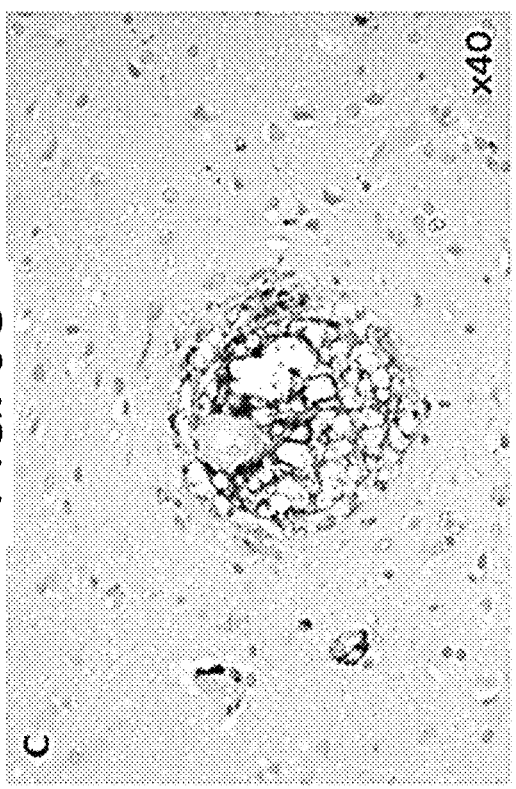
Figure 11A:
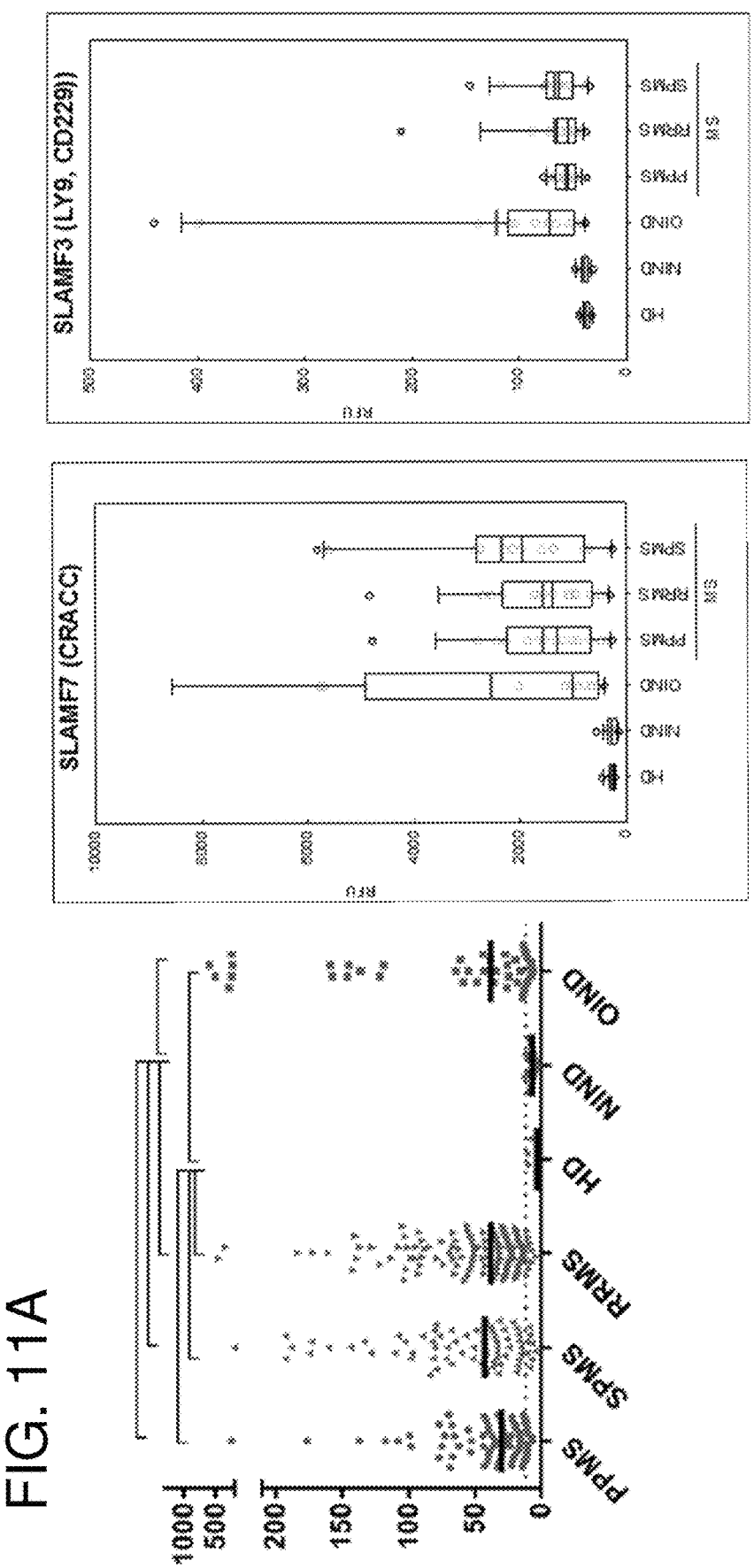
FIGS. 11A-11B are a set of graphs showing CSF levels of biomarkers that differentiate inflammatory neurological diseases (OIND, MS) from non-inflammatory neurological diseases.
Figure 11B:
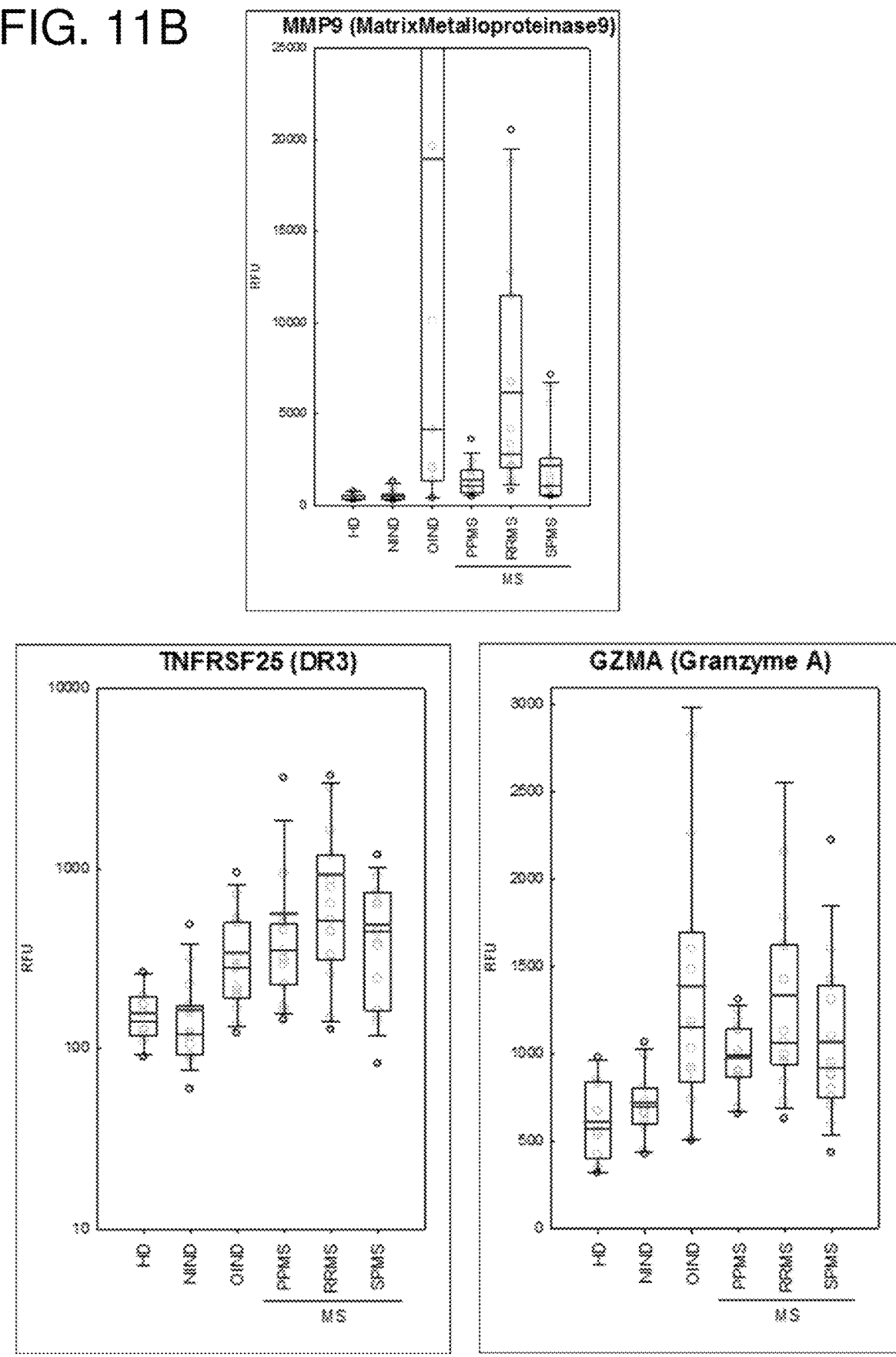
Figure 12A:
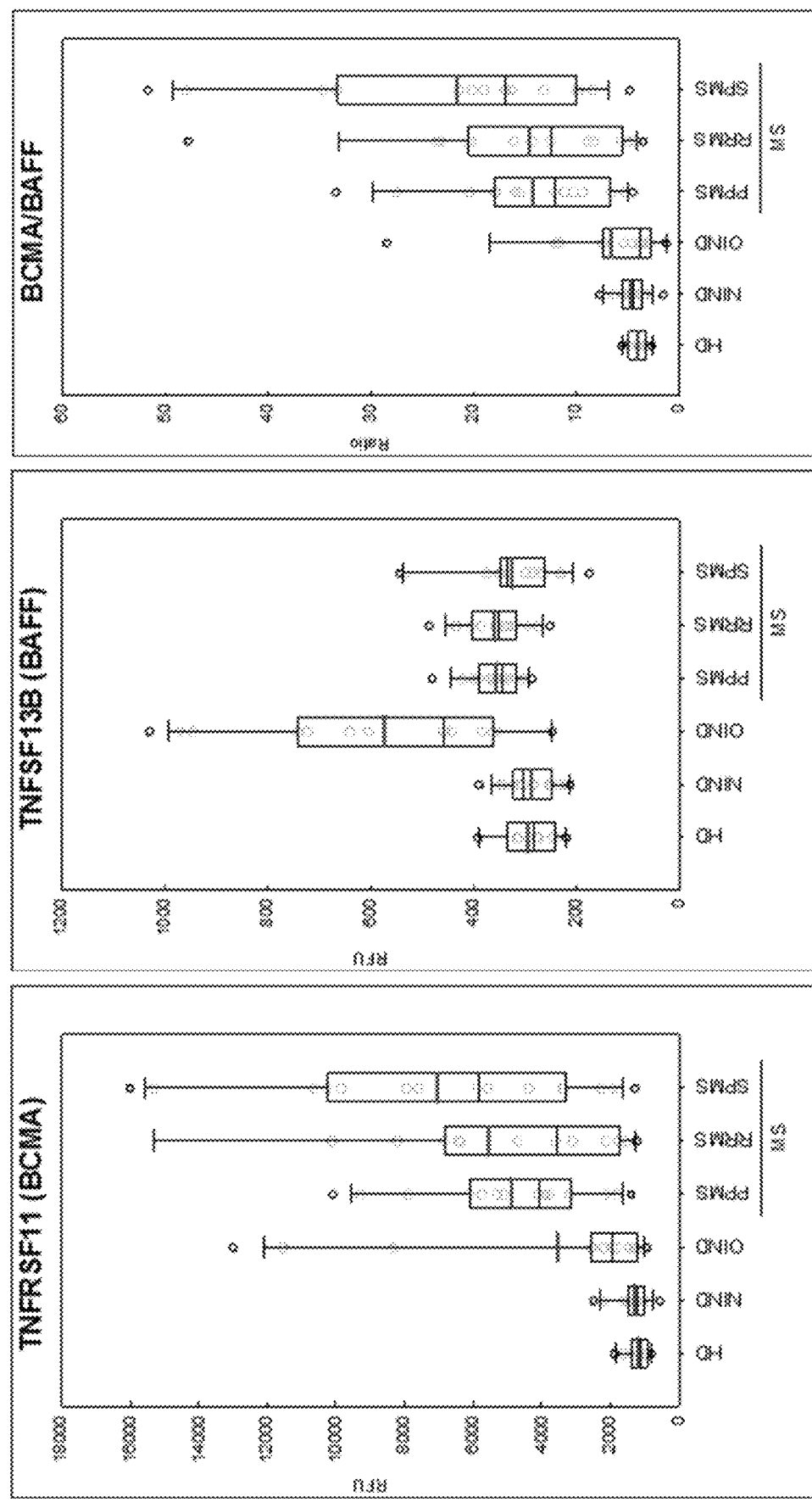
FIGS. 12A-12B are a set of graphs showing CSF levels of biomarkers that differentiate inflammatory (OIND, MS) from non-inflammatory neurological diseases, but are also capable of discriminating between OIND and MS.
Figure 12B:
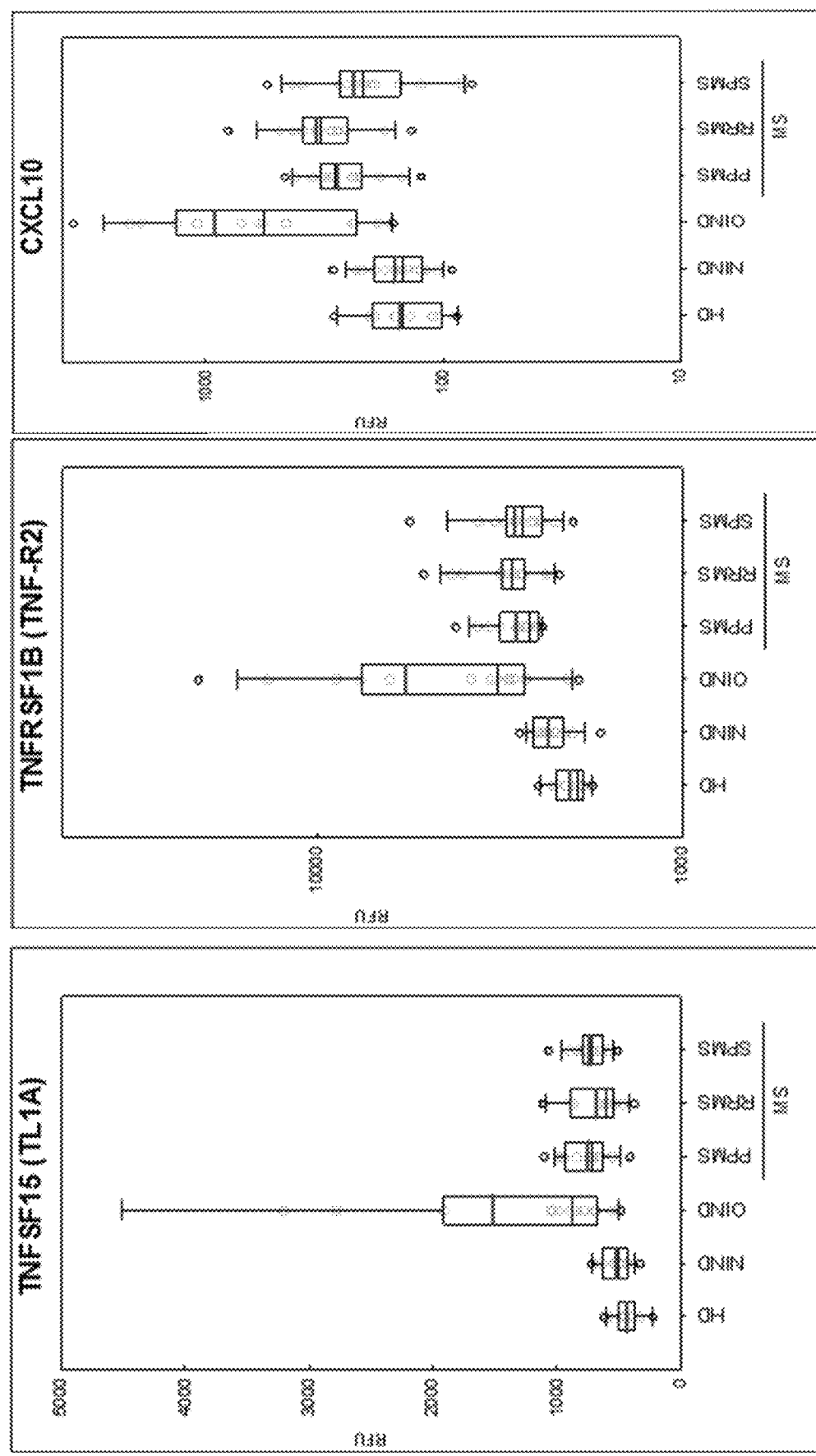
Figure 13A:
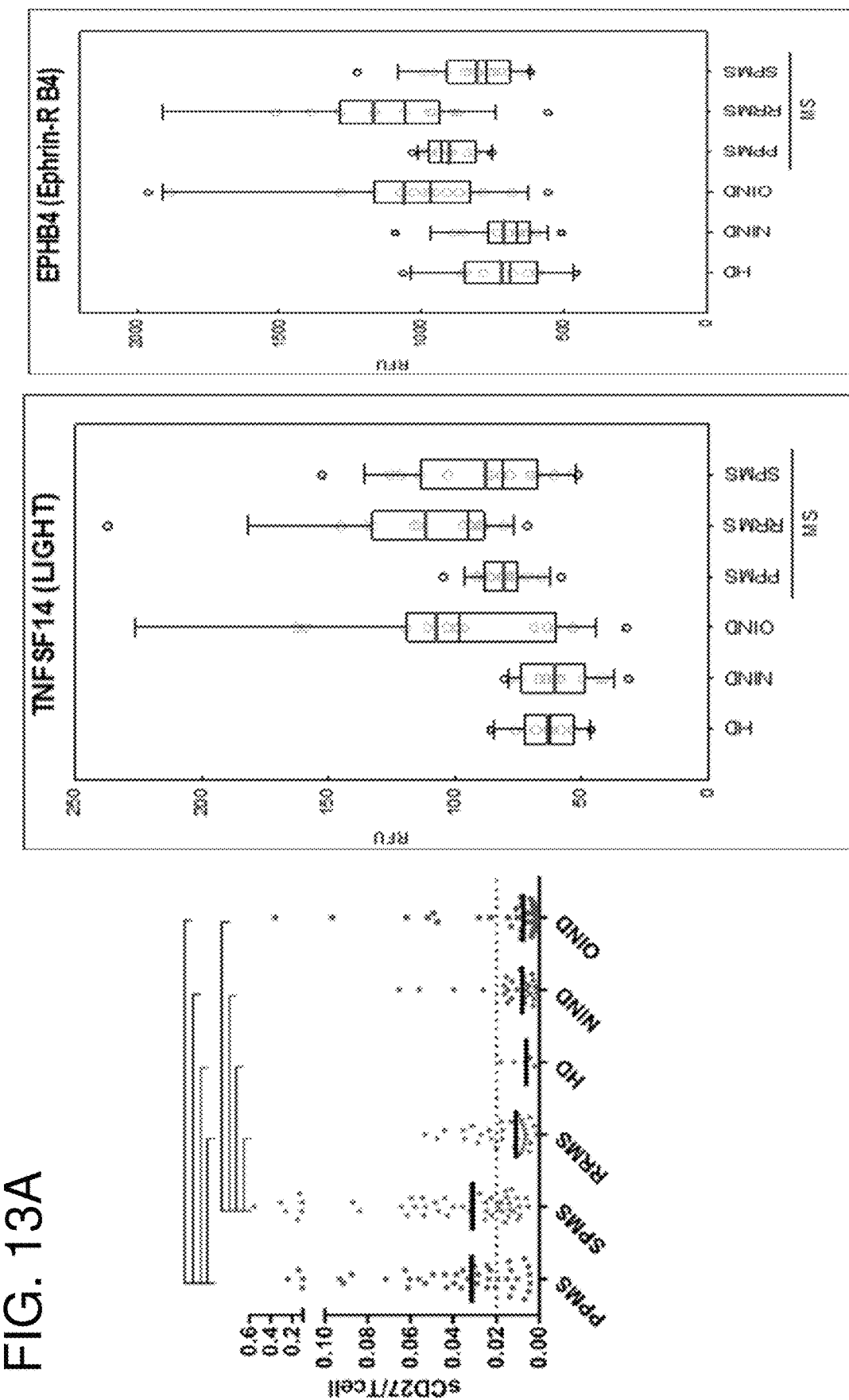
FIGS. 13A-13D are a set of graphs showing CSF levels of biomarkers that differentiate RRMS from progressive MS subtypes.
Figure 13B:
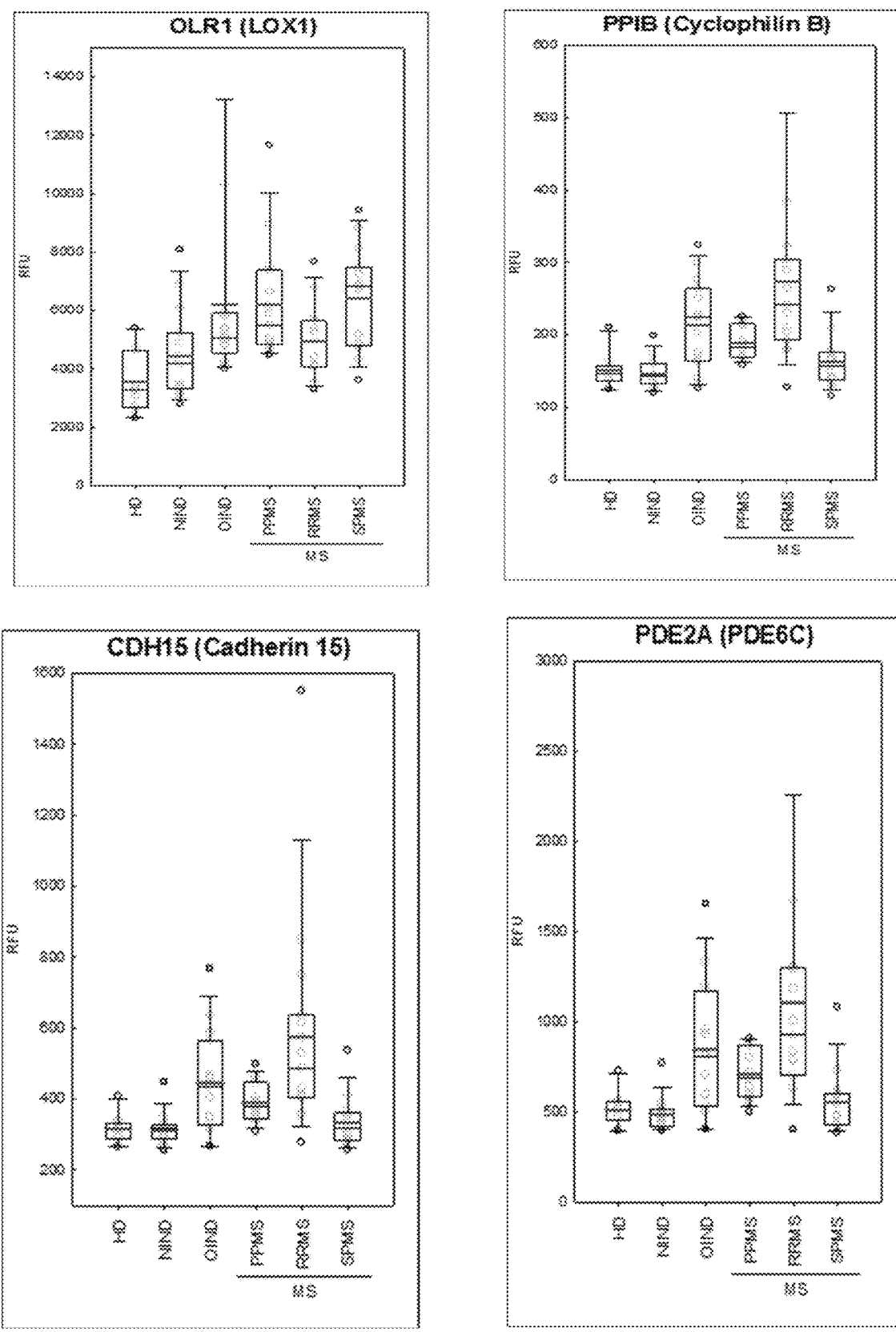
Figure 13C:
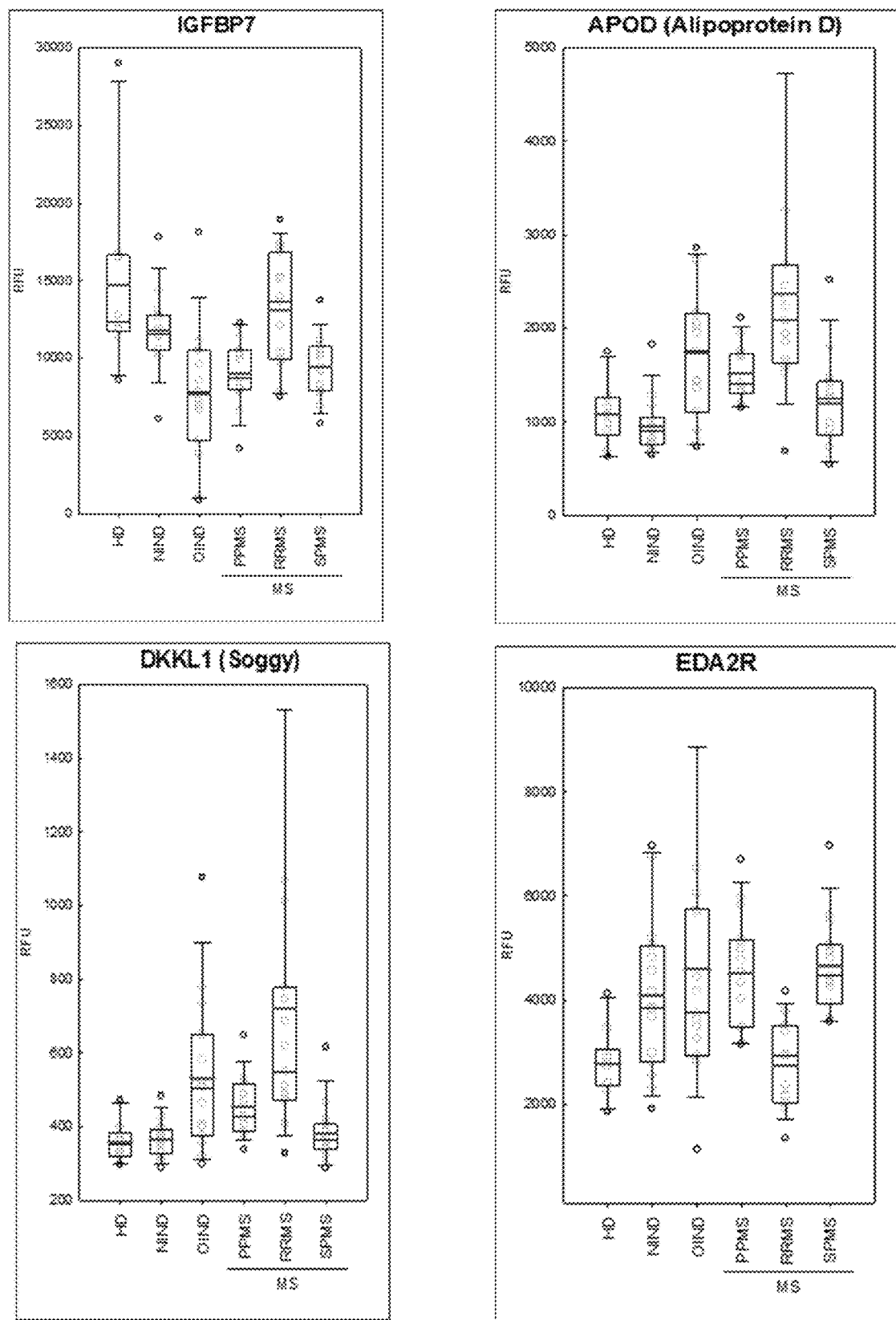
Figure 13D:
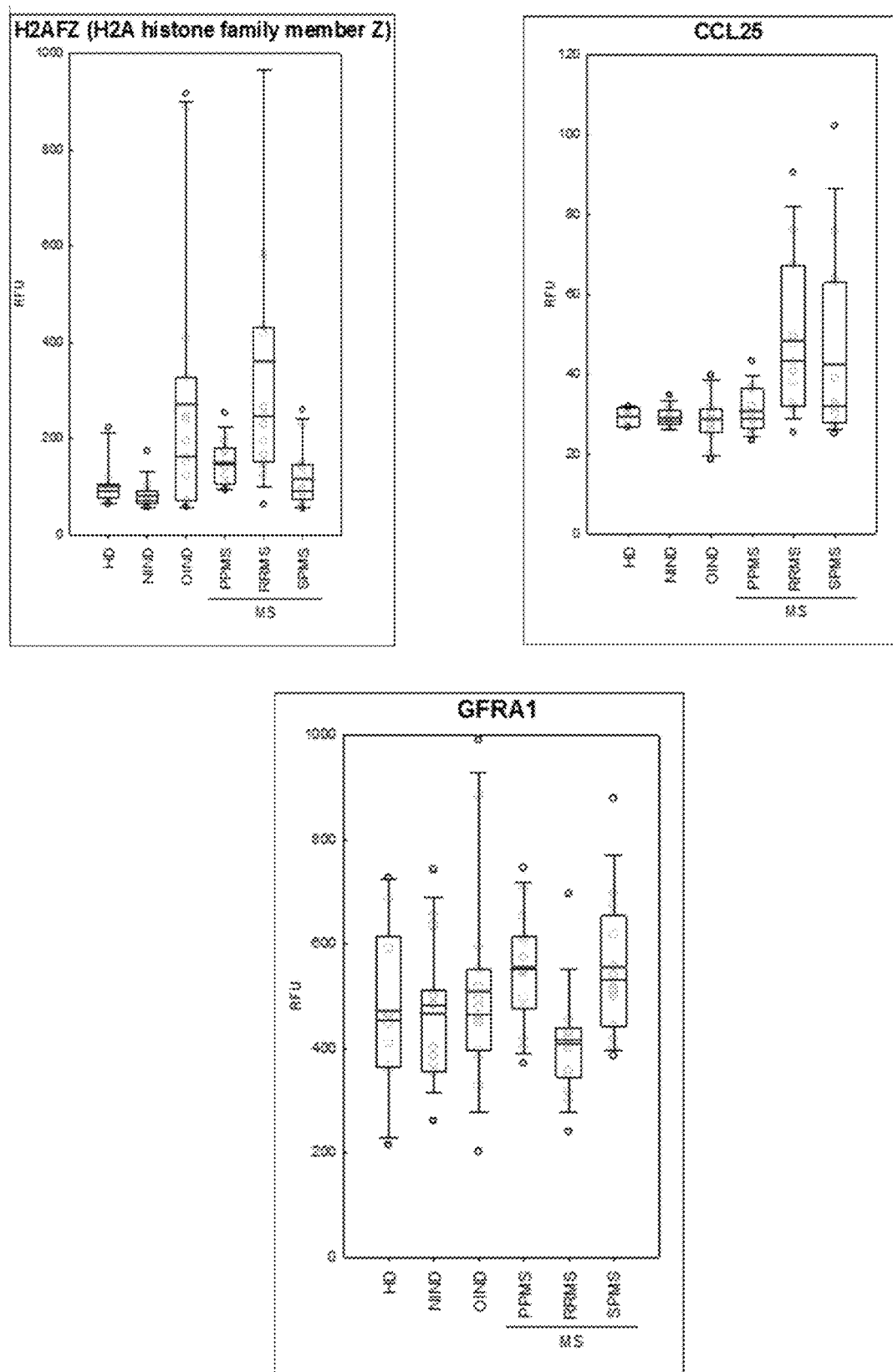
Figure 14A:
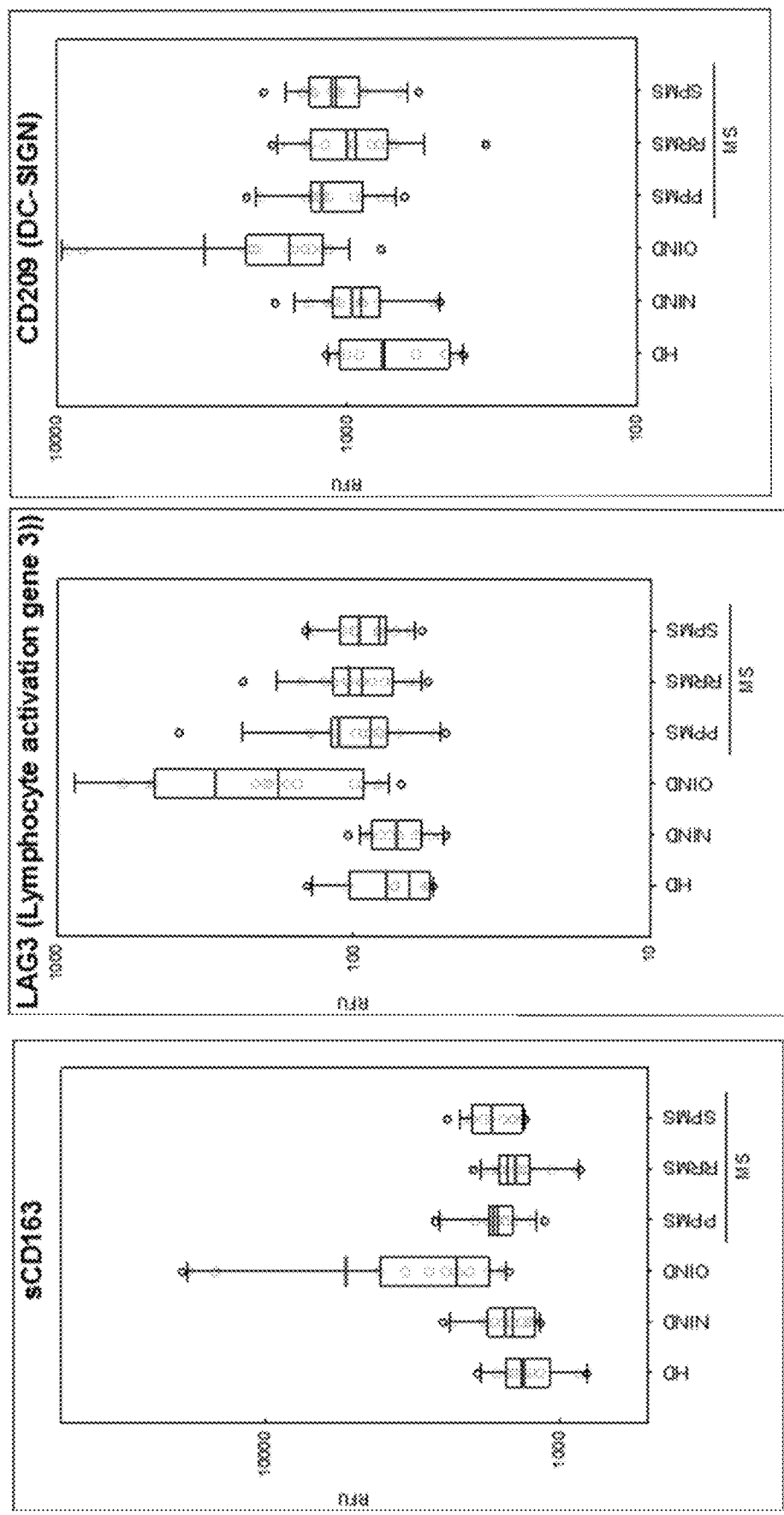
FIGS. 14A-14B are a set of graphs showing CSF levels of biomarkers that differentiate OIND from all other categories (HD, NIND, PPMS, RRMS and SPMS).
Figure 14B:
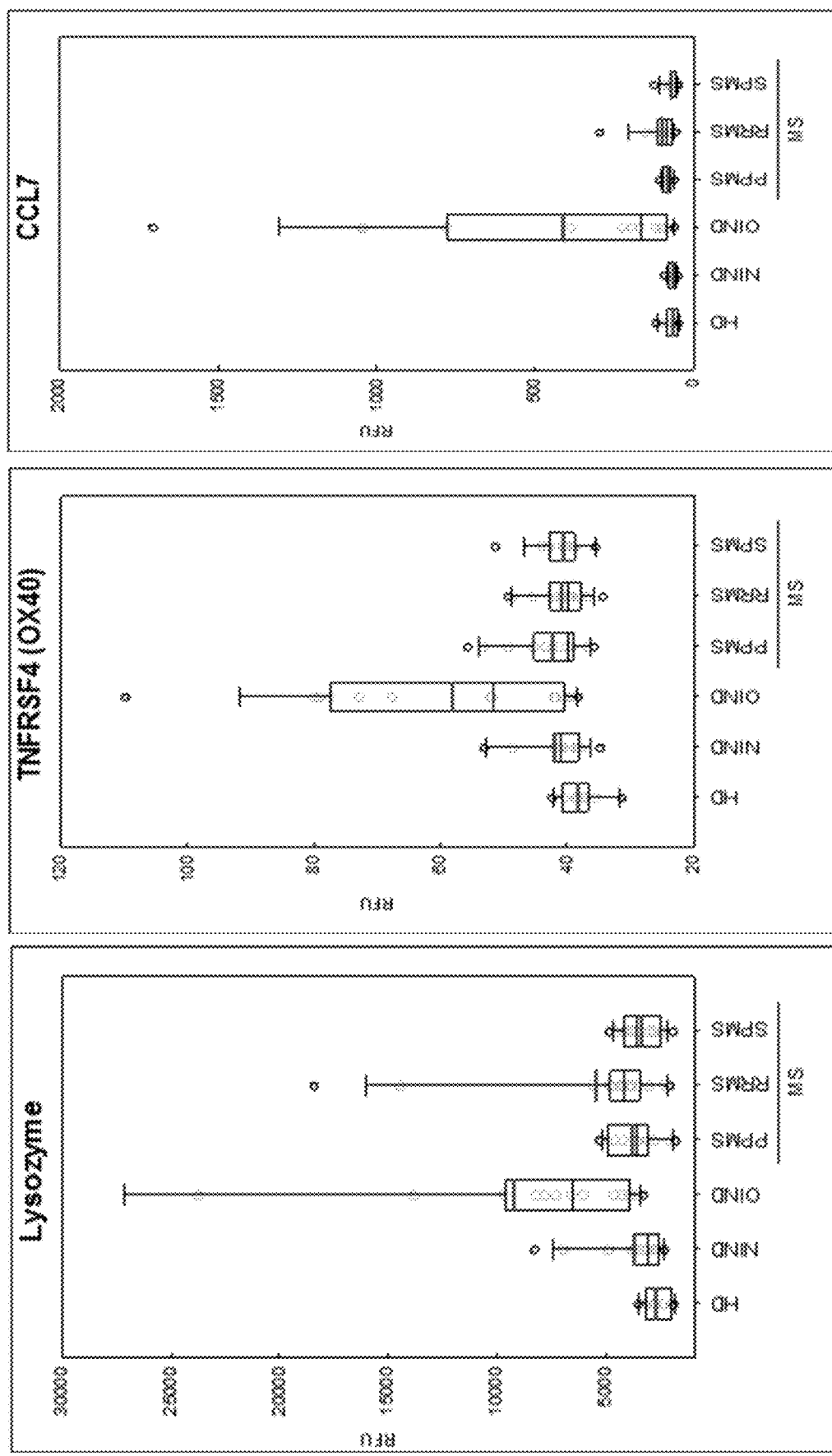
Figure 15A:
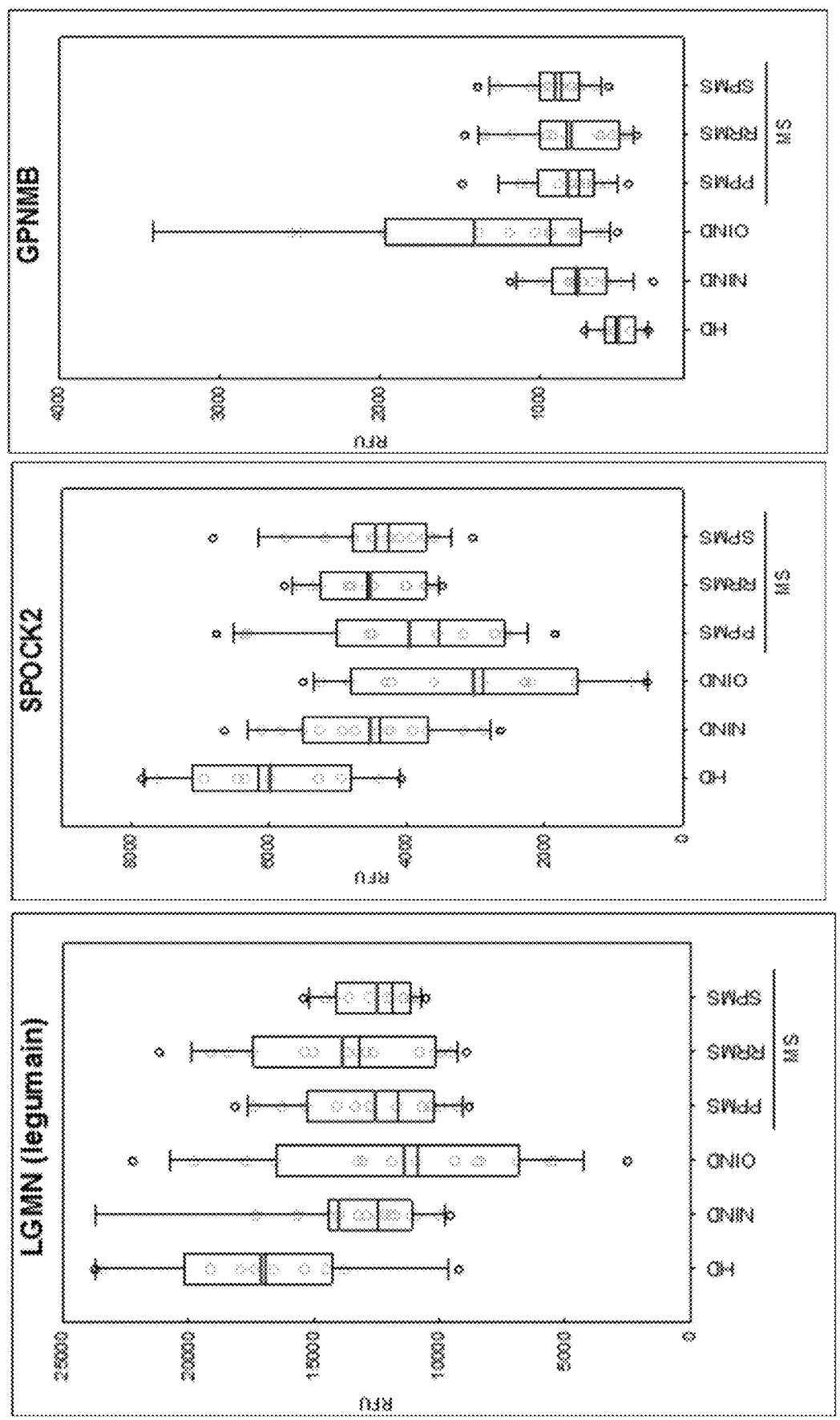
Figure 15B:
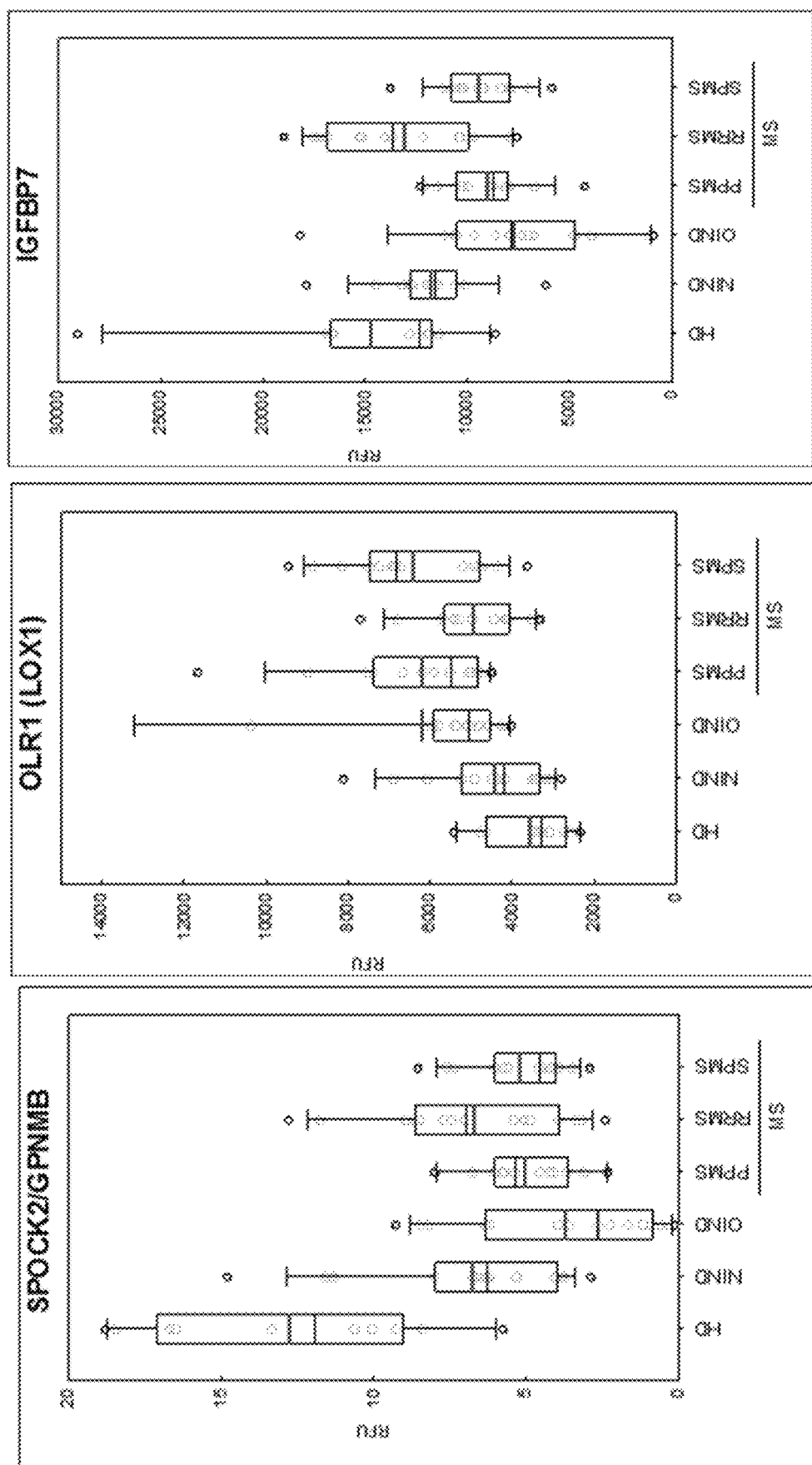

Soluble CD21 is a selective biomarker of B cells released in resting and activated states (FIG. 2A). While its levels were elevated in both OIND and all MS groups in comparison to NIND, the only statistically significant difference in the confirmatory cohort occurred between OIND and NIND (FIG. 2B and FIG. 7). In view of the confirmation that CD21 expression on B cells decreases during their differentiation (FIG. 8), it became desirable to develop a better B cell-specific biomarker by measuring sCD19, sCD20 and sCD23. Whereas CSF levels of sCD19 and sCD20 were below the detection limit of the assays (Table 1), sCD23 was released by many cell types and consequently, lacked discriminatory power (FIG. 2).

Though expressed by several cell types (especially T and B cells), sCD27 was secreted in large quantities only by activated T cells, CD8>CD4. Soluble CD27 reproducibly differentiated all neuroimmunological diseases from NIND and HD with an exceptional AUC score (0.97) and CI (0.96-0.99) (FIG. 2).

Combined Biologically-Related Biomarkers Yields Insight about Immune Responses in CNS Tissue CSF inflammatory biomarkers are released from all intrathecal immune cells including those in the CSF and CNS tissue. Because HDs lack pathological immune infiltration of CNS, the ratio of cell-specific biomarkers to CSF-resident cells in HDs provides a range of physiological secretion by mobile, CSF immune cells. Ratios higher than the HD range imply that CSF cells cannot fully account for the biomarker measured. The excess of soluble biomarkers suggests a pool of intrathecal immune cells embedded in the CNS tissue and therefore unaccounted for by CNS immunophenotyping.

To test this hypothesis, three combinatorial biomarkers were calculated in Cohort B: ratios of sCD14/monocyte, sCD21/B cell and sCD27/T cell, each measured per ml of CSF (FIG. 3A). It was observed that the sCD14/monocyte ratio did not distinguish diagnostic groups, whereas the sCD21/B cell and especially sCD27/T cell ratios did. The sCD27/T cell ratio was significantly higher in progressive MS patients compared to all other diagnostic groups (FIGS. 3A-3B). Because OIND is a heterogeneous category, two diagnostically homogeneous groups were extracted to test the biological relevance of the inference (FIGS. 3C-3D). Patients with cyclic meningitis suffer from years of cyclic headaches and meningeal signs, but do not accumulate neurological disability. Immuno-competent patients with cryptococcal meningo-encephalitis have prominent CSF pleiocytosis, and some also have CNS infiltration by immune cells as evidenced by brain MRI abnormalities and neurological dysfunction. Both meningitis cohorts had elevated sCD14, sCD21 and sCD27 levels in comparison to progressive MS. Yet, the first group had normal combinatorial ratios, demonstrating that their CSF cells fully accounted for the production of soluble biomarkers. In contrast, the sCD14/monocyte ratio was elevated in the majority of cryptococcal meningo-encephalitis patients, indicating that the excessive portion of CSF sCD14 likely originated from monocytes/microglia in the CNS. Some of these patients also had increased sCD27/T cell ratios, suggesting CNS accumulation of T cells. Indeed, dominant monocyte/microglial activation and variable T cell infiltration are characteristics of brain autopsy specimens of immunocompetent patients with cryptococcal meningo-encephalitis (FIG. 9).

Novel Inflammatory Biomarkers Differentiate Patients with Diverse Phenotypes of Intrathecal Inflammation Finally, the existing quantitative markers and novel biomarkers were compared in their ability to differentiate subtypes of neuroimmunological diseases by quantifying differences in the proportions of patients with abnormal values (FIG. 4). Only novel markers (IL-12p40) differentiated between progressive MS subtypes and reliably differentiated OIND from all MS categories (sCD14, sCD27/T cell).

Clinical Applications

Out of 19 candidate biomarkers (Table 1), 10 were detectable in CSF. Shed surface markers had restricted cellular origin in comparison to cytokines/chemokines. Although CXCL13 was previously considered the most useful novel biomarker in MS (Sellebjerg et al., *Neurology*

73:2003-2010, 2009; Comabella and Montalban, *Lancet Neurol* 13:113-126, 2014; Khademi et al., *Mult Scler* 17:335-343, 2011; Krumbholz et al., *Brain* 129:200-211, 2006), IL-12p40 has a partially overlapping cellular origin, is detectable in all CSF samples and differentiates among MS subtypes. Thus, the present studies indicate that IL-12p40 is the most valuable biomarker among cytokines/chemokines. In addition to IL-12p40, IL-8 is useful in distinguishing MS from OIND patients.

The data disclosed herein demonstrates that sCD27 is the best biomarker of active intrathecal inflammation. Although expressed on multiple immune cells, sCD27 is shed in the highest concentrations by activated T cells. In light of the numerical predominance of T cells in the CSF, the contributions from alternative sources are negligible. The correlation between sCD27 levels and absolute numbers of CSF T cells ($r_{Pearson}$=0.52, p<0.0001) supports the conclusion that sCD27 is an excellent biomarker of T cell mediated inflammation.

Though the AUC score of other cell surface markers were smaller than that of sCD27, sCD21 and sCD14 provide information about immune phenotype. Despite the selective release of sCD21 by B cells, its expression decreases during the maturation process. Consequently, while high sCD21 levels indicate intrathecal expansion of B cells, normal sCD21 values do not exclude it. Hence, its specificity for B cells makes sCD21 a useful pharmacodynamic marker for B cell-depleting therapies and in personalized medicine paradigms.

Soluble CD14 is selectively released by monocytes, possibly during the differentiation process. Because activated microglia also express CD14 (Ulvestad et al., *J Neuropathol Exp Neurol* 53:492-501, 1994), it may be the main producer of CSF sCD14. The weak correlation between sCD14 levels and CSF monocyte counts ($r_{Pearson}$=0.27, p=0.0002) supports this interpretation. Accordingly, elevated sCD14 and especially sCD14/monocyte ratio represent novel markers of microglial activation. As microglial activation has been reported in many (including non-inflammatory) conditions and aging (Luo et al., *Mol Neurodegener* 5:12, 2010; Olsson et al., *JAlzheimers Dis* 33:45-53, 2013), it is noteworthy that ~30% of patients with all diagnoses have elevated sCD14/monocyte ratios, and that age explains some of this biomarker's variance ($r_{Pearson}$=0.33, p<0.0001).

A few OIND subjects in the present study with normal sCD27 levels comprised all enrolled patients with Susac's and Aicardi-Goutieres syndromes (AGS). Susac's syndrome is a microangiopathy affecting the CNS, retina and cochlea. While lymphocytic infiltration has been observed, it predominantly involves the arteriolar wall (Kleffner et al., *J Neurol Sci* 322:35-40, 2012). The data disclosed herein suggest that the pathophysiology of Susac's syndrome, in striking contrast to MS, is not associated with prominent intrathecal T cell activation. Similarly, while high CSF levels of interferon-c were recognized years before genetics identified defects in nucleic acid processing as the pathogenic pathway of AGS (Lebon et al., *J Neurol Sci* 84:201-208, 1988), the present data refute intrathecal T cell activation in this disease. Consistent with the activation of components of the innate immune system including DCs (Han et al., *J Immunol* 192(6):2551-2563, 2014), AGS patients had elevated CSF IL-6, CXCL13 and IL-12p40 levels. The observed groupings of patients with these rare diseases demonstrate the potential of the novel biomarkers to provide mechanistic understandings.

While current clinical practice evaluates each laboratory test in isolation, thoughtful combination of biologically related measurements can lead to new insight. Investigating the cellular origin of biomarkers is the simplest application of this systems biology principle. Thus, comparing the numbers of CSF cells with the marker(s) they secrete reveals information about immune cells embedded in CNS tissue. This concept is biologically credible based on the observed ability of these combinatorial biomarkers to differentiate patients with aseptic meningitis with low accumulation of disability from patients with (cryptococcal) meningo-encephalitis, and patients with RRMS from progressive MS. High CSF sCD27 levels (comparable to RRMS and OIND) and selective elevation of sCD27/T cell ratio indicate that T cell infiltration of the CNS is a hallmark of progressive MS. This finding contradicts the prevailing notion that inflammation no longer plays a pathogenic role in progressive MS, deduced from the lack of CELs (FIG. 4) and failure of current immunomodulatory treatments to inhibit disease progression. However, weak correlations (r<0.25) observed between CELs and soluble cell surface markers in this study support the notion that CELs only reflect inflammation that disrupts the blood brain barrier. While such perivascular inflammation is infrequent, T cell infiltration of brain tissue is consistently present in progressive MS (Hauser et al., *Ann Neurol* 19:578-587, 1986; Booss et al., *J Neurol Sci* 62:219-232, 1983).

In conclusion, the current study provides several biomarkers of intrathecal inflammation (IL-12p40, IL-8, sCD27, sCD14, sCD21, sCD14/monocyte, sCD27/T cell), which can enhance the development of treatments for neuroimmunological diseases, ultimately improving patient care.

Example 3: CSF Biomarkers and their Clinical Use

This example provides specific protein biomarkers and describes how they can be used to distinguish different patient populations (e.g. distinguish subjects with inflammatory neurological disease from subjects with non-inflammatory neurologic disease). The biomarkers were detected and/or measured by electrochemiluminescent assay (as described in Example 1) or using an aptamer-based array (SomaLogic, Boulder, Colo.).

In the tables below, the left column lists the NCBI gene name encoding the biomarker and shows alternative gene names in parentheses. The right column provides a summary of the biomarker's biological function. FIGS. 11-15 show CSF levels of the biomarkers listed in Tables 3A-3E.

TABLE 3A

Markers that differentiate inflammatory (OIND, MS) from non-inflammatory CNS conditions

| | |
|---|---|
| sCD27 (TNFRSF7) | Expressed mostly on activated memory T cells; binds CD70 and mediates apoptotic signal; its shedding may protect activated T cells from apoptosis. |
| SLAMF7 (SLAM family member F7, CRACC, CS1, CD319) | Expressed on NK cells, DCs, plasma B cells, T cells and microglia; generally inhibitory role when expressed on cell surface, so its shedding may potentiate immune activation. Targeted specifically by Elotuzumab. |

TABLE 3A-continued

Markers that differentiate inflammatory (OIND, MS) from non-inflammatory CNS conditions

| | |
|---|---|
| GZMA (granzyme A) | Cytolytic molecule, expressed in NK cells and cytotoxic T cells; increased CSF concentrations likely due to degranulation of these immune cells. |
| TNFRSF25 (DR3; death receptor 3) | Expressed on lymphocytes; stimulates NF-κB activity and regulates cell apoptosis; binds to TL1A (TNFSF15); linked to cartilage destruction in rheumatoid arthritis and fibrosis in Crohn's disease. |
| MMP9 (matrix metalloproteinase 9) | Enzyme released mostly by activated macrophages and neutrophils in many inflammatory conditions. |
| SLAMF3 (SLAM family member F3; Ly9, CD229) | Expressed on T, B, NK, DC and monocytes; linked to systemic lupus erythematosus and crucial for generation of auto-Ab against nuclear antigens; inhibitory receptor of IFN-γ-producing CD4+ T cells; its shedding may promote Th1 immunity. |

TABLE 3B

Markers that differentiate inflammatory (OIND, MS) from non-inflammatory CNS conditions, but also have enough discriminatory power to differentiate OIND from MS

| | |
|---|---|
| TNFRSF17 (BCMA, CD269) | Expressed mostly on differentiated B cells and plasma cells; highest intrathecal levels in MS, even when compared to OIND; mediates BAFF signaling on T cells. |
| TNFSF13B (BAFF; B cell activating factor) | Produced by inflammatory monocytes, DCs and neutrophils, but also astrocytes; provides activating signal to B cells. |
| TNFRSF17/TNFSF13B ratio (BCMA/BAFF ratio) | Can distinguish MS from OIND (and NINDS and HD) because the ratio is highly and selectively elevated in MS. |
| TNFSF15 (TL1A) | Binds to TNFRSF25 (DR3), where it stimulates NF-κB activity and apoptosis. |
| TNFRSF1B (TNF-R2) | Receptor for TNF-α, expressed on oligodendrocytes, astrocytes, endothelial cells and T cells; may protect neurons against apoptosis mediated by oxidative stress |
| CXCL10 (IP-10) | Secreted by monocytes, endothelial cells, fibroblasts and other cell types in response to IFN-γ; a chemoattractant for many immune cells. |

TABLE 3C

Markers that differentiate RRMS from progressive MS subtypes

| | |
|---|---|
| sCD27/Abs# of CSF T cells ratio | Biomarker of T cell infiltration of CNS tissue; significantly increased in both progressive MS subtypes in comparison to RRMS. |
| TNFSF14 (LIGHT; CD258) | Genetically linked to MS; a costimulatory factor for the activation of lymphoid cells - activated NF-κB; binds to HSV glycoprotein, which inhibits its signaling; signals via LTβ receptor to induce innate immune responses; protective in intestinal inflammation and important in recovery from EAE. |
| EPHB4 (ephrin-R B4) | Binds to ephrin-B2 and plays an essential role in vascular development (e.g. neovascularization in adults); also mediate neuro-developmental processes. |
| OLR1 (oxidized low-density lipoprotein receptor 1; LOX1) | The protein binds, internalizes and degrades oxidized low-density lipoprotein; has been linked to Alzheimer's disease, atherosclerosis and Fas-mediated apoptosis. |
| PPIB (peptidyl propyl isomerase B; Cyclophilin B) | Mainly located within the endoplasmic reticulum; participates in folding of collagen and mutations lead to osteogenesis imperfecta; expressed on all cells (can be used as qPCR house-keeping gene). |
| CDH15 (cadherin 15) | Associated with cognitive impairment, regulates neuronal migration, gray matter differentiation, neural circuit formation, spine morphology, synapse formation and synaptic remodeling; also expressed in brain endothelial cells. |
| PDE2A (PDE6C) | Photoreceptor-specific phosphodiesterase; unknown role in the CNS. |
| IGFBP7 (Insulin growth factor binding protein 7) | Regulation of availability of IGFs in tissue and modulating IGF binding to its receptors; tumor suppressor gene. Strong inverse correlation with disability and MRI score. |
| H2AFZ (H2A histone family member Z) | Replication-independent member of the histone H2A family that is distinct from other members of the family; important for oligodendrocyte progenitor cell proliferation; c-myc binds to its promoter. |
| APOD (Apolipoprotein D) | Mostly expressed by neurons and glial cells, implicated in neurodegeneration and aging. |
| DKKL1 (Soggy) | Vitamin D receptor regulated gene; expressed highly and uniquely in cortical neurons; interacts with the Wnt signaling pathway. |
| GFRA1 (GDNF family receptor alpha1) | Glial cell line-derived neurotrophic factor (GDNF) and neurturin (NTN) are two structurally related, potent neurotrophic factors that play key roles in the control of neuron survival and differentiation; both signal via GFRA1 |
| EDA2R (XEDAR, TNFRSF27) | Ectodysplasin A2 receptor; function in CNS or immune system not known; correlates with age and disability. |

TABLE 3C-continued

Markers that differentiate RRMS from progressive MS subtypes

| | |
|---|---|
| CCL25 (TECK) | Chemotactic for macrophages and DCs; binds CCR9 and its role is known only in thymus and small intestine, but not in CNS. Differentiates RRMS and SPMS from all other diagnostic classes. |

TABLE 3D

Markers that differentiate OIND from other categories

| | |
|---|---|
| sCD163 | Expressed selectively on macrophages, mostly M2; released upon differentiation and activation. |
| LAG3 (lymphocyte activation gene 3; CD223) | Close relationship to CD4; natural high affinity ligand for MHC-II; reduces differentiation of macrophages and DCs from monocytes; inhibitory co-receptor with role in autoimmunity (KO mice develop autoimmunity easier). |
| CD209 (DC-SIGN) | Dendritic cell specific marker; may be able to selectively distinguish patients with intrathecal activation of innate immunity |
| LYZ (lysozyme, muramidase) | Present in cytoplasmic granules of the neutrophils; functions by attacking peptidoglycans (found in the cell walls of bacteria); effector of innate immunity. |
| TNFRSF4 (OX40, CD134, TNR4) | A secondary costimulatory molecule, expressed after 24-72 hours post-activation; its ligand, OX40L, is also expressed only on activated antigen presenting cells; has a critical role in the maintenance of an immune response and development of immune memory by enhancing T cell survival. |
| CCL7 (MCP-3) | Specifically attracts monocytes, and regulates macrophage function; produced by macrophages. |

*Most of the biomarkers listed in Table 3D are markers of innate immunity and therefore are associated with engagement of innate immune responses

TABLE 3E

Markers that differentiate healthy donors from all neurological diseases

| | |
|---|---|
| LGMN (Legumain) | A cysteine protease that hydrolyzes asparaginyl bonds; involved in the processing of bacterial peptides and endogenous proteins for MHC class II presentation in the lysosomal/endosomal systems. |
| GPNMB (glycoprotein nonmetastatic melanoma protein B) | Expressed in dendritic cells, microglia, motor neurons and astrocytes; neuroprotective in amyotrophic lateral sclerosis; upregulated after ischemic injury; promotes angiogenesis and tissue repair. Good correlation with MRI score to some extent disability. |
| SPOCK2 (sparc/osteonectin, cwcv and kazal-like domains proteoglycan 2, testican 2) | $Ca^{2+}$ binding extracellular matrix protein expressed in brain; binds glycosaminoglycans to form part of the extracellular matrix. |
| SPOCK2/GPNMB ratio | Highest ratio in HDs and significantly decreased in all neurological disorders. |
| OLR1 (oxidized low density lipoprotein (lectin-like) receptor 1; LOX1) | Expressed on monocytes and macrophages; binds, internalizes and degrades oxidized low-density lipoprotein; involved in regulation of Fas-induced apoptosis; correlates with disability and MRI score. |
| IGFBP7 (insulin growth factor binding protein 7) | Regulation of availability of IGFs in tissue and modulating IGF binding to its receptors; tumor suppressor gene. Strong inverse correlation with disability and MRI score. |
| MFRP (membrane frizzled-related protein) | Gene defects cause retinitis pigmentosa; important for survival of photoreceptors; role in CNS unknown. |
| CHIT1 (chitinase 1, chitotriosidase 1) | Secreted by activated human macrophages; the expression of chitotriosidase occurs only at a late stage of differentiation of monocytes to activated macrophages; may play a role in the degradation of chitin-containing pathogens. |

TABLE 3F

Process-specific biomarkers that can be used instead of brain biopsy

| | |
|---|---|
| sCD27/Abs# of CSF T cells ratio | Biomarkers of T cell infiltration of CNS tissue. |
| sCD14/Abs# of CSF monocyte ratio | Biomarker of microglial/macrophage activation in the CNS tissue. |
| TNFRSF17/Abs# of CSF B cell ratio | Biomarker of B cell and plasma cell infiltration of CNS tissue. |
| CD209/Abs# of CSF DC ratio | Biomarker of dendritic cell infiltration of CNS tissue. |
| RTN4 (Reticulin 4; NOGO) | A potent neurite outgrowth inhibitor, which may block the regeneration of the central nervous system, including remyelination; high CSF concentrations in majority of MS. |

TABLE 3G

| Biomarkers negatively correlated with disability or CNS tissue destruction | |
|---|---|
| TIMP2 | Identifies patients with resistance to CNS tissue injury; therapies that increase this biomarker could provide neuro-protection. |
| APCS | Identifies patients with resistance to CNS tissue injury; therapies that increase this biomarker could provide neuro-protection. |
| IGFBP7 | Identifies patients with resistance to CNS tissue injury; therapies that increase this biomarker could provide neuro-protection. |
| BCL2A1 | Identifies patients with resistance to CNS tissue injury; therapies that increase this biomarker could provide neuro-protection. |
| LGMN | Identifies patients with resistance to CNS tissue injury; therapies that increase this biomarker could provide neuro-protection. |

TABLE 3H

| Biomarkers positively correlated with disability or CNS tissue destruction | |
|---|---|
| ROR1 | All of these biomarkers identify patients with neurodegeneration or aging; therapies that decrease these markers in patients could be used to provide neuro-protection. |
| EFNA4 | |
| IL-1RAP | |
| HGF | |
| TNFSF4 | |
| EDA2R | |
| CD109 | |
| TNFSF8 | |
| OLR1 | |
| CKB | |
| GPI | |
| PLXNC1 | |
| PDIA3 | |
| ITGAV/ITGB5 | |
| CDNF | |
| GPC5 | |
| HAVCR2 | |
| CPE | |
| IL-17RC | |
| CXCL16 | |
| TNFRSF17 | |

TABLE 3H-continued

| Biomarkers positively correlated with disability or CNS tissue destruction | |
|---|---|
| CNTN1 | |
| KLRK1 | |
| FCGR2A | |
| FCGR2B | |
| FCGR3B | |
| AGT | |
| CTSH | |
| IL-11RA | |
| ANP32B | |
| CHST6 | |
| IL-5RA | |
| FUT5 | |
| CGA/CGB | |
| CDNF | |
| CD300C | |
| GPNMB | |
| TNFRSF12A | |
| HAVCR2 | |
| OMD | |
| SLAMF7 | |
| IL-1RAP | These biomarkers identify patients with neurodegeneration or aging, and are makers of microglial activation and inflammasome; therapies that decrease these markers in patients could be used to provide neuro-protection. |
| IL-18BP | |
| IL-18R1 | |

Example 4: Additional Biomarkers Identified by Aptamer-Based Array

The biomarkers listed in the table below were identified using an aptamer-based array (SomaLogic, Boulder, Colo.). These biomarkers can be used to identify one or more different patient populations (e.g., to identify patients with intrathecal inflammation, distinguish MS patients from patients with other types of inflammatory neurological diseases, distinguish progressive MS patients from patients with RRMS, identify subjects with non-MS inflammatory neurological diseases, differentiate healthy subjects from patients with any type of neurological disease and/or identify subjects with CNS tissue destruction).

TABLE 4

Additional Biomarkers

| Entrez Gene Symbol | SOMA ID | Full Name | ANOVA corrected p-value |
|---|---|---|---|
| SLAMF7 | SL016928 | SLAM family member 7 | 3.93E−08 |
| IGHG1 IGHG2 IGHG3 IGHG4 IGK IGL | SL000467 | Immunoglobulin G | 3.93E−08 |
| CD48 | SL010450 | CD48 antigen | 4.03E−08 |
| TNFRSF17 | SL004672 | Tumor necrosis factor receptor superfamily member 17 | 1.03E−07 |
| MMP9 | SL000527 | Matrix metalloproteinase-9 | 1.23E−07 |
| SH2D1A | SL014468 | SH2 domain-containing protein 1A | 1.55E−07 |
| CXCL10 | SL003183 | C—X—C motif chemokine 10 | 4.18E−07 |
| FCN1 | SL010462 | Ficolin-1 | 8.08E−07 |
| PPIB | SL007869 | Peptidyl-prolyl cis-trans isomerase B | 8.08E−07 |
| PDE2A | SL005730 | cGMP-dependent 3',5'-cyclic phosphodiesterase | 1.1E−06 |
| SFTPD | SL004484 | Pulmonary surfactant-associated protein D | 1.33E−06 |
| CCL7 | SL000516 | C-C motif chemokine 7 | 1.54E−06 |
| APOD | SL005361 | Apolipoprotein D | 2.17E−06 |
| DYRK3 | SL013570 | Dual specificity tyrosine-phosphorylation-regulated kinase 3 | 2.17E−06 |
| VCAM1 | SL001720 | Vascular cell adhesion protein 1 | 3.71E−06 |
| LTA | SL000597 | Lymphotoxin-alpha | 4.78E−06 |
| TNFSF15 | SL004686 | Tumor necrosis factor ligand superfamily member 15 | 5.14E−06 |

TABLE 4-continued

Additional Biomarkers

| Entrez Gene Symbol | SOMA ID | Full Name | ANOVA corrected p-value |
|---|---|---|---|
| TNFSF13B | SL004327 | Tumor necrosis factor ligand superfamily member 13B | 5.14E-06 |
| BSG | SL009341 | Basigin | 5.43E-06 |
| CDH15 | SL007295 | Cadherin-15 | 5.43E-06 |
| PRSS27 | SL011069 | Serine protease 27 | 5.85E-06 |
| CXCL1 | SL003173 | Growth-regulated alpha protein | 5.85E-06 |
| CXCL11 | SL003326 | C—X—C motif chemokine 11 | 6.13E-06 |
| H2AFZ | SL002093 | Histone H2A.z | 6.23E-06 |
| DKKL1 | SL010381 | Dickkopf-like protein 1 | 6.97E-06 |
| CD163 | SL005764 | Scavenger receptor cysteine-rich type 1 protein M130 | 7.27E-06 |
| TNFRSF25 | SL004791 | Tumor necrosis factor receptor superfamily member 25 | 7.29E-06 |
| LAG3 | SL005195 | Lymphocyte activation gene 3 protein | 8.77E-06 |
| BCAR3 | SL014470 | Breast cancer anti-estrogen resistance protein 3 | 1.26E-05 |
| CXCL13 | SL003167 | C—X—C motif chemokine 13 | 1.42E-05 |
| EPHB4 | SL004845 | Ephrin type-B receptor 4 | 1.46E-05 |
| LY9 | SL007674 | T-lymphocyte surface antigen Ly-9 | 1.46E-05 |
| STK17B | SL016566 | Serine/threonine-protein kinase 17B | 1.46E-05 |
| CD209 | SL005157 | CD209 antigen | 1.46E-05 |
| CCL23 | SL003302 | C-C motif chemokine 23 | 1.85E-05 |
| CSF3 | SL001729 | Granulocyte colony-stimulating factor | 2.12E-05 |
| TNFRSF1B | SL001800 | Tumor necrosis factor receptor superfamily member 1B | 2.98E-05 |
| PDE3A | SL016553 | cGMP-inhibited 3',5'-cyclic phosphodiesterase A | 2.98E-05 |
| LYZ | SL000510 | Lysozyme C | 3.22E-05 |
| PIGR | SL005797 | Polymeric immunoglobulin receptor | 3.34E-05 |
| CCL23 | SL003301 | Ck-beta-8-1 | 3.34E-05 |
| KLK7 | SL000064 | Kallikrein-7 | 3.64E-05 |
| LTA LTB | SL000507 | Lymphotoxin alpha1:beta2 | 4.14E-05 |
| ABL2 | SL010488 | Abelson tyrosine-protein kinase 2 | 4.23E-05 |
| CCL25 | SL003197 | C-C motif chemokine 25 | 4.23E-05 |
| HIST1H1C | SL005256 | Histone H1.2 | 4.7E-05 |
| GZMA | SL004298 | Granzyme A | 5.21E-05 |
| CD84 | SL008588 | SLAM family member 5 | 6.02E-05 |
| OLR1 | SL007327 | Oxidized low-density lipoprotein receptor 1 | 6.02E-05 |
| SLC25A18 | SL016563 | Mitochondrial glutamate carrier 2 | 8.24E-05 |
| IL5 | SL000481 | Interleukin-5 | 8.24E-05 |
| SLAMF6 | SL014228 | SLAM family member 6 | 8.24E-05 |
| IL16 | SL000474 | Interleukin-16 | 8.41E-05 |
| CDH3 | SL004183 | Cadherin-3 | 8.62E-05 |
| EDA2R | SL005233 | Tumor necrosis factor receptor superfamily member 27 | 9.2E-05 |
| MAP3K7 TAB1 | SL016567 | Mitogen-activated protein kinase kinase kinase 7:TGF-beta-activated kinase 1 and MAP3K7-binding protein 1 fusion | 9.75E-05 |
| IGFBP7 | SL005087 | Insulin-like growth factor-binding protein 7 | 9.95E-05 |
| SPOCK2 | SL010471 | Testican-2 | 9.95E-05 |
| CTSV | SL006910 | Cathepsin L2 | 0.0001 |
| TNFSF14 | SL004648 | Tumor necrosis factor ligand superfamily member 14 | 0.000126 |
| IL13RA1 | SL004149 | Interleukin-13 receptor subunit alpha-1 | 0.000126 |
| C2 | SL002525 | Complement C2 | 0.000129 |
| PTPN6 | SL004940 | Tyrosine-protein phosphatase non-receptor type 6 | 0.000145 |
| IL6 | SL000087 | Interleukin-6 | 0.000151 |
| PLA2G7 | SL003440 | Platelet-activating factor acetylhydrolase | 0.000151 |
| CCL22 | SL003187 | C-C motif chemokine 22 | 0.000158 |
| TNFRSF6B | SL003739 | Tumor necrosis factor receptor superfamily member 6B | 0.000178 |
| C3 | SL000313 | C3a anaphylatoxin | 0.000193 |
| FCGR3B | SL008609 | Low affinity immunoglobulin gamma Fc region receptor III-B | 0.000193 |
| CD86 | SL004131 | T-lymphocyte activation antigen CD86 | 0.000202 |
| CSK | SL004781 | Tyrosine-protein kinase CSK | 0.000204 |
| CXCL6 | SL003172 | C—X—C motif chemokine 6 | 0.000204 |
| GRN | SL007173 | Granulins | 0.000208 |

TABLE 4-continued

Additional Biomarkers

| Entrez Gene Symbol | SOMA ID | Full Name | ANOVA corrected p-value |
|---|---|---|---|
| TNFRSF11A | SL003690 | Tumor necrosis factor receptor superfamily member 11A | 0.000232 |
| SPARCL1 | SL005488 | SPARC-like protein 1 | 0.000253 |
| DSG2 | SL004857 | Desmoglein-2 | 0.000265 |
| GPNMB | SL007429 | Transmembrane glycoprotein NMB | 0.000274 |
| ICAM1 | SL002922 | Intercellular adhesion molecule 1 | 0.000429 |
| AMHR2 | SL007464 | Anti-Muellerian hormone type-2 receptor | 0.000429 |
| HAVCR2 | SL007547 | Hepatitis A virus cellular receptor 2 | 0.000429 |
| CXCL3 CXCL2 | SL017610 | Gro-beta/gamma | 0.000429 |
| EFNA4 | SL004140 | Ephrin-A4 | 0.000454 |
| TYK2 | SL007181 | Non-receptor tyrosine-protein kinase TYK2 | 0.000476 |
| NUDCD3 | SL011768 | NudC domain-containing protein 3 | 0.000476 |
| CMPK1 | SL007871 | UMP-CMP kinase | 0.000478 |
| C7 | SL000323 | Complement component C7 | 0.000478 |
| HNRNPAB | SL009791 | Heterogeneous nuclear ribonucleoprotein A/B | 0.000481 |
| TNFAIP6 | SL004782 | Tumor necrosis factor-inducible gene 6 protein | 0.000481 |
| MRC1 | SL004579 | Macrophage mannose receptor 1 | 0.000481 |
| IL18BP | SL002508 | Interleukin-18-binding protein | 0.000495 |
| NCR1 | SL005207 | Natural cytotoxicity triggering receptor 1 | 0.000513 |
| VWF | SL000017 | von Willebrand factor | 0.000542 |
| PDCD1LG2 | SL004862 | Programmed cell death 1 ligand 2 | 0.000552 |
| LTA LTB | SL000508 | Lymphotoxin alpha2:beta1 | 0.000558 |
| GFAP | SL004271 | Glial fibrillary acidic protein | 0.000589 |
| HNRNPA2B1 | SL004891 | Heterogeneous nuclear ribonucleoproteins A2/B1 | 0.000609 |
| CXCL8 | SL000039 | Interleukin-8 | 0.000676 |
| SHC1 | SL014469 | SHC-transforming protein 1 | 0.000705 |
| GP6 | SL008759 | Platelet glycoprotein VI | 0.000754 |
| RAC1 | SL004009 | Ras-related C3 botulinum toxin substrate 1 | 0.000781 |
| TEC | SL010518 | Tyrosine-protein kinase Tec | 0.000781 |
| ICOSLG | SL004853 | ICOS ligand | 0.000781 |
| SELL | SL002823 | L-Selectin | 0.000909 |
| HAMP | SL004536 | Hepcidin | 0.000909 |
| TNFRSF1A | SL001992 | Tumor necrosis factor receptor superfamily member 1A | 0.000914 |
| PRTN3 | SL004008 | Myeloblastin | 0.000923 |
| CD70 | SL007195 | CD70 antigen | 0.001097 |
| EGFR | SL002644 | Epidermal growth factor receptor | 0.001111 |
| AK1 | SL004296 | Adenylate kinase isoenzyme 1 | 0.001182 |
| UFC1 | SL010529 | Ubiquitin-fold modifier-conjugating enzyme 1 | 0.001189 |
| HSD17B10 | SL004795 | 3-hydroxyacyl-CoA dehydrogenase type-2 | 0.001304 |
| SIGLEC7 | SL005218 | Sialic acid-binding Ig-like lectin 7 | 0.001304 |
| PAPPA | SL002755 | Pappalysin-1 | 0.001461 |
| UBE2I | SL004306 | SUMO-conjugating enzyme UBC9 | 0.001487 |
| CLIC1 | SL004915 | Chloride intracellular channel protein 1 | 0.001586 |
| PRSS2 | SL010388 | Trypsin-2 | 0.001681 |
| LILRB2 | SL005191 | Leukocyte immunoglobulin-like receptor subfamily B member 2 | 0.001681 |
| METAP2 | SL007261 | Methionine aminopeptidase 2 | 0.001695 |
| AIP | SL011629 | AH receptor-interacting protein | 0.001857 |
| HMGB1 | SL003280 | High mobility group protein B1 | 0.001952 |
| DCN | SL004081 | Decorin | 0.002145 |
| AKR1A1 | SL008039 | Alcohol dehydrogenase [NADP(+)] | 0.002156 |
| C3 | SL003220 | C3a anaphylatoxin des Arginine | 0.002177 |
| IL1RAP | SL004588 | Interleukin-1 Receptor accessory protein | 0.002182 |
| CLEC7A | SL007640 | C-type lectin domain family 7 member A | 0.002198 |
| CD300C | SL014270 | CMRF35-like molecule 6 | 0.002198 |
| LCN2 | SL000695 | Neutrophil gelatinase-associated lipocalin | 0.002451 |
| CDH5 | SL002081 | Cadherin-5 | 0.002588 |
| SEMA3E | SL010470 | Semaphorin-3E | 0.002636 |
| TNFRSF9 | SL004126 | Tumor necrosis factor receptor superfamily member 9 | 0.002636 |
| CHIT1 | SL006029 | Chitotriosidase-1 | 0.002728 |
| C3 | SL000312 | Complement C3 | 0.002728 |

TABLE 4-continued

Additional Biomarkers

| Entrez Gene Symbol | SOMA ID | Full Name | ANOVA corrected p-value |
|---|---|---|---|
| PSME1 | SL008176 | Proteasome activator complex subunit 1 | 0.00297 |
| SERPINE2 | SL004457 | Glia-derived nexin | 0.003008 |
| C3 | SL000456 | Complement C3b, inactivated | 0.003008 |
| IL22RA2 | SL005183 | Interleukin-22 receptor subunit alpha-2 | 0.003008 |
| CCL15 | SL003190 | C-C motif chemokine 15 | 0.003046 |
| PAFAH1B2 | SL004760 | Platelet-activating factor acetylhydrolase IB subunit beta | 0.003144 |
| SERPING1 | SL000308 | Plasma protease C1 inhibitor | 0.003645 |
| PF4 | SL003041 | Platelet factor 4 | 0.00368 |
| CAST | SL000338 | Calpastatin | 0.003915 |
| NCR3 | SL005205 | Natural cytotoxicity triggering receptor 3 | 0.003995 |
| RTN4 | SL008309 | Reticulon-4 | 0.004353 |
| PRKCB | SL000553 | Protein kinase C beta type (splice variant beta-II) | 0.004489 |
| CD5L | SL006108 | CD5 antigen-like | 0.004537 |
| CCL19 | SL003189 | C-C motif chemokine 19 | 0.004537 |
| TNFSF8 | SL004635 | Tumor necrosis factor ligand superfamily member 8 | 0.005277 |
| PLAUR | SL002506 | Urokinase plasminogen activator surface receptor | 0.005413 |
| BGN | SL007804 | Biglycan | 0.005973 |
| CLEC11A | SL004362 | Stem Cell Growth Factor-beta | 0.006166 |
| CCL18 | SL003323 | C-C motif chemokine 18 | 0.006511 |
| INHBA | SL001938 | Inhibin beta A chain | 0.006661 |
| PRSS1 | SL000603 | Trypsin-1 | 0.007318 |
| C4A C4B | SL000318 | Complement C4b | 0.007328 |
| SFRP1 | SL003770 | Secreted frizzled-related protein 1 | 0.007369 |
| CCL11 | SL000406 | Eotaxin | 0.007369 |
| C1QA C1QB C1QC | SL000309 | Complement C1q subcomponent | 0.007369 |
| NRP1 | SL006397 | Neuropilin-1 | 0.007369 |
| GSN | SL005572 | Gelsolin | 0.007369 |
| CDNF | SL012538 | Cerebral dopamine neurotrophic factor | 0.007411 |
| CKM | SL000383 | Creatine kinase M-type | 0.007433 |
| LILRB1 | SL005190 | Leukocyte immunoglobulin-like receptor subfamily B member 1 | 0.008153 |
| TNNI2 | SL004594 | Troponin I, fast skeletal muscle | 0.008355 |
| MPO | SL001796 | Myeloperoxidase | 0.008572 |
| EIF4G2 | SL011211 | Eukaryotic translation initiation factor 4 gamma 2 | 0.009461 |
| SERPINE1 | SL000006 | Plasminogen activator inhibitor 1 | 0.009471 |
| PPBP | SL004708 | Connective tissue-activating peptide III | 0.009878 |
| SELP | SL000560 | P-Selectin | 0.010258 |
| CGA CGB | SL001766 | Human Chorionic Gonadotropin | 0.010571 |
| GPI | SL000539 | Glucose-6-phosphate isomerase | 0.011761 |
| IGHM IGJ IGK IGL | SL000468 | Immunoglobulin M | 0.012107 |
| LYVE1 | SL008904 | Lymphatic vessel endothelial hyaluronic acid receptor 1 | 0.014497 |
| CD274 | SL004852 | Programmed cell death 1 ligand 1 | 0.015602 |
| LGMN | SL008909 | Legumain | 0.016072 |
| AGRP | SL006924 | Agouti-related protein | 0.017166 |
| PROC | SL003974 | Activated Protein C | 0.017861 |
| YWHAB, YWHAE, YWHAG, YWHAH, YWHAQ, YWHAZ, SFN | SL017611 | 14-3-3 protein family | 0.018045 |
| CSF1R | SL004153 | Macrophage colony-stimulating factor 1 receptor | 0.018156 |
| IL27RA | SL005223 | Interleukin-27 receptor subunit alpha | 0.018156 |
| ADIPOQ | SL004258 | Adiponectin | 0.01887 |
| CFL1 | SL004920 | Cofilin-1 | 0.019866 |
| IL17B | SL004350 | Interleukin-17B | 0.019889 |
| ANGPT2 | SL001996 | Angiopoietin-2 | 0.020729 |
| CAPG | SL008099 | Macrophage-capping protein | 0.020749 |
| IL5RA | SL005188 | Interleukin-5 receptor subunit alpha | 0.021289 |
| ANP32B | SL011769 | Acidic leucine-rich nuclear phosphoprotein 32 family member B | 0.023649 |
| C5 C6 | SL000321 | Complement C5b-C6 complex | 0.023702 |
| KLK3 SERPINA3 | SL000091 | PSA:alpha-1-antichymotrypsin complex | 0.025653 |
| MBL2 | SL004516 | Mannose-binding protein C | 0.031047 |
| GNLY | SL000678 | Granulysin | 0.035102 |
| C5 | SL000319 | Complement C5 | 0.036266 |
| S100A9 | SL004477 | Protein S100-A9 | 0.039393 |

TABLE 4-continued

Additional Biomarkers

| Entrez Gene Symbol | SOMA ID | Full Name | ANOVA corrected p-value |
|---|---|---|---|
| HSP90AA1 HSP90AB1 | SL017612 | Heat shock protein HSP 90-alpha/beta | 0.04 |

Example 5: Diagnosis of MS and its Progressive Stage Using Slow Off-Rate Modified DNA-Aptamers (SOMAmers)

This example describes the identification of biomarkers that distinguish MS from non-MS subjects and biomarkers that distinguish patients with progress MS from patients with RRMS using aptamer-based arrays.

Methods

Subjects

Demographic data for all subjects is shown in FIG. 20. The diagnostic workup included neurological exam, MRI of the brain and laboratory tests (blood, CSF) as described (Komori et al., *Ann Neurol* 78(1):3-20, 2015). The diagnoses of relapsing-remitting MS (RRMS), primary progressive (PPMS) and secondary progressive MS (SPMS) were based on published criteria (Tumani et al., *Expert Rev Mol Diagn* 8(4):479-494, 2008). The remaining subjects were classified as either other inflammatory neurological disorders (OIND) or non-inflammatory neurological disorders (NIND) based on the evidence of intrathecal inflammation. A group of healthy donors (HD) was also included. The vast majority of subjects were not treated by disease-modifying therapies at the time of CSF collection.

CSF Collection and Processing

CSF was collected on ice and processed according to a written standard operating procedure. Research CSF aliquots were assigned prospective alpha-numeric codes, and centrifuged (335 g for 10 minutes at 4° C.) within 15 minutes of collection. The CSF supernatant was aliquoted and stored in polypropylene tubes at −80° C. until use.

SOMASCAN™ Assay

SOMASCAN™ technology (SomaLogic, Inc., Boulder, Colo.) is a multiplexed proteomic analysis of 1128 analytes in 75 µl volume of biological matrices. Protein-capture SOMAmers, single-stranded DNA molecules synthesized from chemically modified nucleotides, play a dual role of protein affinity-binding reagents and a DNA sequence recognized by complementary DNA probes. This enables transformation of individual protein concentration into a DNA concentration quantified by hybridization, offering exceptional dynamic range (~110 fM to ~7.2 nM) (Gold et al., *N Biotechnol* 29(5):543-549, 2012; Kraemer et al., *PLoS One* 6(10):e26332, 2011; Gold et al., *PLoS One* 5(12):e15004, 2010). The raw assay data are normalized and calibrated: Hybridization normalization uses a set of twelve hybridization controls for each array. Median signal normalization removes sample or assay biases due to differences in protein concentration, pipetting variation or assay timing within a single plate run. Finally, a common pooled calibrator corrects for plate-to-plate variation. SOMAmers are selected against proteins in their native folded conformations.

Biomarker Validation Assays

Electrochemiluminescent assays quantified the concentrations of selected biomarkers using the Meso Scale Discovery (MSD; Meso Scale Diagnostics, Rockville, Md.) as described (Komori et al., *Ann Neurol* 78(1):3-20, 2015). The concentration of interleukin (IL)-6 and IL-8 was measured by MSD V-plex using the manufacturer's protocol. The assays for IL-6R, soluble CD23 (sCD23), sCD27, sCD163, B-cell activating factor (BAFF), B-cell maturation antigen (BCMA), brain-derived neurotrophic factor (BDNF), DJ-1, hepatocyte growth factor (HGF), neural cell adhesion molecule (NCAM)1, Sirtuin2, and C—X—C motif chemokine 13 (CXCL13) were developed in the NDU laboratory. The concentration of cytochrome C was measured by conventional ELISA (Enzo Life Sciences, Inc., Farmingdale, N.Y.). All samples excluding IL-8 were run in duplicate. Each assay contained a minimum of two additional reference samples per plate to evaluate intra- and inter-assay reliability. The details of the reagents, manufacturer, detection limits and intra-assay coefficients of variance are depicted in FIG. 21.

Assessment of Cellular Origin of Tested Biomarkers from the Subset of Human Immune Cells Fresh peripheral blood mononuclear cells (PBMC) of two MS patients and two HD were obtained from FICOLL™ gradient-treated aphereses. Monocytes, B cells, T cell subsets, natural killer (NK) cells, innate lymphoid cells (ILCs), and myeloid dendritic cells (DCs) were FACS sorted. Each purified cell subtype was cultured at a concentration of $1 \times 10^6$ cells/ml in serum-free X-VIVO 15 medium (Lonza, Walkersville, Md.) with or without 10 ag/mL phorbol myristate acetate (PMA) and 1 aM ionomycin. Supernatants were collected after 48 hours and frozen until biomarker measurements.

Statistical Testing and Power Analysis

A power analysis was performed based on the discovery cohort (N=85). 289 of the 1128 variables had Benjamini-Hochberg False-Discovery Rate adjusted p-values<0.05 from overall F-tests and had one of the 15 Tukey HSD pair-wise group comparisons with a p-value<0.05 and a fold-change>1.3. The fold-change requirement was set to focus later analyses on markers that expressed large differences in means, not just large differences relative to variability in the groups. The markers that met this requirement were identified for similar screening in the independent validation cohort (N=225) and were considered validated if the same conditions were met and the direction of the pairwise differences matched in the pilot and validation analyses.

Required sample sizes per group for the validation cohort were calculated using the pwr package in R to provide 90% power for the overall F-test for comparing the log 2-scale responses in the six diagnostic groups with effect sizes based on the discovery data results along with using the conservative Bonferroni corrected 5% significance-level tests.

Signal-to-Noise Ratio (SNR)

Differences in replicated measurements on the same sample for six subjects quantified the technical variability. Similarly, differences in measurements taken on longitudinal samples from four HD quantified the biological variability.

Since the distributions of the biomarkers are generally skewed with outlying observations, the inter-quartile range (IQR) of these differences was used. The inter-quartile range across all diagnoses in the validation cohort was used to measure the intra-individual variability in biomarkers for all subjects. The biological signal-to-noise ratio (B-SNR) was defined to be the intra-individual variability divided by biological variability (measured as IRQ of absolute differences between longitudinal samples of four HD). Likewise, technical signal-to-noise ratio (T-SNR) was defined to be the intra-individual variability divided by technical variability (measured as IRQ of absolute differences between repeated measures of seven subjects). Biomarkers with both B-SNR and T-SNR of at least 3 were considered to have high signal-to-noise.

Area Under the Receiver Operating Characteristics (ROC) Curve (AUC)

The Area under the ROC curve (AUC; R statistical software using the roc function in the pROC package (Robin et al., *BMC Bioinformatics* 12:77, 2011) quantified the ability of each biomarker (or a ratio of two biomarkers) to differentiate two diagnostic groups. Higher AUC values imply a larger potential for separating diagnostic groups. The AUCs were calculated for all 1128 SOMAmers and for 105,111 pairs of ratios formed from the SOMAmers with SNR>3 in the larger (N=225) cohort. A cutoff of 0.9 was used to identify ratios of biomarkers differentiating MS from non-MS subjects. Similarly, a cutoff of 0.8 was used in differentiating progressive from RRMS. These selected biomarker ratios were then validated in the independent smaller (N=85) cohort by calculating corresponding AUCs and assessing their statistical significance by construction of permutation based p-values (using 10,000 permutations of original data) for testing H_0: AUC=0.5 against the upper one-sided alternative. These were corrected for multiple comparisons using the Benjamini and Hochberg False Discovery Rate correction.

Random Forest

Random Forests (Hastie et al., "The Elements of Statistical Learning: Data Mining, Inference, and Prediction," Springer, 2009) were used to create an ensemble classifier to improve AUC performance ("randomForest" R package; Liaw and Wiener, *R News* Vol. 2/3, pages 18-22, December 2002). They are built by sequentially estimating classification trees using bootstrapped samples (1,000 were chosen, corresponding to 1,000 classification trees within the forest) from the data using a random subset of predictors for each tree node. Predictions for new observations are based on a majority vote of the total number of trees (for classification). Taking this "average" of the constructed trees can reduce the variance from single trees to improve the classification performance. Random Forests were used to build two classifiers: differentiating MS from non-MS (HD, OIND, NIND) and differentiating progressive MS (PPMS, SPMS) from RRMS. These classifiers were trained in the larger (N=225) cohort using and the predictive ability of these classifiers was assessed on the independent smaller (N=85) cohort. Variable importance measures (average decrease in accuracy from permuting each covariate across all trees) and estimated marginal effects (Breiman, *Machine Learning* 45(1): 5-32, 2001; Friedman, *AnnStat* 29: 1189-1232, 2001) were used to measure and understand the contribution of individual biomarkers (and ratios) to explaining the variation in the diagnostic groups.

Results

Technical Parameters of SOMASCAN™ Assay

To determine SOMAscan's suitability for clinical research, six blinded technical replicates (identical CSF aliquots analyzed at different time points), four biological replicates (longitudinal samples from four HD with CSF collected >1 year from the first analyzed sample) and longitudinal CSF samples from five OIND patients collected before and after disease-modifying therapy (DMT) (e.g., high dose solumedrol) were analyzed.

The average variance in the technical replicates was 6.61%. The biological replicates had also excellent reproducibility, with measured variance of 6.44%. Most biological variability originated from different levels of blood contamination of the CSF, as almost all biomarkers with high biological variance were prominent serum proteins.

In contrast, the measured variance in pre- and post-treatment longitudinal samples exceeded highest technical and biological variance measured, indicating that SOMASCAN™ has high signal to noise ratio (SNR). In fact, in two OIND patients (non-immunocompromised subjects with cryptococcal meningitis) who had the most dissimilar biomarker profile in comparison to HD, the overall biological variance in pre- and post-therapy sample reached 40%. It was concluded that SOMASCAN™ can sensitively detect drug-induced changes in biomarker profiles in small cohorts of patients.

Validation of Selected SOMAmers by Alternative Methodology

Selected SOMAmers were validated by antibody-based immunoassays (ELISA). Out of 15 selected biomarkers, high (r>0.75) or medium (0.75≥r>0.5) correlations were observed between SOMASCAN™ and ELISA for 9/15 (60%). One additional biomarker had low (0.5≥r>0.25) correlation and another had statistically-significant correlation that was considered biologically negligible (r≤0.25). Four did not correlate at all.

It was concluded that 2/3 of tested SOMAmers (67%) measure analogous antigens to ELISA assays. Among non-correlating biomarkers were sCD27 and IL-8, for which significant, biologically-relevant differences between analogous diagnostic cohorts had been previously demonstrated using identical ELISA assays (Komori et al., *Ann Neurol* 78(1):3-20, 2015).

SOMASCAN™ Results in Discovery Cohort and Resultant Power Analysis

Next, blinded analysis of the discovery cohort (N=85), consisting of 15 untreated subjects per each patient category (i.e. RRMS, PPMS, SPMS, NIND and OIND) and 10 HD was performed. After unblinding, 289 biomarkers that differentiated at least 2 diagnostic categories after statistical adjustment for multiple comparisons were identified (FIG. 16). Based on these results, power analysis was performed and it was concluded that 9 to 36 subjects per group were required to have sufficient power to detect some differences in the 289 biomarkers subjected to follow-up testing. Resources provided for an attempted recruitment of 40 subjects per group (with exception of HD with only 25 subjects), which exceeded the minimum required sample size for all of the markers that met the initial screening criteria in the pilot data.

Confirmatory Cohort

Independent confirmatory cohort consisted of blinded analysis of 225 CSF samples from 40 subjects per each patient category and 25 HD. Seven blinded technical replicas (identical CSF samples that were analyzed in the discovery cohort were added to the confirmatory cohort) demonstrated significantly higher technical variance (10.50%; p<0.0001, Mann-Whitney test on ranks) in comparison to 6.61% measured originally. This led to the discovery that the two studies were inadvertently run on two different instruments. SomaLogic personnel normalized data between the two instruments based on the common calibrators, but with significantly higher technical noise.

Despite the increase in technical noise, 215 out of 289 biomarkers (74%) identified in the pilot cohort were validated. The validation rate was excellent for all diagnostic categories, with the exception of RRMS (FIG. 16). To increase the chance of detecting significant differences in the small discovery cohort, RRMS patients with high disease severity were selected. In contrast, validation cohort is representative of broad RRMS population. It is believed that this explains the lower number of validated biomarkers for RRMS in the latter cohort and the broad overlap in biomarker signatures between RRMS and progressive MS subtypes. Only one biomarker (MMP9) was validated as differentially expressed between RRMS and PPMS, while no biomarkers could reproducibly differentiate RRMS and SPMS or the two progressive MS cohorts (FIG. 16).

Overall, 27 unique biomarkers distinguished any of MS subgroups from each other or from NINDS and HD cohorts (Table 5). The majority of these were biomarkers related to immune responses, classified by Ingenuity pathway analysis (Qiagen) into six functional processes or disease states upregulated in MS: inflammatory response, cell death, quantity of immunoglobulins, cell movement of leukocytes and activation of cells. Two additional processes/disease states were inhibited in MS: viral infections and angiogenesis. Most of the relevant biomarkers were secreted or transmembrane proteins released as alternatively spliced variants or shed by proteolytic cleavage.

Deconvolution of Biomarkers' Cell of Origin

To better understand potential functions of identified biomarkers, their cell of origin was annotated using two parallel approaches. First, SOMAmers were measured in the supernatants of freshly sorted resting or PMA/ionomycin activated human dendritic cells, monocytes, ILCs, T cells, B cells, and NK cells. Second, publicly available databases were searched for information about expression profiles of CNS cells. A study published by Zhang et al. (*J Neurosci* 34(36):11929-11947, 2014) presents RNA-seq analysis of gene expression profiles of murine neurons, astrocytes, microglia, endothelial cells, and oligodendrocytes. "Fold enrichment" (relative expression) was calculated as fragments per kilobase of transcript sequence per million mapped fragments (FPKM) of a given cell type divided by the average FPKM of all other cell types.

Cell-specificity data for biomarkers identified as meaningful in the SOMASCAN™ are presented in Table 5. Only a minority of the MS-relevant proteins were secreted in purified immune cell cultures, with DCs and stimulated NK cells, ILCs and CD8+ T cells secreting the largest numbers and concentrations of relevant SOMAmers. Only CNS-cell-derived protein identified at this stage was glial fibrillary acidic protein (GFAP).

TABLE 5

Selection of SOMAmers important to differentiate MS from controls

| Target | Target Full Name | Entrez Gene Symbol | MS/control fold-change* |
|---|---|---|---|
| ALCAM | CD166 antigen | ALCAM | −1.052 |
| AMHR2 | Anti-Muellerian hormone type-2 receptor | AMHR2 | 1.788 |
| amyloid precursor protein | Amyloid beta A4 protein | APP | −1.200 |
| Nectin-like protein 2 | Cell adhesion molecule 1 | CADM1 | 1.014 |
| MDC | C-C motif chemokine 22 | CCL22 | 1.758 |
| sCD163 | Scavenger receptor cysteine-rich type 1 protein M130 | CD163 | 1.121 |
| CD48 | CD48 antigen | CD48 | 1.609 |
| SLAF5 | SLAM family member 5 | CD84 | 1.281 |
| ARMEL | Cerebral dopamine neurotrophic factor | CDNF | 1.140 |
| Factor D | Complement factor D | CFD | 1.110 |
| Chitotriosidase-1 | Chitotriosidase-1 | CHIT1 | 3.348 |
| IP-10 | C—X—C motif chemokine 10 | CXCL10 | 1.678 |
| I-TAC | C—X—C motif chemokine 11 | CXCL11 | 1.641 |
| BLC | C—X—C motif chemokine 13 | CXCL13 | 1.236 |
| DLL1 | Delta-like protein 1 | DLL1 | 1.020 |
| Desmoglein-2 | Desmoglein-2 | DSG2 | 1.831 |
| XEDAR | Tumor necrosis factor receptor superfamily member 27 | EDA2R | 1.203 |
| Ephrin-A4 | Ephrin-A4 | EFNA4 | 1.179 |
| EphA5 | Ephrin type-A receptor 5 | EPHA5 | 1.034 |
| EPHB2 | Ephrin type-B receptor 2 | EPHB2 | −1.055 |
| TF | Tissue Factor | F3 | 1.049 |
| Coagulation Factor V | Coagulation Factor V | F5 | −1.141 |
| VEGF sR3 | Vascular endothelial growth factor receptor 3 | FLT4 | −1.000 |
| GFAP | Glial fibrillary acidic protein | GFAP | 1.201 |
| GPNMB | Transmembrane glycoprotein NMB | GPNMB | 1.315 |
| granzyme A | Granzyme A | GZMA | 1.500 |
| TIMD3 | Hepatitis A virus cellular receptor 2 | HAVCR2 | 1.299 |

TABLE 5-continued

Selection of SOMAmers important to differentiate MS from controls

| Target | Target Full Name | Entrez Gene Symbol | MS/control fold-change* |
|---|---|---|---|
| IgG | Immunoglobulin G | IGHG1 IGHG2 IGHG3 IGHG4 IGK IGL | 2.486 |
| IL-13 Ra1 | Interleukin-13 receptor subunit alpha-1 | IL13RA1 | 1.007 |
| IL-16 | Interleukin-16 | IL16 | 1.145 |
| IL-17 RC | Interleukin-17 receptor C | IL17RC | 1.001 |
| IL-20 Ra | Interleukin-20 receptor subunit alpha | IL20RA | −1.026 |
| JAM-C | Junctional adhesion molecule C | JAM3 | −1.066 |
| NCAM-L1 | Neural cell adhesion molecule L1 | L1CAM | −1.119 |
| Lymphotoxin a2/b1 | Lymphotoxin alpha2:beta1 | LTA LTB | 1.091 |
| LY9 | T-lymphocyte surface antigen Ly-9 | LY9 | 1.199 |
| MMP-7 | Matrilysin | MMP7 | 1.813 |
| MMP-9 | Matrix metalloproteinase-9 | MMP9 | 2.894 |
| NRX3B | Neurexin-3-beta | NRXN3 | −1.114 |
| TrkC | NT-3 growth factor receptor | NTRK3 | 1.004 |
| OLR1 | Oxidized low-density lipoprotein receptor 1 | OLR1 | 1.373 |
| PIGR | Polymeric immunoglobulin receptor | PIGR | −2.416 |
| GV | Calcium-dependent phospholipase A2 | PLA2G5 | −1.030 |
| ROBO2 | Roundabout homolog 2 | ROBO2 | −1.101 |
| RTN4 | Reticulon-4 | RTN4 | 1.620 |
| Nogo Receptor | Reticulon-4 receptor | RTN4R | −1.081 |
| C1-Esterase Inhibitor | Plasma protease C1 inhibitor | SERPING1 | 1.024 |
| SHC1 | SHC-transforming protein 1 | SHC1 | 1.102 |
| Sonic Hedgehog | Sonic hedgehog protein | SHH | +1.093 |
| SLAF7 | SLAM family member 7 | SLAMF7 | +4.146 |
| STX1a | Syntaxin-1A | STX1A | +1.003 |
| sTie-1 | Tyrosine-protein kinase receptor Tie-1, soluble | TIE1 | −1.004 |
| BCMA | Tumor necrosis factor receptor superfamily member 17 | TNFRSF17 | +3.269 |
| TNF sR-II | Tumor necrosis factor receptor superfamily member 1B | TNFRSF1B | +1.362 |
| DR3 | Tumor necrosis factor receptor superfamily member 25 | TNFRSF25 | +2.164 |
| DcR3 | Tumor necrosis factor receptor superfamily member 6B | TNFRSF6B | +1.009 |
| LIGHT | Tumor necrosis factor ligand superfamily member 14 | TNF5F14 | +1.326 |
| TNFSF15 | Tumor necrosis factor ligand superfamily member 15 | TNFSF15 | +1.377 |
| Troponin I, skeletal, fast twitch | Troponin I, fast skeletal muscle | TNNI2 | +1.716 |
| Dtk | Tyrosine-protein kinase receptor TYRO3 | TYRO3 | −1.051 |
| UFC1 | Ubiquitin-fold modifier-conjugating enzyme 1 | UFC1 | +1.079 |
| VCAM-1 | Vascular cell adhesion protein 1 | VCAM1 | +1.378 |
| WIF-1 | Wnt inhibitory factor 1 | WIF1 | −1.137 |

*To calculate MS/control fold-change, MS subjects (RRMS, PPMS, SPMS) and control subjects (HD, NIND) were pooled from the discovery and the validation cohorts and mean log2-transformed RFU was calculated for each particular biomarker. SOMAmers upregulated in the MS cohort are indicated by positive values, SOMAmers downregulated in MS cohort are indicated by negative values.

Simple Combinatorial Biomarkers: Biomarker Ratios

Figure 17:
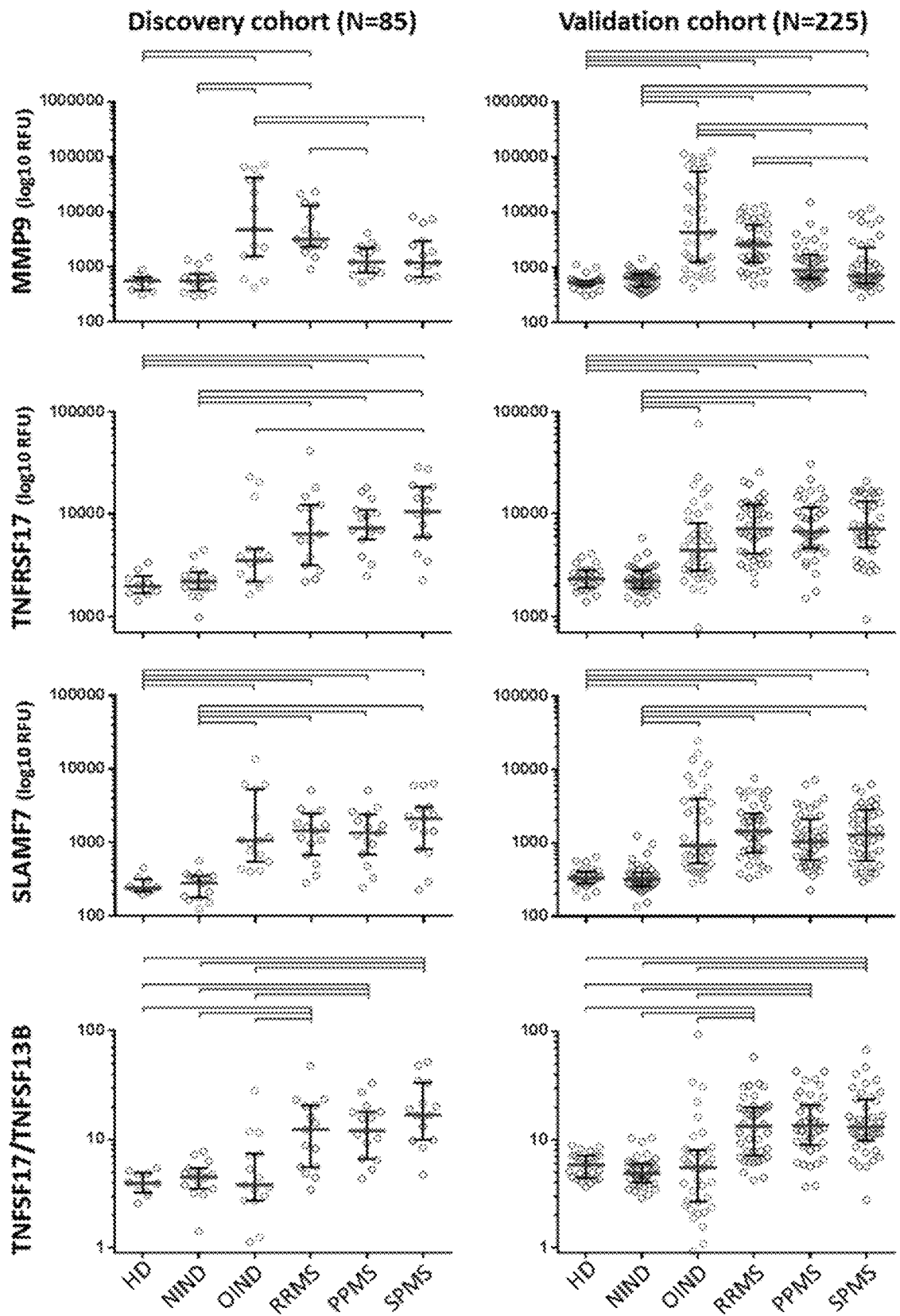
FIG. 17 is a series of graphs showing biomarker distributions between diagnostic categories in the discovery and validation cohorts. Selection of three biomarkers (MMP9, TNFSF17/BCMA, and SLAMF7) that show statistically significant differences between control groups (HD, NIND) and OIND and MS group (RRMS, PPMS, SPMS) in the discovery cohort (N=85, left) and reproducibly significant differences in the larger validation cohort (N=225, right). These three biomarkers were selected to represent the only validated biomarker that differentiates RRMS from PPMS (MMP9) and the two most dominant MS biomarkers (TNFSF17/BCMA, and SLAMF7). Calculation of a ratio between receptor-ligand pair: B-cell maturation antigen BCMA (TNFSF17) and B-cell activating factor BAFF (TNFSF13B) resulted in statistically significant differentiation of MS groups from non-MS inflammatory diseases group (OIND) (bottom panels). Raw RFUs are shown on log 10 axes with a median (middle horizontal bar) and interquartile range (top and bottom horizontal bars). Statistical analysis was performed on log 2-transformed dataset using ordinary one-way ANOVA with Holm-Sidak's multiple comparisons test. The black horizontal bars at the top of each graph show statistically significant differences with adjusted p<0.05.

Since many biomarkers are biologically related (for example, participate in the same in vivo functional network or even physically interact as receptor-ligand pairs), their combined analysis may provide added value (Bielekova et al., Front Neurol 5:102, 2014). Therefore, when studying the concordance between discovery and confirmation cohorts for selected biomarkers (FIG. 17), the ratio between known receptor-ligand pair:B-cell maturation antigen (BCMA; TNFRSF17) and B-cell activating factor (BAFF) was also evaluated. The BCMA/BAFF ratio differentiated MS from all other diagnostic categories with high statistical significance, whereas non-combinatorial biomarkers were not able to do that. Therefore, the identification of unknown relationships between biomarkers by mathematical explorations of biomarker ratios was sought. To avoid excessive number of comparisons, the study focused on 459 biomarkers with high SNR.

Considering the large number of comparisons, the two cohorts were kept separate; however, modeling on the larger cohort (N=225) was performed, which is more representative of the entire MS population, and independently validated on the smaller (N=85) cohort. Using 459 biomarkers, 105,111 pairs of biomarker ratios were generated and their ability to distinguish (1) MS from non-MS and (2) RRMS from progressive MS was assessed.

Nine ratios differentiated MS from other diagnostic categories with AUC>0.9 (FIG. 22A). All of them validated high statistical significance in the smaller (N=85) cohort, with average AUC=0.90. Two plasma cell biomarkers (BCMA and IgG) were present in every one of 9 ratios, while biomarkers of innate immunity were over-represented among their ratio partners. The superiority of biomarker ratios compared to single biomarkers is demonstrated by the fact that only two SOMAmers differentiated MS from non-MS with AUC>0.8: IgG (AUC=0.87) and BCMA (AUC=0.87) and none reached AUC>0.9.

Twenty-four ratios differentiated RRMS from progressive MS with AUC>0.8 in the larger cohort (FIG. 22B). All 24 biomarker ratios validated high statistical significance (with mean AUC=0.81) in the independent smaller cohort. A single biomarker (EDA2R), identified among biomarkers that differentiate MS from HD (FIG. 16), was present in the 15 out of 24 selected ratios. Its ratio pairs consisted of virtually all SOMAmers that the annotation strategy identified as pure or highly-enriched neuronal (L1CAM, ROBO2, RTN4R, NRXN3) or oligodendroglial (JAM3, TYRO3) markers. Again, none of the single SOMAmers differentiated RRMS from progressive MS with AUC>0.8, demonstrating superiority of the biomarker ratios.

Combinatorial Biomarkers: Random Forest

While the data from simple combinatorial biomarkers were highly encouraging, it was investigated if a combination of biomarkers and their ratios, using machine learning classifier, can further improve the performance of molecular diagnostic tests. For each comparison, random forest simulations using three different datasets of biomarkers were used: (1) All 1128 SOMAmers; (2) only 459 SOMAmers with T-SNR and B-SNR>3; and (3) identical 459 SOMAmers plus 9 validated biomarker ratios that differentiated MS from non-MS and 24 validated biomarker ratios that differentiated RRMS from progressive MS. The study modeled on the larger cohort and the smaller cohort was used for independent validation. Only AUCs from the independent validation dataset are presented.

A. MS Versus Non-MS Molecular Diagnostic Test

Figure 18A:
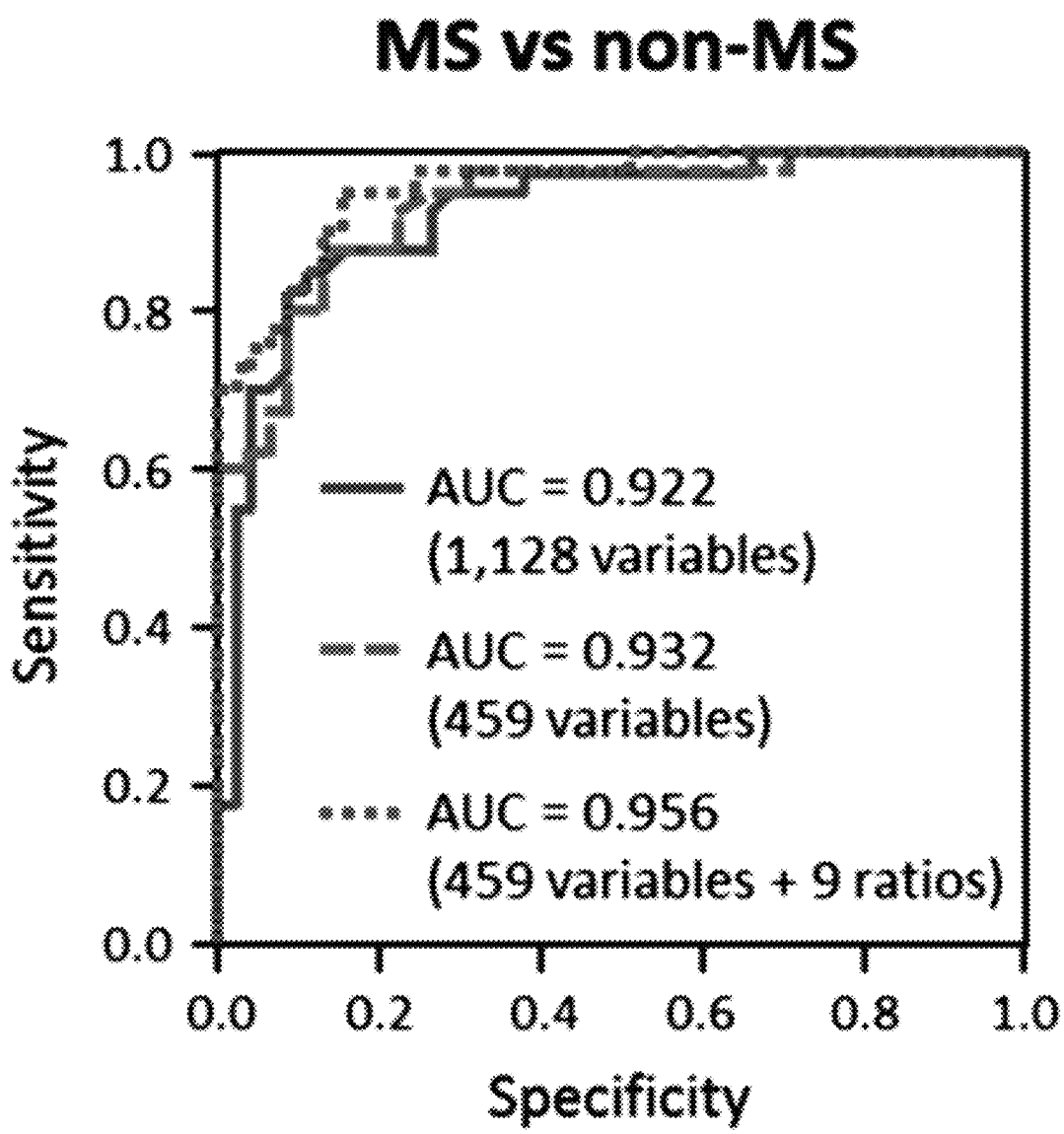
FIGS. 18A-18D relate to a MS versus non-MS molecular diagnostic test.
Figure 18C:
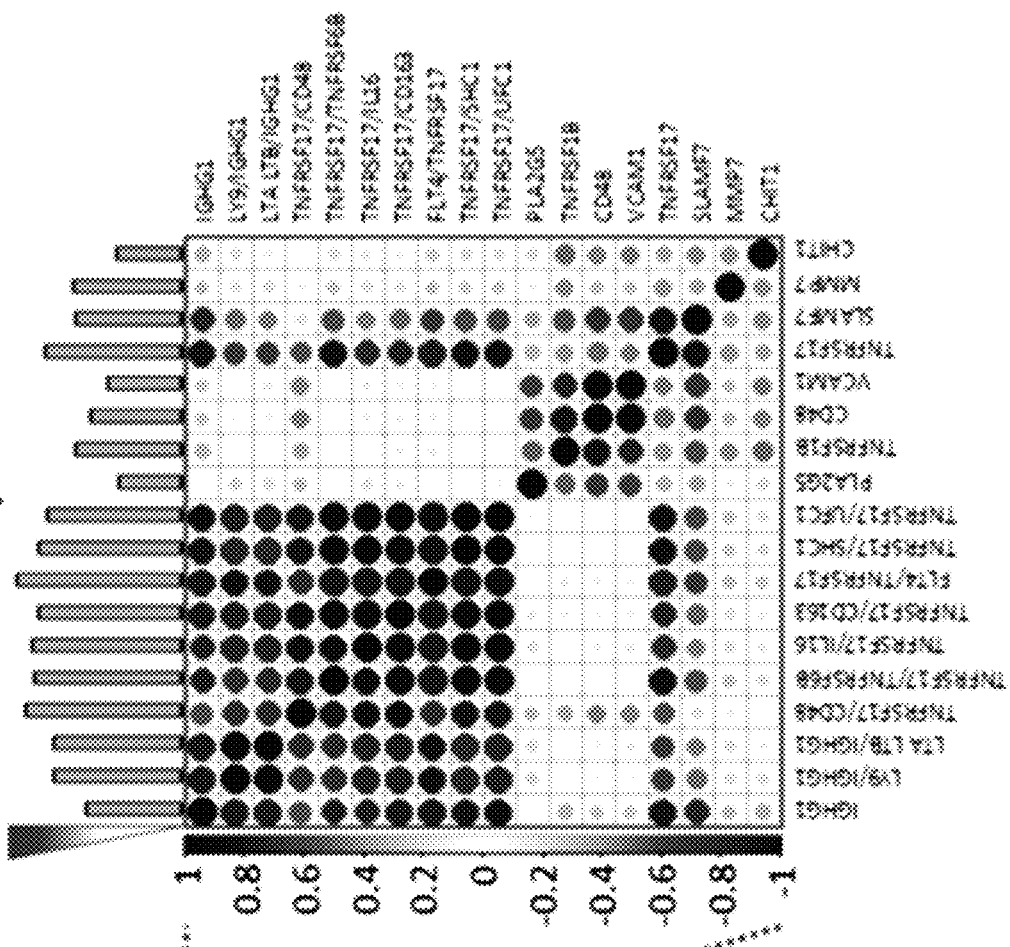
Figure 18B:
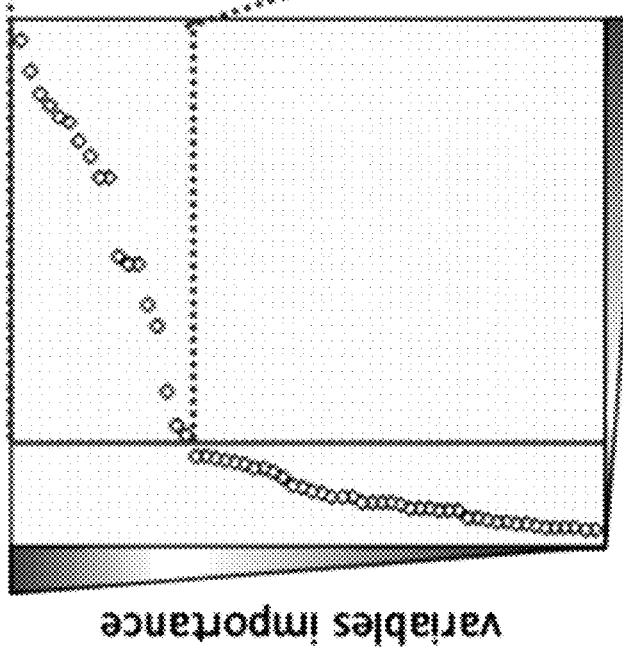
Figure 18D:
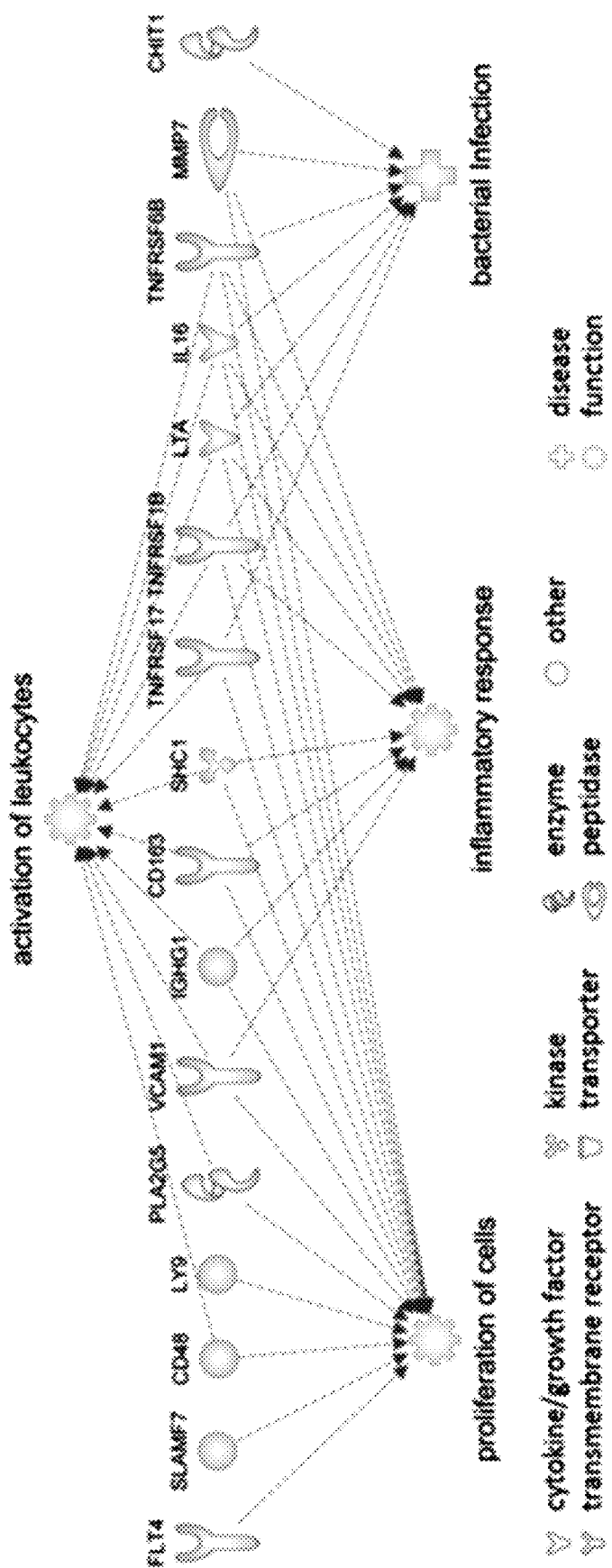

For MS versus non-MS diagnostic test (FIGS. 18A-18D), random forest classifier using all 1128 SOMAmers achieved validated AUC=0.92. Constricting the number of biomarkers to 459 (by eliminating SOMAmers with low SNR) did not decrease, but rather marginally increased the performance of the classifier (AUC=0.93). Adding biomarker ratios further increased the classifiers AUC to 0.96 (FIG. 18A).

When examining variable importance by a hierarchical clustering based on Wards linkage method (FIG. 18B), it was observed that 18 variables dominated the classifier: out of 10 highest ranking variables, 9 were biomarker ratios (TNFSF17/BCMA, representative of single biomarkers, ranked as #7 of variable importance) (Table 6A). Correlation matrix of the 18 most important variables (FIG. 18C) revealed that all biomarker ratios are strongly correlated with each other and with IgG (and moderately with TNFSF17/BCMA). In contrast, smaller correlation module consisted of PLA2G5, TNFRSF1B, CD48 and VCAM, whereas remaining single biomarkers were associated more loosely. The pathway analysis (FIG. 18D) identified identical processes and diseases that were identified in FIG. 16 as differentially expressed between MS and controls.

TABLE 6A

Biomarkers for distinguishing MS versus non-MS subjects

| SomaID(s) | Gene(s) | Target(s) | Variable importance (Random Forest) | AUC Validation cohort (N = 225) | AUC Discovery cohort (N = 85) | correlation with disability accumulation* Spearman r (p value) (N = 269)* |
|---|---|---|---|---|---|---|
| SL003322/ SL004672 | FLT4/ TNFRSF17 | VEGF sR3/ BCMA | 12.86 | 0.91 | 0.89 | −0.311 (<0.0001) |
| SL004672/ SL010450 | TNFRSF17/ CD48 | BCMA/CD48 | 12.24 | 0.90 | 0.90 | 0.277 (<0.0001) |
| SL004672/ SL000474 | TNFRSF17/ IL16 | BCMA/IL-16 | 11.77 | 0.92 | 0.89 | 0.346 (<0.0001) |
| SL004672/ SL003739 | TNFRSF17/ TNFRSF6B | BCMA/DcR3 | 11.54 | 0.90 | 0.92 | 0.328 (<0.0001) |
| SL004672/ SL005764 | TNFRSF17/ CD163 | BCMA/sCD163 | 11.29 | 0.90 | 0.93 | 0.278 (<0.0001) |
| SL004672/ SL014469 | TNFRSF17/ SHC1 | BCMA/SHC1 | 11.19 | 0.90 | 0.87 | 0.289 (<0.0001) |

TABLE 6A-continued

Biomarkers for distinguishing MS versus non-MS subjects

| SomaID(s) | Gene(s) | Target(s) | Variable importance (Random Forest) | AUC Validation cohort (N = 225) | AUC Discovery cohort (N = 85) | correlation with disability accumulation* Spearman r (p value) (N = 269)* |
|---|---|---|---|---|---|---|
| SL004672 | TNFRSF17 | BCMA | 10.78 | 0.84 | 0.87 | |
| SL004672/ SL010529 | TNFRSF17/ UFC1 | BCMA/UFC1 | 10.49 | 0.90 | 0.89 | 0.287 (<0.0001) |
| SL007674/ SL000467 | LY9/ IGHG1 | LY9/IgG | 10.04 | 0.90 | 0.89 | −0.267 (<0.0001) |
| SL000508/ SL000467 | LTA LTB/ IGHG1 | Lymphotoxin a2/b1/IgG | 10.04 | 0.90 | 0.90 | −0.310 (<0.0001) |
| SL000525 | MMP7 | MMP-7 | 8.48 | 0.71 | 0.70 | |
| SL016928 | SLAMF7 | SLAF7 | 8.33 | 0.77 | 0.79 | |
| SL001800 | TNFRSF1B | TNF sR-II | 8.32 | 0.66 | 0.67 | |
| SL000467 | IGHG1 | IgG | 7.50 | 0.86 | 0.87 | |
| SL010450 | CD48 | CD48 | 7.07 | 0.64 | 0.67 | |
| SL001720 | VCAM1 | VCAM-1 | 5.73 | 0.60 | 0.65 | |
| SL006029 | CHIT1 | Chitotriosidase-1 | 5.05 | 0.65 | 0.66 | |
| SL004182 | PLA2G5 | GV | 4.85 | 0.56 | 0.53 | |

*Accumulation of disability in time, as a measure of disease severity was calculated as (100 − SNRS)/age.

B. RRMS Versus Progressive MS Diagnostic Test

Figure 19A:
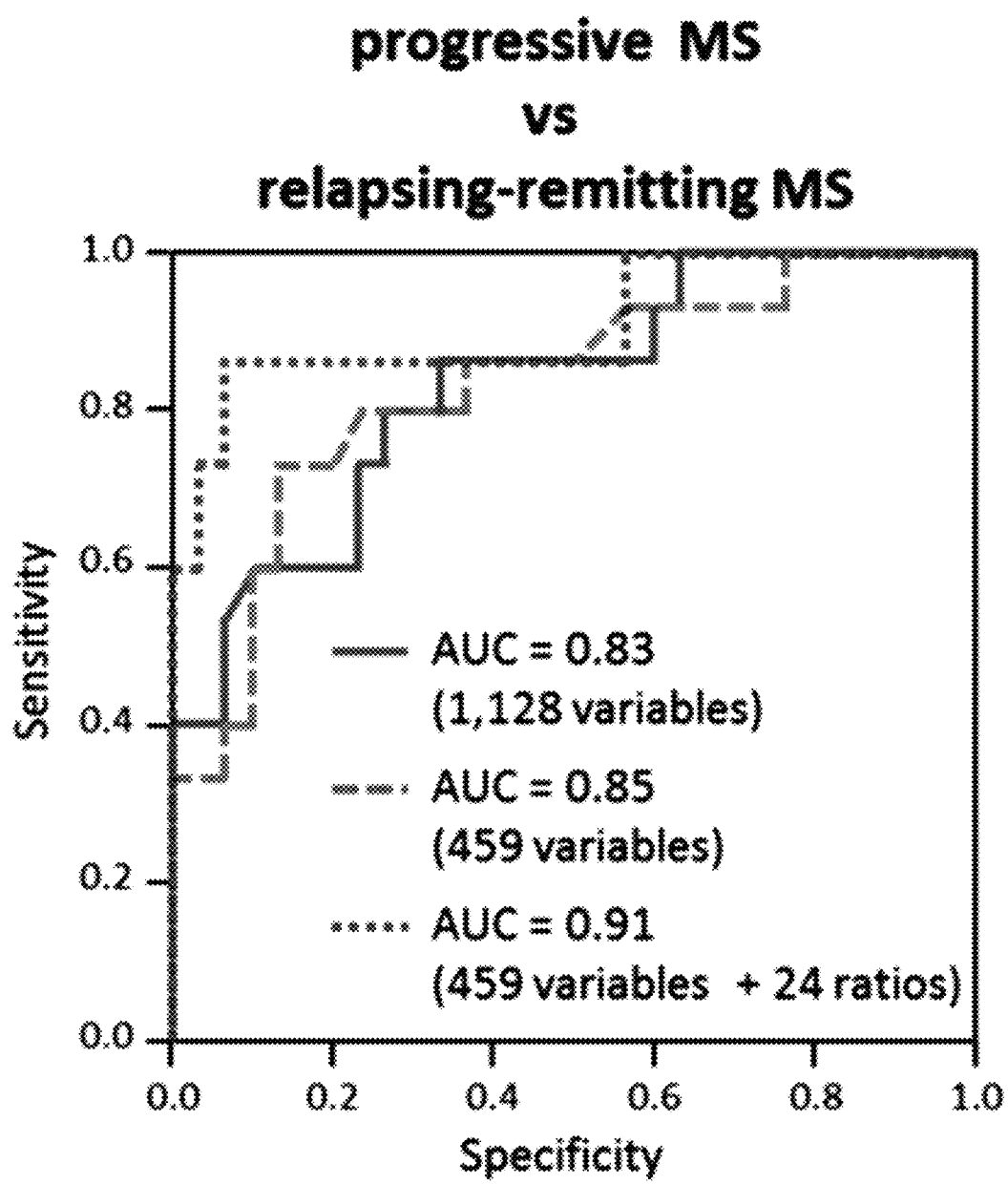
FIGS. 19A-19D relate to a progressive versus RRMS molecular diagnostic test.
Figure 19C:
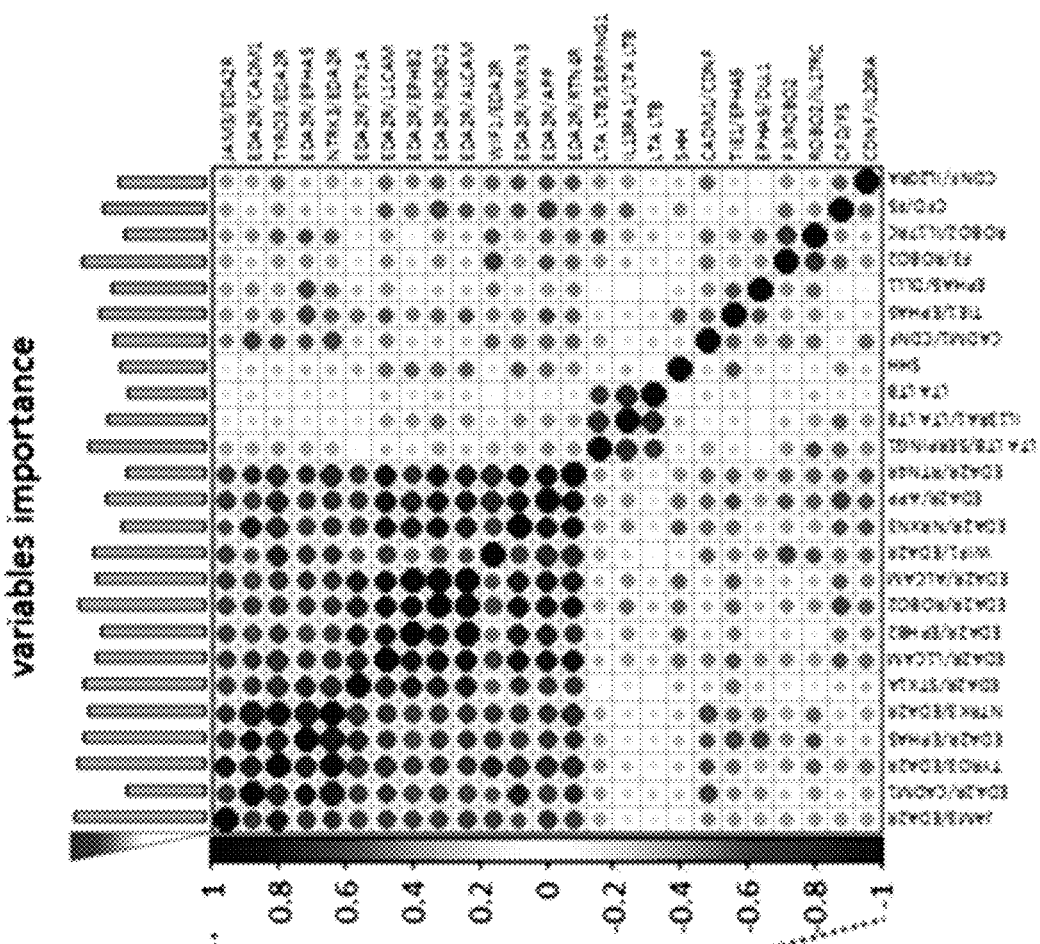
Figure 19B:
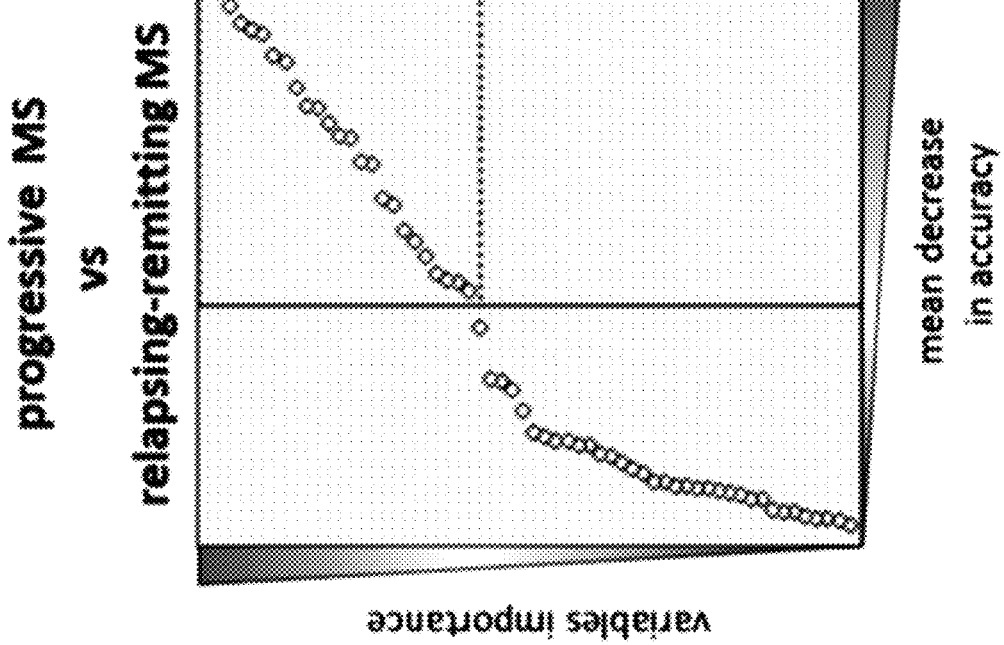
Figure 19D:
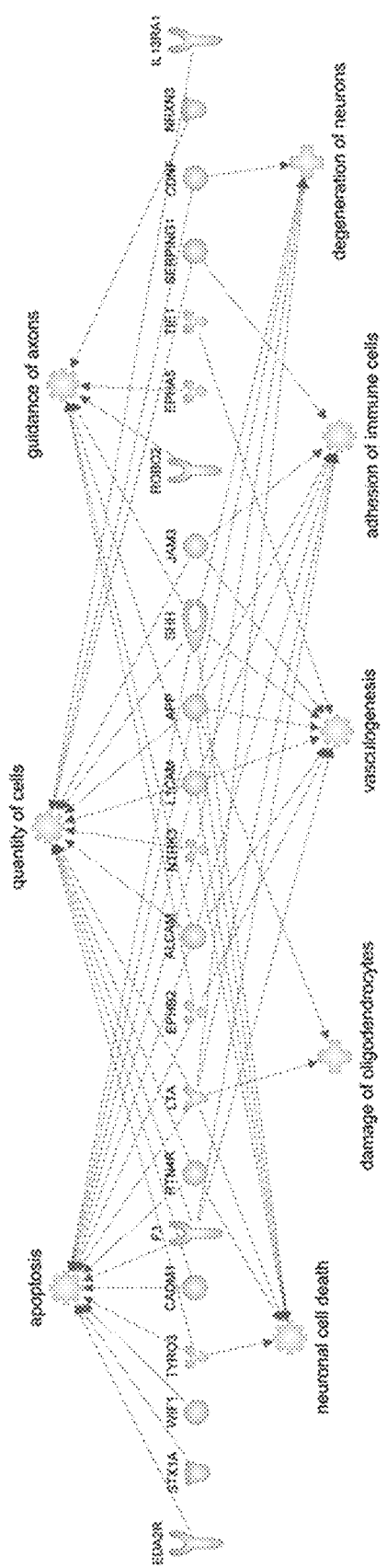

For RRMS versus progressive MS test (FIGS. 19A-19D), random forest classifier using all 1128 SOMAmers achieved validated AUC=0.83 (FIG. 19A). Constricting the number of biomarkers to 459 again enhanced the performance of the classifier (AUC=0.85). Finally, adding biomarker ratios dramatically increased the classifiers AUC to 0.91 (FIG. 19A).

The hierarchical clustering of variable importance plot (FIG. 19B) identified the 25 most important variables for random forest classifier (Table 6B). Again, biomarker ratios completely dominated, representing 23/25 most important variables. Top 25 ranking variables contained only two single proteins, Sonic Hedgehog (SHH; ranked #20) and Lymphotoxin α2/β1 (LTA/LTB; ranked #25). The two highest ranking biomarkers were ratios of EDA2R with oligodendroglial markers JAM3 and TYRO3. The second set of the highest-ranking biomarkers were ratios of neuronal marker ROBO2 with EDA2R and thromboplastin (F3), which is in the CNS expressed predominantly in astrocytes (Zhang et al., J Neurosci 34(36):11929-11947, 2014). The correlation matrix of these 25 highest ranking biomarkers (FIG. 19C) revealed strong correlations between all 14 biomarker ratios containing EDA2R. Another, much smaller clusters of 3 highly correlated biomarkers shared LTA/LTB and remaining 8 biomarkers were not significantly correlated. These included ratios of endothelial cell marker TIE1 (tyrosine kinase with immunoglobulin-like and EGF-like domains; Zhang et al., J Neurosci 34(36):1 1929-11947, 2014) and several ratios containing EPHA5 (EPH receptor A5) and cerebral dopamine neurotrophic factor (CDNF). Ratios containing three cytokine receptors: IL13RA1, IL17RC and IL20RA were among the 25 highest ranking biomarkers. The pathway analysis (FIG. 19D) identified apoptosis, neuronal cell death, quantity of cells, guidance of axons, vasculogenesis and adhesion of immune cells as dominant processes and degeneration of neurons and damage to oligodendrocytes as dominant diseases.

TABLE 6B

Biomarkers for distinguishing progressive MS versus RRMS

| SomaID(s) | Gene(s) | Target(s) | Variable importance (Random Forest) | AUC Validation cohort (N = 225) | AUC Discovery cohort (N = 85) | correlation with disability accumulation* Spearman r (p value) (N = 269) |
|---|---|---|---|---|---|---|
| SL005194/ SL005233 | JAM3/ EDA2R | JAM-C/XEDAR | 7.05 | 0.83 | 0.87 | −0.515 (<0.0001) |
| SL004136/ SL005233 | TYRO3/ EDA2R | Dtk/XEDAR | 6.93 | 0.82 | 0.86 | −0.426 (<0.0001) |
| SL005233/ SL007680 | EDA2R/ ROBO2 | XEDAR/ROBO2 | 6.80 | 0.82 | 0.88 | 0.427 (<0.0001) |
| SL000024/ SL007680 | F3/ ROBO2 | TF/ROBO2 | 6.63 | 0.81 | 0.68 | 0.511 (<0.0001) |
| SL005233/ SL004304 | EDA2R/ STX1A | XEDAR/STX1a | 6.57 | 0.80 | 0.85 | 0.352 (<0.0001) |
| SL005233/ SL004844 | EDA2R/ EPHA5 | XEDAR/EphA5 | 6.52 | 0.84 | 0.87 | 0.347 (<0.0001) |
| SL000508/ SL000308 | LTA LTB/ SERPING1 | Lymphotoxin a2/b1/C1-Esterase Inhibitor | 6.33 | 0.83 | 0.71 | −0.139 (0.0009) |

TABLE 6B-continued

Biomarkers for distinguishing progressive MS versus RRMS

| SomaID(s) | Gene(s) | Target(s) | Variable importance (Random Forest) | AUC Validation cohort (N = 225) | AUC Discovery cohort (N = 85) | correlation with disability accumulation* Spearman r (p value) (N = 269) |
|---|---|---|---|---|---|---|
| SL004639/ SL005233 | NTRK3/ EDA2R | TrkC/XEDAR | 6.27 | 0.83 | 0.87 | −0.349 (<0.0001) |
| SL004652/ SL005233 | WIF1/ EDA2R | WIF-1/XEDAR | 6.04 | 0.82 | 0.74 | −0.405 (<0.0001) |
| SL005233/ SL003166 | EDA2R/ ALCAM | XEDAR/ ALCAM | 5.86 | 0.82 | 0.92 | 0.422 (<0.0001) |
| SL005233/ SL004154 | EDA2R/ L1CAM | XEDAR/ NCAM-L1 | 5.83 | 0.83 | 0.83 | 0.444 (<0.0001) |
| SL003199/ SL004844 | TIE1/ EPHA5 | sTie-1/EphA5 | 5.69 | 0.81 | 0.81 | 0.202 (<0.0001) |
| SL005233/ SL007179 | EDA2R/ EPHB2 | XEDAR/EPHB2 | 5.58 | 0.82 | 0.91 | 0.436 (<0.0001) |
| SL003327/ SL000622 | CFD/ F5 | Factor D/ Coagulation Factor V | 5.55 | 0.80 | 0.72 | 0.361 (<0.0001) |
| SL005233/ SL004469 | EDA2R/ APP | XEDAR/amyloid precursor protein | 5.34 | 0.83 | 0.82 | 0.455 (<0.0001) |
| SL004149/ SL000508 | IL13RA1/ LTA LTB | IL-13 Ra1/ Lymphotoxin a2/b1 | 5.31 | 0.80 | 0.71 | 0.018 (0.7633) |
| SL004844/ SL006970 | EPHA5/ DLL1 | EphA5/DLL1 | 4.98 | 0.80 | 0.72 | −0.137 (0.0244) |
| SL004805/ SL012538 | CADM1/ CDNF | Nectin-like protein 2/ ARMEL | 4.92 | 0.80 | 0.67 | −0.351 (<0.0001) |
| SL012538/ SL005181 | CDNF/ IL20RA | ARMEL/ IL-20 Ra | 4.70 | 0.81 | 0.80 | 0.361 (<0.0001) |
| SL005220 | SHH | Sonic Hedgehog | 4.60 | 0.73 | 0.72 | |
| SL005233/ SL008728 | EDA2R/ NRXN3 | XEDAR/NRX3B | 4.47 | 0.80 | 0.87 | 0.358 (<0.0001) |
| SL007680/ SL011068 | ROBO2/ IL17RC | ROBO2/ IL-17 RC | 4.29 | 0.80 | 0.81 | −0.380 (<0.0001) |
| SL005233/ SL004805 | EDA2R/ CADM1 | XEDAR/Nectin-like protein 2 | 4.24 | 0.80 | 0.88 | 0.363 (<0.0001) |
| SL005233/ SL005208 | EDA2R/ RTN4R | XEDAR/ Nogo Receptor | 4.22 | 0.83 | 0.86 | 0.370 (<0.0001) |
| SL000508 | LTA LTB | Lymphotoxin a2/b1 | 4.14 | 0.79 | 0.61 | |

*Accumulation of disability in time, as a measure of disease severity was calculated as (100 − SNRS)/age.

Diagnostic and Therapeutic Applications

The dominance of immune-related biomarkers in the molecular signature of MS agrees with genetic studies (Sawcer et al., Nature 476(7359):214-219, 2011; International Multiple Sclerosis Genetics Consortium et al., Nat Genet 2013; 45(11):1353-1360). Among the biomarkers identified, TNFSF14 (LIGHT) and SLAMF7 overlap with MS susceptibility genes (Farh et al., Nature 518(7539):337-343, 2015). Analogously to MS genetic studies, enrichment of tumor necrosis factor (TNF) superfamily among MS-specific biomarkers was observed. The dominant signature of plasma cells (IgG and TNFRSF17/BCMA) in MS was also validated. While an equally robust plasma cell signature was observed in OIND controls, there it co-exists with analogously strong activation of monocytes and macrophages. Consequently, ratios of BCMA (or IgG) to biomarkers derived from myeloid cells (e.g. CD163 predominantly expressed in perivascular macrophages) differentiate MS from controls. The present studies also reproduced previous observations (Komori et al., Ann Neurol 78(1):3-20, 2015) that intrathecal inflammation is quantitatively comparable between RRMS and progressive MS, without any molecular differences identified between the PPMS and SPMS cohorts. Overlapping biology supports merging the progressive MS cohorts in future clinical trials.

Synthesizing the functional annotations of identified immune biomarkers, regulation of apoptosis and immune cell activation emerge as major themes. In the former, two sets of TNF superfamily partners were identified: TNFSF14 (LIGHT) and its regulatory partner TNFRSF6B, and TNFSF15 (TL1; expressed on endothelial cells) and its binding partner TNFRSF25 (DR3). In the regulation of immune cells, a strong presence of SLAMF molecules was identified: CD48 (SLAMF2), CD84 (SLAMF5), SLAMF7 (CRACC, CD319) and biomarker ratios also selected LY9 (SLAMF3, CD229). All of these immunoregulatory receptors interact with SLAM-associated protein (SAP) adaptor, which is mutated in X-linked lymphoproliferative disease, characterized by fatal response to Epstein Barr virus (EBV) infection (Cannons et al., Annu Rev Immunol 29:665-705, 2011). EBV is the leading environmental MS susceptibility factor (Ascherio and Munger, Ann Neurol 61(4):288-299, 2007). SLAMF members control interactions between immune cells and thus regulate germinal center reactions, production of immunoglobulins, cytotoxicity, cell adhesion and immune cell survival (Cannons et al., Annu Rev Immunol 29:665-705, 2011). The data disclosed herein indicate that they play a central role in MS and represent novel therapeutic target(s).

Molecular differences were also identified between RRMS and progressive MS. None of the single biomarkers were able to differentiate RRMS from SPMS and only MMP9 differentiated RRMS from PPMS. However, once the biomarker ratios were systematically explored, this mathematical methodology selected those rare SOMAmers that are specific, or highly enriched in oligodendrocytes and neurons. The dominant partner in these biomarker ratios was X-linked ectodysplasin A2 receptor (EDA2R, XEDAR). Its ligand, ectodysplasin A (EDA) is alternatively (and apparently constitutively) spliced into two variants (EDA-A1 and EDA-A2) that, although differing only in two amino acids, bind two distinct receptors: EDAR and EDA2R (Yan et al., *Science* 290(5491):523-527, 2000). All four binding members belong to the TNF superfamily, all can be shed as soluble molecules and their signaling activates NFκB and may mediate apoptosis (Sinha and Chaudhary, *J Biol Chem* 279(40):41873-41881, 2004). While EDA-A1/EDAR is an epithelial morphogen, mutation of which causes X-linked hypohidrotic ectodermal dysplasia characterized by loss of sweat glands, hair follicles and teeth, the physiological functions of EDA-A2/XEDAR are poorly understood (Newton et al., *Mol Cell Biol* 24(4):1608-1613, 2004). Specifically, they are not expressed in large levels in the immune system or in the CNS of adult mice (Newton et al., *Mol Cell Biol* 24(4):1608-1613, 2004). In contrast, decreased expression of XEDAR in several tumors and its interaction with the p53 pathway highlight its tumor-suppressive role (Punj et al., *Clin Cancer Res* 16(4):1140-1148, 2010). Although XEDAR-deficient mice have no apparent phenotype, overexpression of EDA-A2 causes myodegeneration, mediated by XEDAR signaling. Review of ectodysplasin literature suggests the possibility of ectodysplasin's involvement in epithelial morphology. This possibility is supported by identification of desmoglein 2 (DSG2), a component of epithelial cell junctions (desmosomes) among MS-specific proteins.

Validated immune-related biomarkers represent essential tools for the development of effective DMTs for progressive MS and for measuring and therapeutically targeting residual inflammation in (partially) treated RRMS. The pilot OIND data indicate that CSF biomarkers are highly responsive to effective therapies. Focusing on biomarkers with high SNR will ensure that small patient cohorts (in order of 15-20) can provide reliable measurements of intrathecal effects of studied drug(s). In view of the transformative role molecular diagnostics had on therapeutic developments in oncology, it is believed that broader investment into CSF biomarkers and their implementation to Phase I/II trials can have vast societal benefit. It can guide dose and patient selection and eliminate unpromising agents without accruing excessive costs and segregating large numbers of available patients. Additionally, knowledge accumulated from biomarker-supported trials can facilitate development of therapeutic combinations and be translated to neurology clinics.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of identifying a subject with multiple sclerosis (MS) as having progressive MS or relapsing-remitting MS (RRMS), comprising:

measuring biomarkers in a cerebral spinal fluid (CSF) sample obtained from the subject, wherein the biomarkers comprise the ratio of JAM3 to EDA2R, the ratio of TYRO3 to EDA2R, the ratio of EDA2R to ROBO2, the ratio of F3 to ROBO2, the ratio of EDA2R to STX1A, the ratio of EDA2R to EPHA5, the ratio of LTA LTB to SERPING1, the ratio of NTRK3 to EDA2R, the ratio of WIF1 to EDA2R, the ratio of EDA2R to ALCAM, the ratio of EDA2R to L1CAM, the ratio of TIE1 to EPHA5, the ratio of EDA2R to EPHB2, the ratio of CFD to F5, the ratio of EDA2R to APP, the ratio of IL13RA1 to LTA LTB, the ratio of EPHA5 to DLL1, the ratio of CADM1 to CDNF, the ratio of CDNF to IL20RA, SHH, the ratio of EDA2R to NRXN3, the ratio of ROBO2 to IL17RC, the ratio of EDA2R to CADM1, the ratio of EDA2R to RTN4R and LTA LTB; and (i) identifying the subject as having progressive MS if there is a decrease in LTA LTB, the ratio of JAM3 to EDA2R, the ratio of TYRO3 to EDA2R, the ratio of LTA LTB to SERPING1, the ratio of NTRK3 to EDA2R, the ratio of WIF1 to EDA2R, the ratio of EPHA5 to DLL1, the ratio of CADM1 to CDNF, and the ratio of ROBO2 to IL17RC, and an increase in SHH, the ratio of EDA2R to ROBO2, the ratio of F3 to ROBO2, the ratio of EDA2R to STX1A, the ratio of EDA2R to EPHA5, the ratio of EDA2R to ALCAM, the ratio of EDA2R to L1CAM, the ratio of TIE1 to EPHA5, the ratio of EDA2R to EPHB2, the ratio of CFD to F5, the ratio of EDA2R to APP, the ratio of IL13RA1 to LTA LTB, the ratio of CDNF to IL20RA, the ratio of EDA2R to NRXN3, the ratio of EDA2R to CADM1, and the ratio of EDA2R to RTN4R, relative to a control; or (ii) identifying the subject as having RRMS if there is an increase in LTA LTB, the ratio of JAM3 to EDA2R, the ratio of TYRO3 to EDA2R, the ratio of LTA LTB to SERPING1, the ratio of NTRK3 to EDA2R, the ratio of WIF1 to EDA2R, the ratio of EPHA5 to DLL1, the ratio of CADM1 to CDNF, and the ratio of ROBO2 to IL17RC, and a decrease in SHH, the ratio of EDA2R to ROBO2, the ratio of F3 to ROBO2, the ratio of EDA2R to STX1A, the ratio of EDA2R to EPHA5, the ratio of EDA2R to ALCAM, the ratio of EDA2R to L1CAM, the ratio of TIE1 to EPHA5, the ratio of EDA2R to EPHB2, the ratio of CFD to F5, the ratio of EDA2R to APP, the ratio of IL13RA1 to LTA LTB, the ratio of CDNF to IL20RA, the ratio of EDA2R to NRXN3, the ratio of EDA2R to CADM1, and the ratio of EDA2R to RTN4R, relative to a control.

2. The method of claim 1, further comprising administering an appropriate therapy to the subject identified as having progressive MS or RRMS.

3. The method of claim 2, wherein the appropriate therapy comprises immunomodulatory therapy.

4. The method of claim 3, wherein the immunomodulatory therapy comprises administration of a T cell depleting agent.

5. The method of claim 3, wherein the immunomodulatory therapy comprises administration of a B cell depleting agent.

6. The method of claim 1, wherein the control is a reference standard.

7. The method of claim 1, wherein the control is an average value obtained from healthy subjects.

8. The method of claim 1, further comprising obtaining a CSF sample from the subject.

9. The method of claim 1, wherein at least one of the biomarkers is measured using an immunoassay.

10. The method of claim 1, wherein at least one of the biomarkers is measured using an aptamer that specifically binds the biomarker.

11. The method of claim 1, further comprising measuring the level of IL-12p40 in the CSF sample obtained from the subject.

* * * * *